(12) United States Patent
Malcuit et al.

(10) Patent No.: US 10,485,829 B2
(45) Date of Patent: Nov. 26, 2019

(54) METHODS OF PRODUCING HUMAN RPE CELLS AND PHARMACEUTICAL PREPARATIONS OF HUMAN RPE CELLS

(75) Inventors: Christopher Malcuit, Ware, MA (US); Linda Lemieux, Hubbardston, MA (US); William Holmes, Worcester, MA (US); Pedro Huertas, Concord, MA (US); Lucy Vilner, Johnston, RI (US)

(73) Assignee: Astellas Institute for Regenerative Medicine, Marlborough, MA (US)

( * ) Notice: Subject to any disclaimer, the term of this patent is extended or adjusted under 35 U.S.C. 154(b) by 0 days.

(21) Appl. No.: 13/510,426

(22) PCT Filed: Nov. 17, 2010

(86) PCT No.: PCT/US2010/057056
§ 371 (c)(1),
(2), (4) Date: Feb. 28, 2013

(87) PCT Pub. No.: WO2011/063005
PCT Pub. Date: May 26, 2011

(65) Prior Publication Data
US 2013/0149284 A1    Jun. 13, 2013

Related U.S. Application Data

(60) Provisional application No. 61/262,002, filed on Nov. 17, 2009.

(51) Int. Cl.
| | | |
|---|---|---|
| *C12N 5/00* | (2006.01) | |
| *C12N 5/02* | (2006.01) | |
| *A61K 35/12* | (2015.01) | |
| *C12N 5/079* | (2010.01) | |

(52) U.S. Cl.
CPC ............ *A61K 35/12* (2013.01); *C12N 5/0621* (2013.01); *C12N 2506/02* (2013.01)

(58) Field of Classification Search
CPC ...... A61K 35/12; A61K 35/30; C12N 5/0621; C12N 2506/02
See application file for complete search history.

(56) References Cited

U.S. PATENT DOCUMENTS

| | | |
|---|---|---|
| 6,642,048 B2 | 11/2003 | Xu et al. |
| 6,878,543 B1 | 4/2005 | Wahlberg et al. |
| 7,005,252 B1 | 2/2006 | Thomson |
| 7,112,437 B2 | 9/2006 | Pera |
| 7,247,479 B2 | 7/2007 | Kochanek et al. |
| 7,267,981 B2 | 9/2007 | Amit et al. |
| 7,303,912 B2 | 12/2007 | Wahlberg et al. |
| 7,439,064 B2 | 10/2008 | Thomson et al. |
| 7,449,334 B2 | 11/2008 | Thomson et al. |
| 7,504,257 B2 | 3/2009 | Reubinoff et al. |
| 7,604,992 B2 | 10/2009 | Reubinoff |
| 7,651,853 B2 | 1/2010 | Wahlberg et al. |
| 7,736,896 B2 | 6/2010 | Klimanskaya et al. |
| 7,794,437 B2 | 9/2010 | Humayun et al. |
| 7,794,704 B2 | 9/2010 | Klimanskaya et al. |
| 7,795,025 B2 | 9/2010 | Klimanskaya et al. |
| 8,078,267 B2 | 12/2011 | Gellerman et al. |
| 8,133,730 B2 | 3/2012 | Reubinoff |
| 8,137,969 B2 | 3/2012 | Reubinoff et al. |
| 8,158,424 B2 | 4/2012 | Amit et al. |
| 8,222,034 B2 | 7/2012 | Amit et al. |
| 8,252,585 B2 | 8/2012 | Carpenter |
| 8,252,586 B2 | 8/2012 | Carpenter et al. |
| 8,268,303 B2 | 9/2012 | Klimanskaya et al. |
| 8,318,486 B2 | 11/2012 | Amit et al. |
| 8,415,156 B2 | 4/2013 | Tryggvason et al. |
| 8,425,473 B2 | 4/2013 | Ho et al. |
| 8,426,203 B2 | 4/2013 | Thomson et al. |
| 8,460,931 B2 | 6/2013 | Reubinoff et al. |
| 8,501,467 B2 | 8/2013 | Wahlberg et al. |
| 8,535,944 B2 | 9/2013 | Bamdad |
| 8,563,311 B2 | 10/2013 | Amit et al. |
| 8,846,400 B2 | 9/2014 | Amit et al. |

(Continued)

FOREIGN PATENT DOCUMENTS

| | | |
|---|---|---|
| CN | 1449448 A | 10/2003 |
| CN | 101155913 A | 4/2008 |

(Continued)

OTHER PUBLICATIONS

Mayerson et al. "An improved method for isolation and culture of rat retinal pigment epithelial cells", Investigative Ophthalmology and Visual Science 26: 1599-1609, 1985.*
Osakada (Feb. 2008, Nature Biotechnology, 26:215-224).*
Klimanskaya, (2006), Method in Enzymology, 418:169-194.
International Preliminary Report on PCT/US/2010/057056 dated May 31, 2012.
Extended European Search Report dated Jul. 23, 2013 in connection with application No. EP 10832114.2 dated Jul. 23, 2013.
International Preliminary Report on Patentability for Application No. PCT/US2010/057056 dated May 31, 2012.
International Search Report and Written Opinion for Application No. PCT/US2010/057056 dated Aug. 3, 2011.

(Continued)

*Primary Examiner* — Valarie E Bertoglio
(74) *Attorney, Agent, or Firm* — Wolf, Greenfield & Sacks, P.C.

(57) ABSTRACT

The present invention provides improved methods for producing retinal pigmented epithelial (RPE) cells from human embryonic stem cells, human induced pluripotent stem (iPS), human adult stem cells, human hematopoietic stem cells, human fetal stem cells, human mesenchymal stem cells, human postpartum stem cells, human multipotent stem cells, or human embryonic germ cells. The RPE cells derived from embryonic stem cells are molecularly distinct from adult and fetal-derived RPE cells, and are also distinct from embryonic stem cells. The RPE cells described herein are useful for treating retinal degenerative conditions including retinal detachment and macular degeneration.

13 Claims, 24 Drawing Sheets

(56) References Cited

U.S. PATENT DOCUMENTS

| | | |
|---|---|---|
| 8,945,925 B2 | 2/2015 | Amit et al. |
| 9,040,038 B2 | 5/2015 | Klimanskaya et al. |
| 9,040,039 B2 | 5/2015 | Klimanskaya et al. |
| 9,040,770 B2 | 5/2015 | Klimanskaya et al. |
| 9,045,732 B2 | 6/2015 | Klimanskaya et al. |
| 9,080,150 B2 | 7/2015 | Klimanskaya et al. |
| 9,181,524 B2 | 11/2015 | Klimanskaya et al. |
| 9,193,950 B2 | 11/2015 | Klimanskaya et al. |
| 9,200,252 B2 | 12/2015 | Park et al. |
| 9,255,247 B2 | 2/2016 | Amit et al. |
| 9,274,095 B2 | 3/2016 | Humayun et al. |
| 9,359,592 B2 | 6/2016 | Park et al. |
| 9,410,121 B2 | 8/2016 | Amit et al. |
| 9,562,217 B2 | 2/2017 | Klimanskaya et al. |
| 9,649,340 B2 | 5/2017 | Klimanskaya et al. |
| 9,650,605 B2 | 5/2017 | Reubinoff |
| 9,650,607 B2 | 5/2017 | Klimanskaya et al. |
| 9,658,216 B2 | 5/2017 | Reubinoff et al. |
| 9,719,066 B2 | 8/2017 | Tryggvason et al. |
| 9,730,962 B2 | 8/2017 | Klimanskaya et al. |
| 9,732,128 B2 | 8/2017 | West et al. |
| 9,790,466 B2 | 10/2017 | Carpenter et al. |
| 9,850,463 B2 | 12/2017 | Hikita et al. |
| 9,994,815 B2 | 6/2018 | Reichman et al. |
| 10,077,424 B2 | 9/2018 | Malcuit et al. |
| 2002/0022268 A1 | 2/2002 | Xu et al. |
| 2003/0087859 A1 | 5/2003 | Kochanek et al. |
| 2004/0018617 A1 | 1/2004 | Hwang |
| 2004/0086494 A1 | 5/2004 | John |
| 2004/0133095 A1 | 7/2004 | Dunki-Jacobs et al. |
| 2005/0032126 A1 | 2/2005 | Coombs et al. |
| 2006/0002900 A1 | 1/2006 | Binder et al. |
| 2006/0018886 A1 | 1/2006 | Klimanskaya et al. |
| 2006/0031951 A1 | 2/2006 | Klimanskaya |
| 2006/0147437 A1 | 7/2006 | Allen et al. |
| 2006/0286544 A1 | 12/2006 | Mandal et al. |
| 2007/0031386 A1 | 2/2007 | Klimanskaya |
| 2008/0057041 A1 | 3/2008 | Chung et al. |
| 2009/0226955 A1 | 9/2009 | Elliot et al. |
| 2009/0233324 A1 | 9/2009 | Kopf-Sill |
| 2010/0028307 A1 | 2/2010 | O'Neil |
| 2010/0057056 A1 | 3/2010 | Gurtner et al. |
| 2010/0105100 A1 | 4/2010 | Sakurada et al. |
| 2010/0299765 A1 | 11/2010 | Klimanskaya et al. |
| 2011/0027333 A1 | 2/2011 | Idelson et al. |
| 2011/0091869 A1 | 4/2011 | Sasai et al. |
| 2011/0117062 A1 | 5/2011 | Klimanskaya et al. |
| 2011/0117063 A1 | 5/2011 | Klimanskaya et al. |
| 2011/0274662 A1 | 11/2011 | Malcuit et al. |
| 2013/0022680 A1 | 1/2013 | Klimanskaya et al. |
| 2013/0195806 A1 | 8/2013 | Gay et al. |
| 2013/0196369 A1 | 8/2013 | Hikita |
| 2013/0302286 A1 | 11/2013 | Klimanskaya et al. |
| 2013/0302288 A1 | 11/2013 | Klimanskaya et al. |
| 2013/0302426 A1 | 11/2013 | Klimanskaya et al. |
| 2013/0302824 A1 | 11/2013 | Klimanskaya et al. |
| 2013/0316451 A1 | 11/2013 | Klimanskaya et al. |
| 2013/0316452 A1 | 11/2013 | Klimanskaya et al. |
| 2014/0242691 A1 | 8/2014 | Carpenter |
| 2014/0294779 A1 | 10/2014 | Klimanskaya et al. |
| 2014/0315306 A1 | 10/2014 | Tryggvason et al. |
| 2014/0356432 A1 | 12/2014 | Klimanskaya et al. |
| 2015/0086512 A1 | 3/2015 | Malcuit et al. |
| 2015/0125506 A1 | 5/2015 | Idelson et al. |
| 2015/0159134 A1 | 6/2015 | Choudhary et al. |
| 2015/0299653 A1 | 10/2015 | Hovatta et al. |
| 2015/0328261 A1 | 11/2015 | Klimanskaya et al. |
| 2015/0366915 A1 | 12/2015 | Gay et al. |
| 2016/0122711 A1 | 5/2016 | Semechkin et al. |
| 2016/0237403 A1 | 8/2016 | Sawada et al. |
| 2016/0244721 A1 | 8/2016 | Sawada et al. |
| 2016/0312180 A1 | 10/2016 | Amit et al. |
| 2017/0029771 A1 | 2/2017 | Sasai et al. |
| 2017/0067016 A1 | 3/2017 | Tryggvason et al. |
| 2017/0067017 A1 | 3/2017 | Meyer et al. |
| 2018/0008458 A1 | 1/2018 | Banin et al. |
| 2018/0016553 A1 | 1/2018 | Bohana-Kashtan et al. |
| 2018/0023052 A1 | 1/2018 | Klimanskaya et al. |
| 2018/0064761 A1 | 3/2018 | Klimanskaya et al. |
| 2018/0087029 A1 | 3/2018 | Clegg et al. |
| 2018/0119097 A1 | 5/2018 | Eidet et al. |
| 2018/0155682 A1 | 6/2018 | Kida et al. |
| 2018/0230426 A1 | 8/2018 | Bohana-Kashtan et al. |
| 2018/0312805 A1 | 11/2018 | Reubinoff et al. |
| 2019/0062703 A1 | 2/2019 | Malcuit et al. |

FOREIGN PATENT DOCUMENTS

| | | |
|---|---|---|
| CN | 101563449 A | 10/2009 |
| EP | 1 454 641 A2 | 9/2004 |
| EP | 2267116 A1 | 12/2010 |
| EP | 2410044 A3 | 1/2012 |
| EP | 2457999 A2 | 5/2012 |
| EP | 2470645 A1 | 7/2012 |
| EP | 1261691 B1 | 7/2013 |
| EP | 1809739 B1 | 10/2014 |
| EP | 2892996 A2 | 7/2015 |
| EP | 2651973 B1 | 8/2016 |
| EP | 2758427 B1 | 11/2016 |
| EP | 3144319 A1 | 3/2017 |
| EP | 2838992 B1 | 11/2017 |
| EP | 3240612 A1 | 11/2017 |
| EP | 2925856 B1 | 3/2018 |
| EP | 2066786 B1 | 5/2018 |
| EP | 3317404 A1 | 5/2018 |
| JP | H09501303 | 2/1997 |
| JP | 2001-508302 A | 6/2001 |
| JP | 2002-500202 | 1/2002 |
| JP | 2003-111588 A | 4/2003 |
| JP | 2003-523766 | 8/2003 |
| JP | 2003-530879 A | 10/2003 |
| JP | 2003-530880 | 10/2003 |
| JP | 2007-522131 | 8/2007 |
| WO | WO 94/25569 A1 | 11/1994 |
| WO | WO 98/30679 A1 | 7/1998 |
| WO | WO 99/34834 A1 | 7/1999 |
| WO | WO 99/045094 A1 | 9/1999 |
| WO | WO 01/30978 A1 | 5/2001 |
| WO | WO 01/51616 A2 | 7/2001 |
| WO | WO 01/62899 A1 | 8/2001 |
| WO | WO 01/81551 A1 | 11/2001 |
| WO | WO 2001/81549 A2 | 11/2001 |
| WO | WO 02/016620 A2 | 2/2002 |
| WO | WO 02/42445 A2 | 5/2002 |
| WO | WO 2002/092756 A2 | 11/2002 |
| WO | WO 2003/006950 A2 | 1/2003 |
| WO | WO 03/046141 A2 | 6/2003 |
| WO | WO 03/049773 A1 | 6/2003 |
| WO | WO 03/087368 A2 | 10/2003 |
| WO | WO 2005/070011 A2 | 8/2005 |
| WO | WO 2006/040763 A2 | 4/2006 |
| WO | WO 2006/052646 A2 | 5/2006 |
| WO | WO 2006/080952 A2 | 8/2006 |
| WO | WO 2006/085209 A1 | 8/2006 |
| WO | WO 2008/020675 A1 | 2/2008 |
| WO | WO 2008/129554 A1 | 10/2008 |
| WO | WO 2009/050657 A2 | 4/2009 |
| WO | WO2009/051671 | 4/2009 |
| WO | WO 2011/028524 A1 | 3/2011 |
| WO | WO 2011/063005 | 5/2011 |
| WO | WO 2012/012803 | 1/2012 |
| WO | WO 2012/149484 | 11/2012 |
| WO | WO 2013/184809 A1 | 12/2013 |
| WO | WO 2014/037807 A2 | 3/2014 |
| WO | WO 2016/108219 A1 | 7/2016 |
| WO | WO 2017/001589 A1 | 1/2017 |

OTHER PUBLICATIONS

[No Author Listed], A study of implantation of human embryonic stem cell derived retinal pigment epithelium in subjects with acute wet age related macular degeneration and recent rapid vision decline. Last verified Dec. 2013. NCT01691261 http://clinicaltrials.

(56) References Cited

OTHER PUBLICATIONS gov/ct2/show/NCT01691261?term=nct01691261&rank=1 [Accessed Dec. 16, 2013] 3 Pages.
[No Author Listed], ACT confirms Clinical Trial Participant Showed Improvement in Vision Form 20/400 to 20/40 Following Treatment. Press release dated May 16, 2013. http://www.advancedcell.com/news-and-media/press-releases/act-confirms-clinical-trial-participant-showed-improvement-in-vision-from-20-400-to-20-40-following-treatment/index.asp [Last accessed Dec. 16, 2013] 2 Pages.
[No Author Listed], Advanced Cell Technology Announces Interim Data from Its Three Ongoing Macular Degeneration Trials. Press release dated Nov. 8, 2012. http://www.advancedcell.com/documents/0000/0427/advanced-cell-technology-announces-interim-data-from-its-three-ongoing-macular-degeneration-trials.pdf [Last Accessed Dec. 16, 2013] 3 Pages.
[No Author Listed], Advanced Cell Technology Receives Approval from Data Safety Monitoring Board (DSMB) to Initiate Treatment of Third Patient Cohort in All Three Clinical Trials. Press release dated Mar. 2013. http://www.advancedcell.com/documents/0000/0449/advanced-cell-technology-receives-approval-from-data-safety-monitoring-board-dsmb-to-initiate-treatment-of-third-patient-cohort-in-all-three-clinical-trials.pdf [Last Accessed Dec. 16, 2013] 3 Pages.
[No Author Listed], New Science Therapeutics: Regenerative Medicine: Cell Replacement Therapy for Age Related Macular Degeneration. Pfizer-Neusentis, 2002-2012. http://www.neusentis.com/KeyPartnershipCaseStudy.php [Last Accessed Dec. 16, 2013] 3 Pages.
Algvere et al., Long-term outcome of RPE allografts in non-immunosuppressed patients with AMD. Eur J Ophthalmol. Jul.-Sep. 1999;9(3):217-30.
Algvere et al., Transplantation of fetal retinal pigment epithelium in age-related macular degeneration with subfoveal neovascularization. Graefes Arch Clin Exp Ophthalmol. Dec. 1994;232(12):707-16.
Amit et al., "Clonally derived human embryonic stem cell lines maintain pluripotency and proliferative potential for prolonged periods of culture," Dev Biol., Nov. 15, 2000;227(2):271-8.
answers.com. Embryonic Stem Cell. Answers Corp. 2013. http://www.answers.com/topic/embryonic-stem-cell-1. (visited May 12, 2008).
Binder et al. Transplantation of autologous retinal pigment epithelium in eyes with foveal neovascularization resulting from age-related macular degeneration: a pilot study. Am J Ophthalmol. Feb. 2002;133(2):215-25.
Brederlau, Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.
Brewer et al., Optimized survival of hippocampal neurons in B27-supplemented Neurobasal, a new serum-free medium combination. J Neurosci Res. Aug. 1, 1993;35(5):567-76.
Brunt et al., Stem cells and regenerative medicine—future perspectives. Can J Physiol Pharmacol. Mar. 2012;90(3):327-35. doi:10.1139/y2012-007. Epub Mar. 8, 2012.
Buchholz et al., Derivation of functional retinal pigmented epithelium from induced pluripotent stem cells. Stem Cells. Oct. 2009;27(10):2427-34. doi:10.1002/stem.189.
Carpenter et al., "Enrichment of neurons and neural precursors from human embryonic stem cells," Exp Neural., Dec. 2001;172(2):383-97.
Chaudhry et al., Basal medium composition and serum or serum replacement concentration influences on the maintenance of murine embryonic stem cells. Cytotechnology (2008) 5:173-9.
Chaum, Tissue Culture Wash Conditions Significantly Alter Gene Expression in Cultured Human Retinal Pigment Epithelial Cells—A Real Time RT-PCR Study (2005), Invest Ophthalmol Vis Sci 2005;46: E-Abstract 3096.
Chung et al., Human embryonic stem cell lines generated without embryo destruction. Cell Stem Cell. Feb. 7, 2008;2(2):113-7. doi:10.1016/j.stem.2007.12.013. Epub Jan. 10, 2008. Supplemental Material Included. 11 Pages.
Cock et al., Plasmanate: a new plasma substitute for pediatric therapy. Calif Med. Oct. 1958;89(4):257-9.
Cosgrove, Pigment epithelium-derived factor in idiopathic pulmonary fibrosis: a role in aberrant angiogenesis. Am J Respir Crit Care Med. Aug. 1, 2004;170(3):242-51. Epub Apr. 29, 2004.
Cowan et al., Derivation of embryonic stem-cell lines from human blastocysts. N Engl J Med. Mar. 25, 2004;350(13):1353-6. Epub Mar. 3, 2004.
Davis et al., "A human retinal pigment epithelial cell line that retains epithelial characteristics after prolonged culture," Invest Ophthalmol Vis Sci., Apr. 1995;36(5):955-64.
Del Priore et al., Survival of allogeneic porcine retinal pigment epithelial sheets after subretinal transplantation. Invest Ophthalmol Vis Sci. Mar. 2004;45(3):985-92.
Delhaise et al., Establishment of an embryonic stem cell line from 8-cell stage mouse embryos. Eur J Morphol. Nov. 1996;34(4):237-43.
Dunn et al., "ARPE-19, a human retinal pigment epithelial cell line with differentiated properties," Exp Eye Res., Feb. 1996;62(2):155-69.
Duta, The role of bestrophin in airway epithelial ion transport. FEBS Lett. Nov. 19, 2004;577(3):551-4.
Emre et al., A Comparative Analysis of Human Embryonic Stem Cells Cultured in a Variety of Media Conditions. Jan. 1, 2008. 8 Pages. http://www.millipore.com/publications.nsf/a73664f9f981af8c852569b9005b4eee/73159860d3320b8a85257501006111a0/$FILE/an1237en00.pdf [last accessed Dec. 10, 2013].
Faktorovich, Photoreceptor degeneration in inherited retinal dystrophy delayed by basic fibroblast growth factor. Nature. Sep. 6, 1990;347(6288):83-6.
Faustino et al., Automatic Embryonic Stem Cells Detection and Counting Method in Fluorescence Microscopy Images. Monografias em Ciência da Computação. Feb. 1, 2009; p. 1-22.
Frost et al., The importance of imprinting in the human placenta. PLoS Genet. Jul. 1, 2010;6(7):e1001015. doi: 10.1371/journal.pgen.1001015.
Fuhrmann et al., "Extraocular mesenchyme patterns the optic vesicle during early eye development in the embryonic chick" Development, Nov. 2000;127(21):4599-609.
Gepstein et al., Derivation and potential applications of human embryonic stem cells. Circ Res. Nov. 15, 2002;91(10):866-76.
Gong, Effects of extracellular matrix and neighboring cells on induction of human embryonic stem cells into retinal or retinal pigment epithelial progenitors. Exp Eye Res. Jun. 2008;86(6):957-65. doi: 10.1016/j.exer.2008.03.014. Epub Mar. 28, 2008.
Gouras et al., Invest Ophthalmol Vis Sci. Oct. 2002;43(10):3307-11. Retinal degeneration and RPE transplantation in Rpe65(−/−) mice.
Guan, Loss of pigment epithelium derived factor expression in glioma progression. J Clin Pathol. Apr. 2003;56(4):277-82.
Gupta et al., Mechanism and its regulation of tumor-induced angiogenesis. World J Gastroenterol. Jun. 2003;9(6):1144-55.
Hammond, Mechanical culture conditions effect gene expression: gravity-induced changes on the space shuttle. Physiol Genomics. Sep. 8, 2000;3(3):163-73.
Haruta, (2003), The 2nd Japanese Society for Regeneration Medicine, Plenary Convention Program (Abstract).
Haruta, In vitro and in vivo characterization of pigment epithelial cells differentiated from primate embryonic stem cells. Invest Ophthalmol Vis Sci. Mar. 2004;45(3):1020-5.
Haruta, Retinal Pigment Epithelial Cells Differentiated from Primate Embryonic Stem Cells (2003), Invest Ophthalmol Vis Sci., 44:E-Abstract 381.
Haupt et al., Automated selection and collection of pluripotent stem cell colonies using the CellCelector™: Automated collection of hESC colonies. Nature Methods. Jun. 2009; 6(6):iii-iv. http://www.nature.com/nmeth/journal/v6/n6/pdf/nmeth.f.252.pdf [last accessed Dec. 10, 2013].

(56) References Cited

OTHER PUBLICATIONS

Hirano, M. et al., "Generation of Structures Formed by Lens and Retinal Cells Differentiating From Embryonic Stem Cells," Developmental Dynamics, Wiley-Liss, Inc., New York, NY, vol. 228, No. 4, Dec. 2003, pp. 664-671.
Ho et al., Reattachment of cultured human retinal pigment epithelium to extracellular matrix and human Bruch's membrane. Invest Ophthalmol Vis Sci. May 1997;38(6):1110-8.
Hoffman et al., Characterization and culture of human embryonic stem cells, Nat Biotechnol. Jun. 2005;23(6):699-708.
Hori, et al. "Growth inhibitors promote differentiation of insulin-producing tissue from embryonic stem cells" PNAS Dec. 10, 2002 vol. 99 No. 25 pp. 16105-16110.
Hu et al., "A cell culture medium that supports the differentiation of human retinal pigment epithelium into functionally polarized monolayers," Mol Vis., Feb. 7, 2001;7:14-9.
Idelson, Directed differentiation of human embryonic stem cells into functional retinal pigment epithelium cells. Cell Stem Cell. Oct. 2, 2009;5(4):396-408. doi: 10.1016/j.stem.2009.07.002.
Ikeda et al., Generation of Rx+/Pax6+ neural retinal precursors from embryonic stem cells. Proc Natl Acad Sci U S A. Aug. 9, 2005;102(32):11331-6. Epub Aug. 2, 2005.
Inverardi et al., Ch 56: Cell Transplantation. Transplantation Biology: Cellular and Molecular Aspects. Ed. Tiney et al. Lippincott-Raven Publishers, Philadelphia. 1996: 679-87.
Itskovitz-Eldor et al., Differentiation of human embryonic stem cells into embryoid bodies compromising the three embryonic germ layers. Mol Med. Feb. 2000;6(2):88-95.
Jaenisch et al., Stem cells, the molecular circuitry of pluripotency and nuclear reprogramming. Cell. Feb. 22, 2008;132(4):567-82. doi:10.1016/j.cell.2008.01.015.
Jean, Molecular regulators involved in vertebrate eye development. (1998), Mech. Dev., 76:3-18.
Kanuga, Characterization of genetically modified human retinal pigment epithelial cells developed for in vitro and transplantation studies. (2002), Invest Ophthalmol Vis Sci., 43(2):546-555.
Kawamorita, In vitro differentiation of mouse embryonic stem cells after activation by retinoic acid. (2002), Hum Cell, 15(3):178-82.
Kawasaki et al., Induction of midbrain dopaminergic neurons from ES cells by stromal cell-derived inducing activity. Neuron. Oct. 2000;28(1):31-40.
Kawasaki et al., "Generation of dopaminergic neurons and pigmented epithelia from primate ES cells by stromal cell-derived inducing activity," Proceedings of the National Academy of Sciences of USA, National Academy of Science, Washington, DC.vol. 99, No. 3, Feb. 2002, pp. 1580-1585.
Kehat et al., "Human embryonic stem cells can differentiate into myocytes with structural and functional properties of cardiomyocytes," J Clin Invest., Aug. 2001;108(3):407-14.
Kim et al., (2004), Stem Cells, Keystone Symposia, 2004 Abstract Book, p. 94, Abstract 250. 2 Pages.
Klimanskaya Declaration, submitted on Feb. 2, 2010, in the U.S. Appl. No. 11/186,720, pp. 1-5.
Klimanskaya et al. "Derivation and comparative assessment of retinal pigment epithelium from human embryonic stem cells using transcriptomics." Cloning and Stem Cells 6:3, 217-245 2004.
Klimanskaya et al., Human embryonic stem cell lines derived from single blastomeres. Nature. Nov. 23, 2006;444(7118):481-5. Epub Aug. 23, 2006.
Klimanskaya et al., Human embryonic stem cells derived without feeder cells. Lancet. May 7-13, 2005;365(9471):1636-41.
Klimanskaya, (2004), Stem Cells, Keystone Symposia, 2004 Abstract Book, p. 94, Abstract 252. 2 Pages.
Klimanskaya, (2009), in Stem Cell Anthology, Bruce M. Carlson, ed., Academic Press, Chapter 28, pp. 335-346.
Klimanskaya, Derive and conquer: sourcing and differentiating stem cells for therapeutic applications.(2008), Nature Reviews Drug Discovery, 7(2):131-42.
Krivokharchenko et al., Development of parthenogenetic rat embryos. Biol Reprod. Mar. 2003;68(3):829-36.
Kure-Bayashi et al., Successful implantation of in vitro-matured, electro-activated oocytes in the pig. Theriogenology. Mar. 15, 2000;53(5):1105-19.
Lanza et al., Prospects for the use of nuclear transfer in human transplantation. Nat Biotechnol. Dec. 1999;17(12):1171-4.
Lawrence, Schwann cell grafting into the retina of the dystrophic RCS rat limits functional deterioration. Royal College of Surgeons. (2000), Invest., Ophthalmol., & Vis. Sci., 41(2):518-528.
Loi et al., Development of parthenogenetic and cloned ovine embryos: effect of activation protocols. Biol Reprod. May 1998;58(5):1177-87.
Lu et al., "Generation of functional hemangioblasts from human embryonic stem cells" Nature Methods, vol. 4 No. 6, Jun. 2007, 501-509.
Lu, Long-term safety and function of RPE from human embryonic stem cells in preclinical models of macular degeneration. (2009), Stem Cells, 27(9):2126-2135.
Lund et al., Subretinal transplantation of genetically modified human cell lines attenuates loss of visual function in dystrophic rats. Proc Natl Acad Sci U S A. Aug. 14, 2001;98(17):9942-7.
Lund et al. "Cell Transplantation as a Treatment for Retinal Disease," Progress in Retinal and Eye Research, vol. 20, No. 4, Jul. 2001, pp. 415-449.
Ma, Identification of RPE65 in transformed kidney cells. (1999), FEBS Lett., 452(3):199-204.
Makrides, Components of vectors for gene transfer and expression in mammalian cells. Protein Expr Purif. Nov. 1999;17(2):183-202.
Marmostein et al., "Bestrophin, the product of the Best vitelliform macular dystrophy gene (VMD2), localizes to the basolateral plasma membrane of the retinal pigment epithelium," Proc Natl Acad Sci U S A, Nov. 7, 2000;97(23):12758-63.
Marshall et al., Parthenogenetic activation of marmoset (Callithrix jacchus) oocytes and the development of marmoset parthenogenones in vitro and in vivo. Biol Reprod. Dec. 1998;59(6):1491-7.
Motohashi et al., Induction of melanocytes from embryonic stem cells and their therapeutic potential. Pigment Cell Res. Aug. 2006;19(4):284-9.
Muotri, Development of functional human embryonic stem cell-derived neurons in mouse brain. (2005), PNAS, 102(51):18644-18648.
Naldini, Ex vivo gene transfer and correction for cell-based therapies. Nat Rev Genet. May 2011;12(5):301-15. doi: 10.1038/nrg2985. Epub Mar. 29, 2011.
Nguyen et al., Methods to assess stem cell lineage, fate and function. Adv Drug Deliv Rev. Sep. 30, 2010;62(12):1175-86. doi:10.1016/j.addr.2010.08.008. Epub Sep. 9, 2010.
Ohno-Matsui et al., Mol Vis. Aug. 29, 2006;12:1022-32. In vitro and in vivo characterization of iris pigment epithelial cells cultured on amniotic membranes.
Ooto et al., "Induction of the Differentiation of Lentoids from Primate Embryonic Stem Cells," Investigative Ophthalmology & Visual Science, Association for Research in Vision and Ophthalmology, vol. 44, No. 6, Jun. 2003, pp. 2689-2693.
Opas et al., Formation of retinal pigment epithelium in vitro by transdifferentiation of neural retina cells. Int J Dev Biol. Jun. 2001;45(4):633-42.
Ozil et al., Activation of rabbit oocytes: the impact of the Ca2+ signal regime on development. Development. Mar. 2001;128(6):917-28.
Park, In vitro and in vivo analyses of human embryonic stem cell-derived dopamine neurons. (2005), J. Neurochem., 92:1265-1276.
Radtke et al., Vision change after sheet transplant of fetal retina with retinal pigment epithelium to a patient with retinitis pigmentosa. Arch Ophthalmol. Aug. 2004;122(8):1159-65.
Radtke et al., Vision improvement in retinal degeneration patients by implantation of retina together with retinal pigment epithelium. Am J Ophthalmol. Aug. 2008;146(2):172-182. doi:10.1016/j.ajo.2008.04.009. Epub Jun. 10, 2008.
Reik et al., Genomic imprinting: parental influence on the genome. Nat Rev Genet. Jan. 2001;2(1):21-32.

(56) References Cited

OTHER PUBLICATIONS

Reubinoff, B., et al., "Embryonic Stem Cell Lines From Human Blastocysts: Somatic Differentiation in Vitro," Nature Biotechnology, Nature Publishing Group, New York, NY, vol. 18, No. 4, Apr. 2000, pp. 399-404.
Rinaudo, Effects of embryo culture on global pattern of gene expression in preimplantation mouse embryos. (2004), Reproduction, 128(3):301-11.
Saari, Cellular retinaldehyde-binding protein is expressed by oligodendrocytes in optic nerve and brain. (1997), Glia, 21(3):259-68.
Sauve et al. Preservation of visual responsiveness in the superior colliculus of RCS rats after retinal pigment epithelium cell transplantation. Neuroscience. 2002;114(2):389-401.
Schraermeyer et al., "Subretinally Transplanted Embryonic Stem Cell Rescue Photoreceptor Cells From Degeneration in the RCS Rats," Cell Transplantation, 10:673-680.
Schuldiner et al., "Effects of eight growth factors on the differentiation of cells derived from human embryonic stem cells," Proc Natl Acad Sci U S A, Oct. 10, 2000;97(21):11307-12.
Schwartz, Lancet Embryonic stem cell trials for macular degeneration: a preliminary report The Lancet, vol. 379, Issue 9817, pp. 713-720. (http://dx.doi.org/10.1016/S0140-6736(12)60028-2, available on-line Jan. 24, 2012).
Sheridan et al., Expansion of Human Embryonic Stem Cells by Membrane Based Co-Culture. Jan. 1, 2007. Poster. 1 Page. http://www.millipore.com/publications.nsf/a73664f9f981af8c852569b9005b4eee/b08ebcd4e43a4a25852575050063cd4c/$FILE/ps1230en00.pdf [last accessed Dec. 10, 2013].
Skottman, Unique gene expression signature by human embryonic stem cells cultured under serum-free conditions correlates with their enhanced and prolonged growth in an undifferentiated stage. (2006), Stem Cells, 24(1):151-67.
Smith et al., Embryo-derived stem cells: of mice and men. Annu Rev Cell Dev Biol. 2001;17:435-62.
Solter, Differential imprinting and expression of maternal and paternal genomes. Annu Rev Genet. 1988;22:127-46.
Subramanian, Cell transplantation for the treatment of Parkinson's disease. (2001), Seminars Neurol 21(1):103-115.
Sugino et al., Comparison of FRPE and human embryonic stem cell-derived RPE behavior on aged human Bruch's membrane. Invest Ophthalmol Vis Sci. Jul. 1, 2011;52(8):4979-97. doi: 10.1167/iovs.10-5386.
Surani et al., Development of gynogenetic eggs in the mouse: implications for parthenogenetic embryos. Science. Dec. 2, 1983;222(4627):1034-6.
Takahashi et al., Induction of pluripotent stem cells from mouse embryonic and adult fibroblast cultures by defined factors. Cell. Aug. 25, 2006;126(4):663-76. Epub Aug. 10, 2006.
Takahashi, (2003), Geriatric Medicine, 41(12):1791-1795.
Talecris Biotherapeutics, Plasmanate Product Information Sheet, retrieved from http://www.bdipharma.com/Package%20Insert/Talecris/Plasmanate.sub.--- 01-2005.pdf (last visited Jan. 6, 2011).
Thomson, J.A., et al. "Embryonic Stem Cell Lines Derived from Human Blastocysts," Science, American Association for the Advancement of Science, Washington DC, vol. 282, Nov. 1998, pp. 1145-1147.
Thomson, Pluripotent cell lines derived from common marmoset (Callithrix jacchus) blastocysts. (1996), Biol. Reprod., 55:254-259.
Timar et al., Angiogenesis-Dependent Diseases and Angiogenesis Therapy. Pathol Oncol Res. 2001;7(2):85-94.
Tuschl, Effects of cell culture conditions on primary rat hepatocytes-cell morphology and differential gene expression. Toxicology. Feb. 1, 2006;218(2-3):205-15. Epub Dec. 6, 2005.
Van De Velde et al., The four blastomeres of a 4-cell stage human embryo are able to develop individually into blastocysts with inner cell mass and trophectoderm. Hum Reprod. Aug. 2008;23(8):1742-7. doi: 10.1093/humrep/den190. Epub May 24, 2008.
Van Meurs et al., Br J Ophthalmol. Jan. 2004;88(1):110-3. Autologous peripheral retinal pigment epithelium translocation in patients with subfoveal neovascular membranes.
Verfaillie, Stem Cells: Hype and Reality, Hematology Am Soc Hematol Educ Program. 2002:369-81.
Verma et al., Gene therapy—promises, problems and prospects. Nature. Sep. 18, 1997;389(6648):239-42.
Weisz et al., Allogenic fetal retinal pigment epithelial cell transplant in a patient with geographic atrophy, Retina. 1999;19(6):540-5.
Wichterle, Directed differentiation of embryonic stem cells into motor neurons. (2002), Cell, 110:385-397.
Yang, Roles of cell-extrinsic growth factors in vertebrate eye pattern formation and retinogenesis. (2004), Semin Cell Dev Biol., 15:91-103.
Ying, Q.-L., et al. "Conversion of Embryonic Stem Cells Into Neuroctodermal Precursors in Adherent Monoculture," Nature Biotechnology, Nature Publishing Group, New York, NY, vol. 21, No. 2, Feb. 2003, pp. 183-186.
Zaghloul et al., "Step-wise specification of retinal stem cells during normal embryogenesis," Biol Cell, May 2005 ;97(5):321-37.
Zeng, Dopaminergic differentiation of human embryonic stem cells. (2004), Stem Cell, 22:925-940.
Zhang et al., "In vitro differentiation of transplantable neural precursors from human embryonic stem cells," Nat Biotechnol., Dec. 2001;19(12):1129-33.
Zhao, Differentiation and transdifferentiation of the retinal pigment epithelium. (1997), International Rev. Cytology, 171:225-266.
Zhao, In vitro transdifferentiation of embryonic rat retinal pigment epithelium to neural retina. (1995), Brain Res., 677:300-310.
Zhao, X., et al. "Differentiation of Embryonic Stem Cells Into Retinal Neurons," Biochemical and Biophysical Research Communications, vol. 297, No. 2, Sep. 2002, pp. 177-184.
Zhou et al. Novel PAX6 binding sites in the human genome and the role of repetitive elements in the evolution of gene regulation. Genome Res. Nov. 2002;12(11):1716-22.
Znoiko, Identification of the RPE65 protein in mammalian cone photoreceptors. (2002), Invest Ophthalmol Vis Sci., 43(5):1604-9.
Aisenbrey et al., Iris pigment epithelial translocation in the treatment of exudative macular degeneration: a 3-year follow-up. Arch Ophthalmol. Feb. 2006;124(2):183-8.
Algvere et al., Transplantation of RPE in age-related macular degeneration: observations in disciform lesions and dry RPE atrophy. Graefes Arch Clin Exp Ophthalmol Mar. 1997;235(3):149-58.
Aramant et al., Transplanted sheets of human retina and retinal pigment epithelium develop normally in nude rats. Exp Eye Res. Aug. 2002;75(2):115-25.
ATCC entry for ARPE-19, retrieved Mar. 17, 2014 from http://www.atcc.org/products/all/CRL-2302.aspx#characteristics. 1 Page.
Binder et al., Outcome of transplantation of autologous retinal pigment epithelium in age-related macular degeneration: a prospective trial. Invest Ophthalmol Vis Sci. Nov. 2004;45(11):4151-60.
Binder et al., Transplantation of the RPE in AMD. Prog Retin Eye Res. Sep. 2007;26(5):516-54. Epub Mar. 6, 2007. Abstract Only.
Cai et al., Gene expression profile of cultured adult compared to immortalized human RPE. Mol Vis. Jan. 5, 2006;12:1-14.
Canola et al., Retinal stem cells transplanted into models of late stages of retinitis pigmentosa preferentially adopt a glial or a retinal ganglion cell fate. Invest Ophthalmol Vis Sci. Jan. 2007;48(1):446-54.
Carr et al., Protective effects of human iPS-derived retinal pigment epithelium cell transplantation in the retinal dystrophic rat. PLoS One. Dec. 3, 2009;4(12):e8152. doi: 10.1371/journal.pone.0008152.
Crafoord et al., Experimental transplantation of autologous iris pigment epithelial cells to the subretinal space. Acta Ophthalmol Scand. Oct. 2001;79(5):509-14.
Del Cerro et al., Histologic correlation of human neural retinal transplantation. Invest Ophthalmol Vis Sci. Sep. 2000;41(10):3142-8.
Del Priore et al., Triple immune suppression increases short-term survival of porcine fetal retinal pigment epithelium xenografts. Invest Ophthalmol Vis Sci. Sep. 2003;44(9):4044-53.

(56) References Cited

OTHER PUBLICATIONS

Engelmann et al., RPE cell cultivation. Graefes Arch Clin Exp Ophthalmol. Jan. 2004;242(1):65-7. Epub Dec. 5, 2003. First Page Only.
Gullapalli et al., Impaired RPE survival on aged submacular human Bruch's membrane. Exp Eye Res. Feb. 2005;80(2):235-48. Abstract Only.
Haruta et al., [Regeneration of Retinal Function by Cell Transplantation]. Jikken Igaku, 2002; 20(9):1307-1300.
Hu et al., A cell culture medium that supports the differentiation of human retinal pigment epithelium into functionally polarized monolayers. Molecular Vision. Feb. 7, 2001; 7:14-19 http://www.molvis.org/molvis/v7/a3/ [Last accessed Dec. 4, 2013].
Humayun et al., Human neural retinal transplantation. Invest Ophthalmol Vis Sci. Sep. 2000;41(10):3100-6.
Kishi et al., Effects of retinoic acid and TGF-beta 1 on the proliferation and melanin synthesis in chick retinal pigment epithelial cells in vitro. Curr Eye Res. May 1998;17(5):483-6. Abstract Only.
Kniazeva et al., Clinical and genetic studies of an autosomal dominant cone-rod dystrophy with features of Stargardt disease. Ophthalmic Genet. Jun. 1999;20(2):71-81.
Kohen et al., Mechanisms of graft rejection in the transplantation of retinal pigment epithelial cells. Ophthalmic Res. 1997;29(5):298-304. Abstract only.
Lappas et al., Iris pigment epithelial cell translocation in exudative age-related macular degeneration. A pilot study in patients. Graefes Arch Clin Exp Ophthalmol. Aug. 2000;238(8):631-41. Abstract Only.
Lee et al., Spatial cues for the enhancement of retinal pigment epithelial cell function in potential transplants. Biomaterials. Apr. 2007;28(13):2192-201. Epub Jan. 11, 2007. Abstract only.
Liao et al., Molecular signature of primary retinal pigment epithelium and stem-cell-derived RPE cells. Hum Mol Genet. Nov. 1, 2010;19(21):4229-38. doi: 10.1093/hmg/ddq341. Epub Aug. 13, 2010.
Liu et al., Integrated analysis of DNA methylation and RNA transcriptome during in vitro differentiation of human pluripotent stem cells into retinal pigment epithelial cells. PLoS One. Mar. 17, 2014;9(3):e91416. doi:10.1371/journal.pone.0091416. eCollection 2014.
Lu et al., Long-term safety and function of RPE from human embryonic stem cells in preclinical models of macular degeneration. Stem Cells. Sep. 2009;27(9):2126-35. doi: 10.1002/stem.149.
Maclaren et al., Autologous transplantation of the retinal pigment epithelium and choroid in the treatment of neovascular age-related macular degeneration. Ophthalmology. Mar. 2007;114(3):561-70. Abstract only.
Maclaren et al., Long-term results of submacular surgery combined with macular translocation of the retinal pigment epithelium in neovascular age-related macular degeneration. Ophthalmology. Dec. 2005;112(12):2081-7. Abstract Only.
Maminishkis et al., Confluent monolayers of cultured human fetal retinal pigment epithelium exhibit morphology and physiology of native tissue. Invest Ophthalmol Vis Sci. Aug. 2006;47(8):3612-24.
Proulx et al., Integrin alpha5 expression by the ARPE-19 cell line: comparison with primary RPE cultures and effect of growth medium on the alpha5 gene promoter strength. Exp Eye Res. Aug. 2004;79(2):157-65.
Sauvé et al., Visual field loss in RCS rats and the effect of RPE cell transplantation. Exp Neurol. Aug. 1998;152(2):243-50. Abstract only.
Song et al., Propagation of fetal human RPE cells: preservation of original culture morphology after serial passage. J Cell Physiol. Apr. 1990;143(1):196-203. Abstract Only.
Stanga et al., Retinal pigment epithelium translocation after choroidal neovascular membrane removal in age-related macular degeneration. Ophthalmology. Aug. 2002;109(8):1492-8. Abstract only.
Strauss, The retinal pigment epithelium in visual function. Physiol Rev. Jul. 2005;85(3):845-81.
Takahashi, Nihon Saisei-Iryo Gakkai zasshi, 2004; 3(2):76-80.
Tamai, [Retinal pigment epithelial cell transplantation: perspective]. Nihon Ganka Gakkai Zasshi. Dec. 1996;100(12):982-1006.
Tezel et al., Adult retinal pigment epithelial transplantation in exudative age-related macular degeneration. Am J Ophthalmol. Apr. 2007;143(4):584-95. Epub Feb. 14, 2007. Abstract Only.
Tezel et al., Serum-free media for culturing and serial-passaging of adult human retinal pigment epithelium. Exp Eye Res. Jun. 1998;66(6):807-15. Abstract Only.
Thumann et al., Transplantation of autologous iris pigment epithelium after removal of choroidal neovascular membranes. Arch Ophthalmol. Oct. 2000;118(10):1350-5.
Tian et al., The expression of native and cultured RPE grown on different matrices. Physiol Genomics. Apr. 13, 2004;17(2):170-82. Abstract only.
Treumer et al., Autologous retinal pigment epithelium-choroid sheet transplantation in age related macular degeneration: morphological and functional results. Br J Ophthalmol. Mar. 2007;91(3):349-53. Epub Oct. 11, 2006.
Wang et al., Grafting of ARPE-19 and Schwann cells to the subretinal space in RCS rats. Invest Ophthalmol Vis Sci. Jul. 2005;46(7):2552-60.
Wang et al., Transplantation of reprogrammed embryonic stem cells improves visual function in a mouse model for retinitis pigmentosa. Transplantation. Apr. 27, 2010;89(8):911-9. doi: 10.1097/TP.0b013e3181d45a61.
Aronson, Human retinal pigment cell culture. In Vitro. Aug. 1983;19(8):642-50.
Berger et al., Photoreceptor transplantation in retinitis pigmentosa: short-term follow-up. Ophthalmology. Feb. 2003;110(2):383-91.
Cursiefen et al., Chapter 5: Special Anatomy and Pathology in Intraocular Microsurgery, Cornea and Limbus. In Applied Pathology for Ophthalmic Microsurgeons, Eds. Naumann et al. Springer-Verlag Berlin Heidelberg. 2008;97-349.
Kaplan et al., Retinal transplantation. Chem Immunol. 1999;73:207-19.
Kaplan et al., Human photoreceptor transplantation in retinitis pigmentosa. A safety study. Arch Ophthalmol. Sep. 1997;115(9):1168-72. Abstract only.
Little et al., Transplantation of human fetal retinal pigment epithelium rescues photoreceptor cells from degeneration in the Royal College of Surgeons rat retina. Invest Ophthalmol Vis Sci. Jan. 1996;37(1):204-11.
Lu et al., Expression of melanin-related genes in cultured adult human retinal pigment epithelium and uveal melanoma cells. Mol Vis. Nov. 3, 2007;13:2066-72.
Ma et al., Expression, purification, and MALDI analysis of RPE65. Invest Ophthalmol Vis Sci. Jun. 2001;42(7):1429-35.
Peyman et al., A technique for retinal pigment epithelium transplantation for age-related macular degeneration secondary to extensive subfoveal scarring. Ophthalmic Surg. Feb. 1991;22(2):102-8.
Ray et al., SV40 T antigen alone drives karyotype instability that precedes neoplastic transformation of human diploid fibroblasts. J Cell Biochem. Jan. 1990;42(1):13-31.
Redmond, Focus on Molecules: RPE65, the visual cycle retinol isomerase. Exp Eye Res. May 2009;88(5):846-7. doi: 10.1016/j.exer.2008.07.015. Epub Aug. 14, 2008.
Schwartz et al., Human embryonic stem cell-derived retinal pigment epithelium in patients with age-related macular degeneration and Stargardt's macular dystrophy: follow-up of two open-label phase 1/2 studies. Lancet. Oct. 15, 2014. pii: S0140-6736(14)61376-3. doi: 10.1016/S0140-6736(14)61376-3. [Epub ahead of print].
Vugler et al., Elucidating the phenomenon of HESC-derived RPE: anatomy of cell genesis, expansion and retinal transplantation. Exp Neurol. Dec. 2008;214(2):347-61. doi: 10.1016/j.expneurol.2008.09.007. Epub Sep. 27, 2008.
Zhu et al., Isolation, culture and characteristics of human foetal and adult retinal pigment epithelium. Aust N Z J Ophthalmol. May 1998;26 Suppl 1:S50-2.
[No Author Listed] Research Committee on Chorioretinal Degeneration and Optic Atrophy. The Ministry of Health, Labour and Welfare of Japan. 2002. 132-140.

(56) References Cited

OTHER PUBLICATIONS

Armstrong, UK House Parliaments' Select Committee on Science and Technology, Fifth Report of Session. Jul. 2006. Apr. 5, 2007; vol. II: 76-80.
Flood et al., Growth characteristics and ultrastructure of human retinal pigment epithelium in vitro. Invest Ophthalmol Vis Sci. Nov. 1980;19(11):1309-20.
Moon et al., Generation, culture, and differentiation of human embryonic stem cells for therapeutic applications. Mol Ther. Jan. 2006;13(1):5-14. Epub Oct. 20, 2005.
Schwartz, Embryonic stem cell trials for macular degeneration: a preliminary report The Lancet, vol. 379, Issue 9817, pp. 713-720. (http://dx.doi.org/10.1016/S0140-6736(12)60028-2, available online Jan. 24, 2012). Supplementary Web Appendix. 21 pages.
Zheng et al., Involvement of rho-kinase pathway in contractile activity of rabbit RPE cells in vivo and in vitro. Invest Ophthalmol Vis Sci. Feb. 2004;45(2):668-74.
U.S. Appl. No. 12/857,866, filed Aug. 17, 2010, Published, 2011-0117062.
U.S. Appl. No. 13/858,376, filed Apr. 8, 2013, Published, 2013-0302426.
U.S. Appl. No. 13/858,354, filed Apr. 8, 2013, Published, 2013-0302286.
U.S. Appl. No. 14/692,191, filed Apr. 21, 2015, Published, 2015-0328261.
U.S. Appl. No. 14/254,833, filed Apr. 16, 2014, Published, 2015-0086512.
U.S. Appl. No. 14/713,108, filed May 15, 2015, Pending, 2015-0366915.
[Author Not Known] Advances on in vitro induced differentiation of embyonic stem cells into melanocytes. J Tissue Eng Reconstr Surg. Oct. 2008;4(5):292-4. Chinese language reference.
Inumaru et al., Molecular mechanisms regulating dissociation of cell-cell junction of epithelial cells by oxidative stress. Genes Cells. Jun. 2009;14(6):703-16. doi: 10.1111/j.1365-2443.2009.01303.x. Epub Apr. 30, 2009.
Itoh et al., Inhibition of RhoA/Rho-kinase pathway suppresses the expression of type I collagen induced by TGF-beta2 in human retinal pigment epithelial cells. Exp Eye Res. Mar. 2007;84(3):464-72. Epub Jan. 10, 2007.
Kishi et al., Role of TGF-beta in the retinoic acid-induced inhibition of proliferation and melanin synthesis in chick retinal pigment epithelial cells in vitro. Cell Biol Int. 2001;25(11):1125-9.
Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.
Mitalipov et al., Isolation and characterization of novel rhesus monkey embryonic stem cell lines. Stem Cells. Oct. 2006;24(10):2177-86. Epub Jun. 1, 2006.
Osakada et al., In vitro differentiation of retinal cells from human pluripotent stem cells by small-molecule induction. J Cell Sci. Sep. 1, 2009;122(Pt 17):3169-79. doi: 10.1242/jcs.050393. Epub Aug. 11, 2009.
Schulz et al., Directed neuronal differentiation of human embryonic stem cells. BMC Neurosci. Oct. 22, 2003;4:27.
Sheridan et al., Replacement of the RPE monolayer. Eye (Lond). Oct. 2009;23(10):1910-5. doi: 10.1038/eye.2008.420. Epub Jan. 23, 2009.
Shirakawa et al., Special Topic: Tissue culture in ophthalmologic field. Culture of retinal pigmented epithelial cells. Ophthalmology. 1986;28:119-34. Japanese language reference.
Sonoda et al., A protocol for the culture and differentiation of highly polarized human retinal pigment epithelial cells. Nat Protoc. 2009;4(5):662-73. doi: 10.1038/nprot.2009.33.
[No Author Listed] Center for veterinary medicine program policy and procedures manual. Sterility and pyrogen requirements for injectable drug products. Apr. 25, 2000. Guide 1240.4122. 5 pages.
[No Author Listed] Medium System for MDBK Cells. Sigma Product Nos. M 3553 and M 0682. Product Information sheet. Sigma ®. Sigma-Aldrich, Inc. May 29, 2003. 2 pages.
Basak et al., Human embryonic stem cells hemangioblast express HLA-antigens. J Transl Med. Apr. 2009;7:27.
Dong et al., Differentiation of human neural stem cells into retinal cells. Neuroreport. Jan. 20, 2003;14(1):143-6.
Gonzalo, Epigenetic alterations in aging. J Appl Physiol. May 3, 2010;109:586-97. doi: 10.1152/japplphysiol.00238.2010.
Murisier et al., Genetics of pigment cells: lessons from the tyrosinase gene family. Histol Histolopathol. 2006;21:567-78.
Pedersen, Studies of in vitro differentiation with embryonic stem cells. Reprod Fertil Dev. 1994;6(5):543-52.
Rogojina et al., Comparing the use of Affymetrix to spotted oligonucleotide microarrays using two retinal pigment epithelium cell lines. Mol Vis. Oct. 6, 2003;9:482-96.
Svendsen et al., Increased survival of rat EGF-generated CNS precursor cells using B27 supplemented medium. Exp Brain Res. 1995;102(3):407-14.
Wang et al., Advances on in vitro induced differentiation of embyonic stem cells into melanocytes. J Tissue Eng Reconstr Surg. Oct. 2008;4(5):292-4. Chinese language reference.
Wistow et al., Expressed sequence tag analysis of human RPE/choroid for the NEIBank Project: over 6000 non-redundant transcripts, novel genes and splice variants. Mol Vis. Jun. 15, 2002;8:205-20. http://www.molvis.org/molvis/v8/a27/.
Abdul-Hassan et al., Optimization of non-viral gene transfer to human primary retinal pigment epithelial cells. Current Eye Research. 2000;20(5):361-6.
Boulton et al., Retinitis Pigmentosa: A Preliminary Report on Tissue Culture Studies of Retinal Pigment Epithelial Cells from Eight Affected Human Eyes. Exp. Eye Res. 1983; 37 (307-314).
Grierson et al., Development, repair and regeneration of the retinal pigment epithelium. Eye. 1994;8:255-62.
Lee et al., Epitheliomesenchymal transdifferentiation of cultured RPE cells. Ophthalmic Res. 2001;33(2):80-6.
Opas et al., bFGF-induced transdifferentiation of RPE to neuronal progenitors is regulated by the mechanical properties of the substratum. Dev Biol. 1994;161:440-54.
U.S. Appl. No. 13/477,763, filed May 22, 2012, Granted, U.S. Pat. No. 9,080,150.
U.S. Appl. No. 15/653,472, filed Jul. 21, 2017, Published, 2018-0064761.
U.S. Appl. No. 12/682,712, filed Dec. 14, 2010, Published, 2011-0274662.
U.S. Appl. No. 14/254,833, filed Apr. 16, 2014, Granted, U.S. Pat. No. 10,077,424.
U.S. Appl. No. 16/113,717, filed Aug. 27, 2018, Pending.
U.S. Appl. No. 13/676,999, filed Nov. 14, 2012, Abandoned, 2013-0195806.
Berrill et al., Assessment of stem cell markers during long-term culture of mouse embryonic stem cells. Cytotechnology. Jan. 2004;44(1-2):77-91. doi: 10.1023/B:CYTO.0000043414.90681.c2.
Catanuto et al., Mouse retinal pigmented epithelial cell lines retain their phenotypic characteristics after transfection with human papilloma virus: A new tool to further the study of RPE biology. Exp Eye Res. Jan. 2009;88(1):99-105. doi: 10.1016/j.exer.2008.10.013. Epub Nov. 1, 2008.
Dunn et al., Use of the ARPE-19 cell line as a model of RPE polarity: Basolateral secretion of FGF5. Invest Ophthalmol Vis Sci. Dec. 1998;39(13):2744-9.
Economopoulou et al., Expression, localization, and function of junctional adhesion molecule-C (JAM-C) in human retinal pigment epithelium. Invest Ophthalmol Vis Sci. Mar. 2009;50(3):1454-63. doi: 10.1167/iovs.08-2129. Epub Dec. 5, 2008.
Pease et al., Isolation of embryonic stem (ES) cells in media supplemented with recombinant leukemia inhibitory factor (LIF). Dev Biol. Oct. 1990;141(2):344-52.
U.S. Appl. No. 11/041,382, filed Jan. 24, 2005, Granted, U.S. Pat. No. 7,794,704.
U.S. Appl. No. 11/490,953, filed Jul. 21, 2006, Granted, U.S. Pat. No. 7,795,025.

(56) References Cited

OTHER PUBLICATIONS

U.S. Appl. No. 12/857,911, filed Aug. 17, 2010, Granted, U.S. Pat. No. 8,268,303.
U.S. Appl. No. 12/857,866, filed Aug. 17, 2010, Granted, U.S. Pat. No. 9,649,340.
U.S. Appl. No. 13/477,763, filed Sep. 22, 2012, Granted, U.S. Pat. No. 9,080,150.
U.S. Appl. No. 13/858,376, filed Apr. 8, 2013, Granted, U.S. Pat. No. 9,650,607.
U.S. Appl. No. 13/858,354, filed Apr. 8, 2013, Granted, U.S. Pat. No. 9,562,217.
U.S. Appl. No. 13/858,534, filed Apr. 8, 2013, Granted, U.S. Pat. No. 9,040,038.
U.S. Appl. No. 13/858,497, filed Apr. 8, 2013, Granted, U.S. Pat. No. 9,045,732.
U.S. Appl. No. 13/865,751, filed Apr. 18, 2013, Granted, U.S. Pat. No. 9,040,039.
U.S. Appl. No. 14/227,237, filed Mar. 27, 2014, Granted, U.S. Pat. No. 9,181,524.
U.S. Appl. No. 14/227,305, filed Mar. 27, 2014, Granted, U.S. Pat. No. 9,193,950.
U.S. Appl. No. 15/495,917, filed Apr. 24, 2017, Published, 2018-0023052.
U.S. Appl. No. 14/922,366, filed Oct. 26, 2015, Abandoned.
U.S. Appl. No. 11/186,720, filed Jul. 20, 2005, Granted, U.S. Pat. No. 7,736,896.
U.S. Appl. No. 12/781,929, filed May 18, 2010, Granted, U.S. Pat. No. 9,040,770.
U.S. Appl. No. 14/692,191, filed Apr. 21, 2015, Granted, U.S. Pat. No. 9,730,962.
U.S. Appl. No. 15/653,472, filed Jul. 21, 2017, Pending, 2018-0064761.
U.S. Appl. No. 15/682,712, filed Dec. 14, 2010, Abandoned, 2011-0274662.
U.S. Appl. No. 14/254,833, filed Apr. 16, 2014, Allowed, 2015-0086512.
U.S. Appl. No. 13/510,426, filed Feb. 28, 2013, Published, 2013-0149284.
U.S. Appl. No. 13/676,999, filed Nov. 14, 2012, Published, 2013-0195806.
U.S. Appl. No. 14/713,108, filed May 15, 2015, Published, 2015-0366915.
Richards et al., Comparative evaluation of various human feeders for prolonged undifferentiated growth of human embryonic stem cells. Stem Cells. 2003;21(5):546-56.
Xu et al., Feeder-free growth of undifferentiated human embryonic stem cells. Nat Biotechnol. Oct. 2001;19(10):971-4.
Durlu, Y., et al. "Transplantation of Retinal Pigment Epithelium Using Viable Cryopreserved Cells," Cell Transplantation, vol. 6, No. 2, p. 149-162. 1997.
Valtink, M., et al. "Culturing of Retinal Pigment Epithelium Cells," Eye Banking. Dev Ophthalmol. Basel, Karger, 2009, vol. 43, pp. 109-119.

* cited by examiner

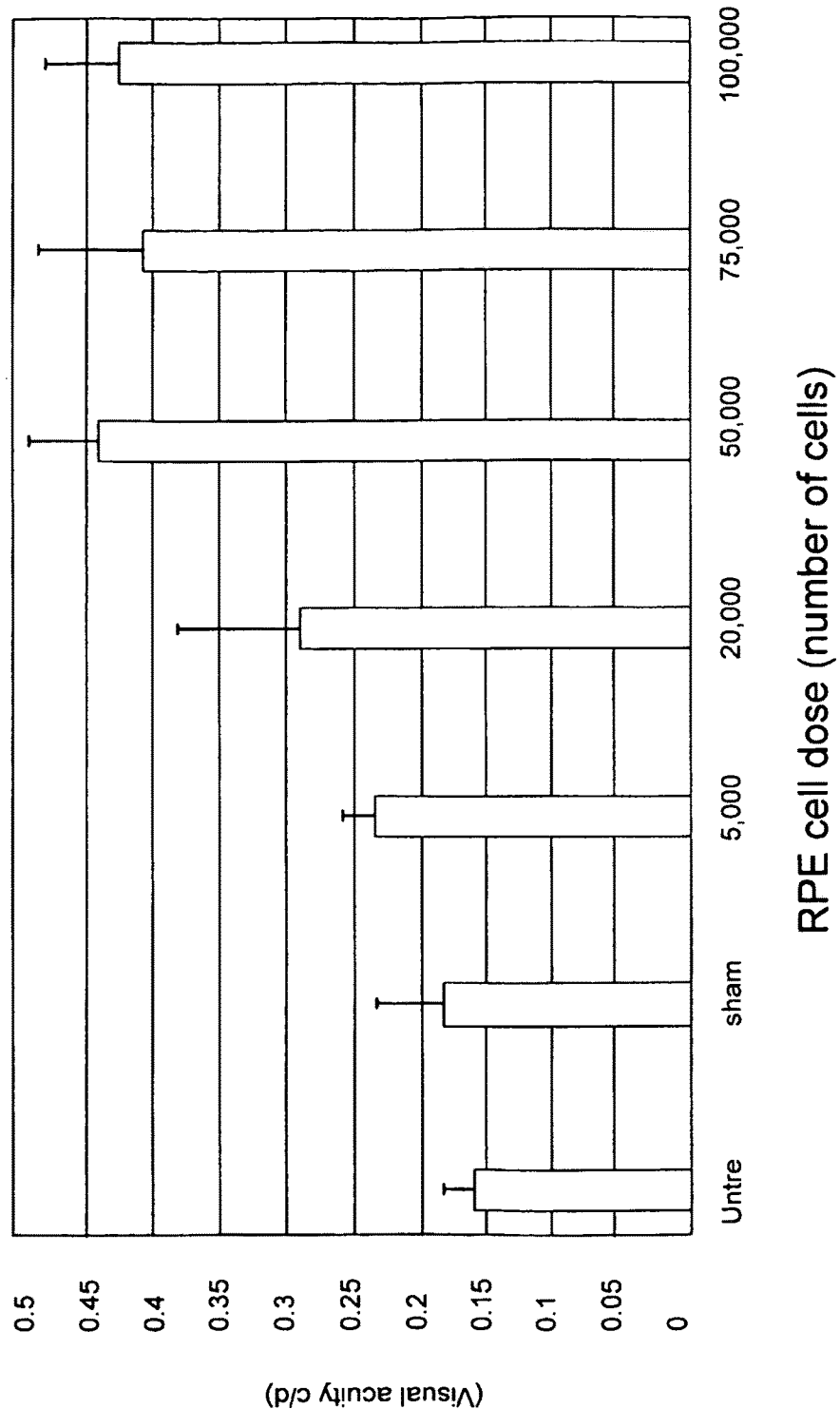

A

Age: P98

Right eye: cell graft   Left eye: untreated

Thresholds (Log units)

|     | 1.9 | 1.7 | 2.0 |     | 4.0 | 4.0 | 3.9 | 4.1 |
| --- | --- | --- | --- | --- | --- | --- | --- | --- |
| 1.4 | 1.2 | 1.0 | 1.6 |     | 3.9 | 3.5 | 3.7 | 3.8 |
| 1.6 | 1.1 | 0.8 | 0.9 |     | 3.6 | 2.3 | 3.2 | 3.4 |
| 1.3 | 0.9 | 0.7 | 1.0 |     | 3.0 | 3.1 | 2.9 | 3.3 |

B

Age: P187

Right eye: cell graft   Left eye: untreated

Thresholds (Log units)

|     | 2.6 | 2.4 | 2.5 |     | NR  | NR  | NR  | NR  |
| --- | --- | --- | --- | --- | --- | --- | --- | --- |
| 2.1 | 1.9 | 2.1 | 1.6 |     | NR  | NR  | NR  | NR  |
| 2.4 | 1.6 | 1.4 | 1.9 |     | 4.1 | 4.4 | 4.6 | NR  |
| 2.1 | 1.3 | 1.0 | 1.2 |     | 4.6 | 4.7 | 4.8 | NR  |

FIGURE 18

METHODS OF PRODUCING HUMAN RPE CELLS AND PHARMACEUTICAL PREPARATIONS OF HUMAN RPE CELLS

CROSS-REFERENCE TO RELATED PATENT APPLICATIONS

This application is a national stage of International Patent Application No. PCT/US2010/057056 which claims priority to U.S. Provisional Patent Application No. 61/262,002, filed Nov. 17, 2009, the disclosure of each of which is herein incorporated by reference.

BACKGROUND OF THE INVENTION

Retinal Pigment Epithelium (RPE)

The retinal pigment epithelium (RPE) is the pigmented cell layer outside the neurosensory retina between the underlying choroid (the layer of blood vessels behind the retina) and overlying retinal visual cells (e.g., photoreceptors—rods and cones). The RPE is critical to the function and health of photoreceptors and the retina. The RPE maintains photoreceptor function by recycling photopigments, delivering, metabolizing, and storing vitamin A, phagocytosing rod photoreceptor outer segments, transporting iron and small molecules between the retina and choroid, maintaining Bruch's membrane and absorbing stray light to allow better image resolution. Engelmann and Valtink (2004) "RPE Cell Cultivation." *Graefe's Archive for Clinical and Experimental Ophthalmology* 242(1): 65-67; See also Irina Klimanskaya, *Retinal Pigment Epithelium Derived From Embryonic Stem Cells*, in STEM CELL ANTHOLOGY 335-346 (Bruce Carlson ed., 2009).

Mature RPE is characterized by its cobblestone cellular morphology of black pigmented cells and RPE cell markers including cellular retinaldehyde-binding protein (CRALBP), a 36-kD cytoplasmic retinaldehyde-binding protein that is also found in apical microvilli (Eisenfeld, et al. (1985) *Experimental Research* 41(3): 299-304); RPE65, a 65 kD cytoplasmic protein involved in retinoid metabolism (Ma, et al. (2001) *Invest Opthalmol Vis Sci.* 42(7): 1429-35; Redmond (2009) *Exp Eye Res.* 88(5): 846-847); bestrophin, a membrane localized 68 kD product of the Best vitelliform macular dystrophy gene (VMD2) (Marmorstein, et al. (2000) *PNAS* 97(23): 12758-12763), and pigment epithelium derived factor (PEDF), a 48-kD secreted protein with angiostatic properties (Karakousis, et al. (2001) *Molecular Vision* 7: 154-163; Jablonski, et al. (2000) *The Journal of Neuroscience* 20(19): 7149-7157).

Degeneration of the RPE can cause retinal detachment, retinal dysplasia, or retinal atrophy that is associated with a number of vision-altering ailments that result in photoreceptor damage and blindness, such as, choroideremia, diabetic retinopathy, macular degeneration (including age-related macular degeneration), retinitis pigmentosa, and Stargardt's Disease (fundus flavimaculatus). WO 2009/051671.

Choroideremia

Choroideremia is an X-linked recessive retinal degenerative disease that leads to the degeneration of the choriocapillaris, the retinal pigment epithelium, and the photoreceptor of the eye. Mutations in the CHM gene, which encodes the Rab escort protein-1 (REP-1), cause choroideremia. REP-1 attaches to Rab proteins (involved in intracellular trafficking) and directs the Rab proteins to the organelle membranes. Mutant REP-1 proteins cannot escort Rab proteins, leading to a lack of functional Rab proteins. This lack of Rab proteins causes a disruption in intracellular trafficking and leads to necrosis in the RPE. In childhood, night blindness is a common first symptom. As the disease progresses, the patient suffers from a loss of vision, frequently starting as an irregular ring that gradually expands both in toward central vision and out toward the peripheral vision. Genetics Home Reference (U.S. National Library of Medicine) [Oct. 17, 2010]. Currently, no treatment is available and a need exists for a therapy for choroideremia.

Diabetic Retinopathy

Diabetic retinopathy is the most common diabetic eye disease and a leading cause of blindness in the United States. Diabetic retinopathy is caused by changes in the blood vessels of the retina and occurs in four stages. First, microaneurysms occur in the retinal blood vessels (Mild Nonproliferative Retinopathy). As the disease progresses, blood vessels become blocked leading to Moderate Nonproliferative Retinopathy. As more blood vessels are blocked this deprives several areas of the retina of their blood supply (Severe Nonproliferative Retinopathy.) Finally, signals sent by the retina for nourishment trigger the growth of new blood vessels (proliferative retinopathy) but these new blood vessels are abnormal and fragile. The new abnormal blood vessels grow along the retina and along the surface of the vitreous humour inside of the eye. As the structural integrity of the blood vessels deteriorate (in part due to changes in osmolarity due to insulin/sugar imbalance fundamental to diabetes), they leak blood, causing severe vision loss and even blindness. "Diabetic Retinopathy" (MayoClinic.org) [Feb. 11, 2010]. Generally, diabetic retinopathy may only be controlled or slowed with surgery but not treated, and the patient usually continues to suffer from vision problems. Therefore, there exists a need for improved diabetic retinopathy therapies.

Macular Degeneration

Age-related macular degeneration (AMD) is the most common reason for legal blindness in the United States and Europe. Atrophy of the submacular RPE and the development of choroidal neovascularizations (CNV) results secondarily in loss of central visual acuity. Early signs of AMD are deposits (druses) between retinal pigment epithelium and Bruch's membrane. Central geographic atrophy ("dry AMD") results from atrophy to the retinal pigment epithelial layer below the retina, which causes vision loss through loss of photoreceptors (rods and cones) in the central part of the eye. Neovascular or exudative AMD ("wet AMD") causes vision loss due to abnormal blood vessel growth (choroidal neovascularization) in the choriocapillaris, through Bruch's membrane, ultimately leading to blood and protein leakage below the macula. Bleeding, leaking, and scarring from these blood vessels eventually cause irreversible damage to the photoreceptors and rapid vision loss if left untreated. Current treatments for macular degeneration include anti-angiogenic therapy with ranibizumab (LUCENTIS®) or bevacizumab (AVASTIN®), photocoagulation (laser surgery), photodynamic therapy with verteporfin (VISUDYNE®), and submacular hemorrhage displacement surgery. "Macular Degeneration." (MayoClinic.org) [October 2010]. However, the goal of these therapies is to stem further vision loss and, unfortunately, existing damage cannot be reversed. Therefore, a great need exists for the treatment of macular degeneration.

Retinitis Pigmentosa (RP)

Retinitis pigmentosa (RP) is a group of inherited diseases that damage the photoreceptors (e.g., rods and cones) in the retina affecting approximately 1.5 million people worldwide. For example, autosomal recessive RP is caused by mutations in cis retinaldehyde binding protein or RPE65. The progression of RP is slow and varies from patient to patient. Patients with RP all suffer some vision loss, with night blindness as a typical early symptom followed by tunnel vision, and some may lose all sight. "Retinitis Pigmentosa." American Optometric Association (October 2010). Although treatment with vitamin A and lutein has shown some promise in slowing the progress of RP, no effective treatment is available.

Retinal Detachment

Retinal detachment, including rhegmatogenous retinal detachment, exudative, serous, or secondary retinal detachment, and tractional retinal detachment, is a disorder of the eye in which the retina peels away from its underlying layer of support tissue. Initial detachment may be localized, but without rapid treatment the entire retina may detach, leading to vision loss and blindness. See Ghazi and Green (2002) *Eye* 16: 411-421. A minority of retinal detachments arise from trauma including blunt blows to the orbit, penetrating trauma, and concussions. The current treatment is emergency eye surgery but only has an approximately 85% success rate, and even if successful, the patient may suffer a loss of visual acuity and visual artifacts. See Facts About Retinal Detachment [NEI Health Information] (October 2010). Therefore, a need exists for a treatment for retinal detachment.

Stargardt's Disease (Fundus Flavimaculatus)

Stargardt's Disease (fundus flavimaculatus) is a type of macular degeneration, including both an autosomal recessive and a dominant form, that causes a progressive loss of central vision of both eyes, but does not affect peripheral vision. Patients with Stargardt's experience a gradual deterioration of the retina's cone receptor cells. Cones are concentrated in the macula, and are responsible for central vision and color. Over time, these diseased cells cause a blackened hole to form in the central vision, and the ability to perceive colors is eventually affected. See Gass and Hummer (1999) *Retina* 19(4): 297-301 and Aaberg (1986) *Tr. Am. Ophth. Soc.* LXXXIV: 453-487. Currently, there are no treatments available for Stargardt's Disease.

RPE Cells in Medicine

Given the importance of the RPE in maintaining visual and retinal health, the RPE and methodologies for producing RPE cells in vitro are of considerable interest. See Lund, et al. (2001) *Progress in Retinal and Eye Research* 20(4): 415-449. For example, a study reported in Gouras, et al. (2002) *Investigative Ophthalmology & Visual Science* 43(10): 3307-311 describes the transplantation of RPE cells from normal mice into transgenic RPE65$^{-/-}$ mice (a mouse model of retinal degeneration). Gouras discloses that the transplantation of healthy RPE cells slowed the retinal degeneration in the RPE65$^{-/-}$ mice but after 3.7 weeks, its salubrious effect began to diminish. Treumer, et al. (2007) *Br J Opthalmol* 91: 349-353 describes the successfully transplantation of autologous RPE-choroid sheet after removal of a subfoveal choroidal neovascularization (CNV) in patients with age related macular degeneration (AMD), but this procedure only resulted in a moderate increase in mean visual acuity.

Moreover, RPE cells have been suggested as a possible therapy for treating Parkinson's disease, a chronic degenerative disease of the brain. The disease is caused by degeneration of specialized neuronal cells in the region of the basal ganglia. The death of dopaminergic neurons results in reduced synthesis of dopamine, an important neurotransmitter, in patients with Parkinson's disease. The standard therapy is medical therapy with L-dopa. L-dopa is metabolized in the basal ganglia to dopamine and there takes over the function of the missing endogenous neurotransmitter. See McKay, et al. (2006) *Exp Neurol.* 20(1): 234-243 and NINDS Parkinson's Disease Information Page (Sep. 23, 2009). However, L-dopa therapy loses its activity after some years, and thus, a new therapy for Parkinson's disease is needed. For example, Ming and Le (2007) *Chinese Medical Journal* 120(5): 416-420 suggests the transplantation of RPE cells from eye donors into the striatum of Parkinson's patients to supply beneficial neurotrophic and anti-inflammatory cytokines to treat Parkinson's' disease.

However, RPE cells sourced from human donors has several intractable problems. First, is the shortage of eye donors, and the current need is beyond what could be met by donated eye tissue. For example, RPE cells sourced from human donors are an inherently limited pool of available tissue that prevent it from scaling up for widespread use. Second, the RPE cells from human donors may be contaminated with pathogens and may have genetic defects. Third, donated RPE cells are derived from cadavers. The cadaver-sourced RPE cells have an additional problem of age where the RPE cells are may be close to senesce (e.g., shorter telomeres) and thus have a limited useful lifespan following transplantation. Reliance on RPE cells derived from fetal tissue does not solve this problem because these cells have shown a very low proliferative potential. Further, fetal cells vary widely from batch to batch and must be characterized for safety before transplantation. See, e.g., Irina Klimanskaya, *Retinal Pigment Epithelium Derived From Embryonic Stem Cells*, in STEM CELL ANTHOLOGY 335-346 (Bruce Carlson ed., 2009). Any human sourced tissue may also have problems with tissue compatibility leading to immunological response (graft-rejection). Also, cadaver-sourced RPE cells may not be of sufficient quality as to be useful in transplantation (e.g., the cells may not be stable or functional). Fourth, sourcing RPE cells from human donors may incur donor consent problems and must pass regulatory obstacles, complicating the harvesting and use of RPE cells for therapy. Fifth, a fundamental limitation is that the RPE cells transplanted in an autologous transplantation carry the same genetic information that may have lead to the development of AMD. See, e.g., Binder, et al. (2007) *Progress in Retinal and Eye Research* 26(5): 516-554. Sixth, the RPE cells used in autologous transplantation are already cells that are close to senesce, as AMD may develop in older patients. Thus, a shorter useful lifespan of the RPE cells limits their utility in therapeutic applications (e.g., the RPE cells may not transplant well and are less likely to last long enough for more complete recovery of vision). Seventh, to be successful in long-term therapies, the transplanted RPE cells must integrate into the RPE layer and communicate with the choroid and photoreceptors. Eighth, in AMD patients and elderly patients also suffer from degeneration of the Bruch's membrane, complicating RPE cell transplantation. See Gullapalli, et al. (2005) *Exp Eye Res.* 80(2): 235-48. Thus there exists a great need for a source of RPE cells for therapeutic uses.

Embryonic Stem Cells Derived RPE Cells (hESC-RPE Cells)

Human embryonic stem cells (hES) are considered a promising source of replacement RPE cells for clinical use. See Idelson, et al. (2009) *Cell Stem Cell* 5: 396-408. However, numerous problems continue to plague their use as therapeutics, including the risk of teratoma-formation and the need for powerful immunosuppressive drugs to overcome the problems with immune rejection. For example, Wang, et al. (2010) Transplantation describes a study where mouse embryonic stem cells were differentiated into RPE cells and then transplanted into a mouse model of retinitis pigmentosa ($Rpe65^{rd12}/Rpe^{rd12}$ C57BL6 mice). Although the $Rpe65^{rd12}/Rpe^{rd12}$ mice receiving the RPE cell transplants did show significant visual recovery during a 7-month period, this was complicated by retinal detachments and tumors.

Further, the transition from basic research to clinical application is precluded by the need to adhere to guidelines set forth by the U.S. Food and Drug Administration, collectively referred to as current Good Manufacturing Practices (GMP) and current Good Tissue Practices (GTP). In the context of clinical manufacturing of a cell therapy product, such as hES cell-derived RPE, GTP governs donor consent, traceability, and infectious disease screening, whereas the GMP is relevant to the facility, processes, testing, and practices to produce a consistently safe and effective product for human use. Lu, et al. Stem Cells 27: 2126-2135 (2009). Thus, there exists a need for a systematic, directed manner for the production of large numbers of RPE cells suitable for use in transplantation therapies.

SUMMARY OF THE INVENTION

The present invention provides methods for differentiating RPE cells from pluripotent stem cells. The present invention also provides functional retinal pigmented epithelial cells (RPE) that are terminally differentiated from pluripotent stem cells. These methods may be used to produce large numbers of functional differentiated RPE cells for use in therapeutic methods (and uses), screening assays, and to study the basic biology of the RPE. The present invention also provides preparations including pharmaceutical preparations of RPE cells derived from pluripotent stem cells.

In one embodiment, the invention provides a method of producing a substantially purified culture of retinal pigment epithelial (RPE) cells comprising
  (a) providing pluripotent stem cells;
  (b) culturing the pluripotent stem cells to form embryoid bodies in nutrient rich, low protein medium;
  (c) culturing the embryoid bodies to form an adherent culture in nutrient rich, low protein medium;
  (d) culturing the cells of (c) in medium capable of supporting growth of high-density somatic cell culture, whereby RPE cells appear in the culture of cells;
  (e) dissociating the culture of (d);
  (f) selecting the RPE cells from the culture and transferring the RPE cells to a separate culture containing medium supplemented with a growth factor to produce an enriched culture of RPE cells; and
  (g) propagating the enriched culture of RPE cells to produce a substantially purified culture of RPE cells.

In another embodiment, the invention provides a method of producing a substantially pure culture of mature retinal pigment epithelial (RPE) cells comprising
  (a) providing pluripotent stem cells;
  (b) culturing the pluripotent stem cells to form embryoid bodies in nutrient rich, low protein medium;
  (c) culturing the embryoid bodies to form an adherent culture in nutrient rich, low protein medium;
  (d) culturing the cells of (c) in medium capable of supporting growth of high-density somatic cell culture, whereby RPE cells appear in the culture of cells;
  (e) dissociating the culture of (d);
  (f) selecting the RPE cells from the culture and transferring the RPE cells to a separate culture containing medium supplemented with a growth factor to produce an enriched culture of RPE cells;
  (g) propagating the enriched culture of RPE cells; and
  (h) culturing the enriched culture of RPE cells to produce mature RPE cells.

In one embodiment, the pluripotent stem cells are embryonic stem cells, induced pluripotent stem (iPS) cells, adult stem cells, hematopoietic cells, fetal stem cells, mesenchymal stem cells, postpartum stem cells, multipotent stem cells, or embryonic germ cells. In another embodiment, the pluripotent stem cells may be mammalian pluripotent stem cells. In still another embodiment, the pluripotent stem cells may be human pluripotent stem cells including but not limited to human embryonic stem (hES) cells, human induced pluripotent stem (iPS) cells, human adult stem cells, human hematopoietic stem cells, human fetal stem cells, human mesenchymal stem cells, human postpartum stem cells, human multipotent stem cells, or human embryonic germ cells. In another embodiment, the pluripotent stem cells may be a hES cell line listed in the European Human Embryonic Stem Cell Registry—hESCreg.

In one embodiment, the present invention provides preparations of RPE cells, including substantially purified preparations of RPE cells. Exemplary RPE cells may be differentiated from pluripotent stem cells, such as embryonic stem cells, iPS cells, blastomeres, inner mass cells, or oocytes which may be parthenogenetically activated. These pluripotent stem cells may be recombinant or genetically engineered (e.g., engineered to express a desired therapeutic protein or to eliminate the expression of a gene involved in a genetic deficiency such as macular degeneration.) The RPE cells may be formulated and used to treat retinal degenerative diseases. Additionally, pluripotent stem cell-derived RPE cells can be used in screening assays to identify agents that modulate RPE cell survival (in vitro and/or in vivo), to study RPE cell maturation, or to identify agents that modulate RPE cell maturation. Agents identified using such screening assays may be used in vitro or in vivo and may provide additional therapeutics that can be used alone or in combination with RPE cells to treat retinal degenerative diseases.

In one embodiment, the pluripotent stem cells of (a) may be genetically engineered.

In one embodiment, the medium of (a), (b), (c), (d), (f), (g), or (h) contains serum free B-27 supplement. In another embodiment, the medium of (a), (b), (c), (d), (I), (g), or (h) does not contain serum free B-27 supplement.

In one embodiment, the cells of (b) are cultured for at least about 7-14 days. In another embodiment, the cells of (c) are cultured for at least about 7-10 days. In a further embodiment, cells of (e) are cultured for at least about 14-21 days.

In one embodiment, the medium of (a), (b), (c), (d), (f), (g), or (h) is MDBK-GM, OptiPro SFM, VP-SFM, EGM-2, or MDBK-MM. In another embodiment, the growth factor of (f) is EGF, bFGF, VEGF, or recombinant insulin-like growth factor. In a further embodiment, the medium (g) comprises heparin, hydrocortisone, or ascorbic acid. In yet another embodiment, the culture medium used for propagating the enriched culture of RPE cells does not support the growth or maintenance of undifferentiated pluripotent stem cells.

In one embodiment, step (e) comprises contacting the culture with an enzyme selected from the group consisting of trypsin, collagenase, dispase, papain, mixture of collagenase and dispase, and a mixture of collagenase and trypsin. In another embodiment, step (e) comprises mechanical disruption.

In one embodiment, the pluripotent stem cells have reduced HLA antigen complexity.

In one embodiment, the method further comprising culturing said RPE cells under conditions that increase alpha integrin subunit expression, wherein said alpha integrin subunits are 1-6 or 9. In another embodiment, the conditions comprising exposure to manganese, exposure to an antibody to CD29, or passaging said RPE cells for at least about 4 passages. In a further embodiment, the anti-CD29 antibody is monoclonal antibody HUTS-21 or monoclonal antibody (mAb) TS2/16.

In one embodiment, the invention provides a pharmaceutical preparation of RPE cells suitable for treatment of retinal degradation, wherein said RPE cells have at least one of the following properties:
  (a) maintain their phenotype after transplantation for at least about one month,
  (b) maintain their phenotype in culture for at least about one month,
  (c) integrate into the host after transplantation,
  (d) do not substantially proliferate after transplantation,
  (e) are phagocytositic,
  (f) deliver, metabolize, or store vitamin A,
  (g) transport iron between the retina and choroid after transplantation,
  (h) attach to the Bruch's membrane after transplantation,
  (i) absorb stray light after transplantation,
  (j) have elevated expression of alpha integrin subunits, or
  (k) have longer telomeres than RPE cells derived from human donors.
In another embodiment, the RPE cells have at least 1, 2, 3, 4, 5, or 6 of the recited properties. In yet another embodiment, the RPE cells are phagocytositic and have longer telomeres than RPE cells derived from human donors.

In one embodiment, the invention provides a pharmaceutical preparation for use in treating retinal degeneration comprising an effective amount of RPE cells. In another embodiment, the retinal degeneration is due to Stargardt's disease, age-related macular degeneration (AMD), choroideremia, retinitis pigmentosa, retinal detachment, retinal dysplasia, or retinal atrophy.

In one embodiment, the pharmaceutical preparation of RPE cells is formulated for transplantation in the form of a suspension, gel, or colloid. In another embodiment, the preparation is formulated for transplantation with a matrix, substrate, scaffold, or graft. In a further embodiment, the preparation is formulated for administration to the subretinal space of the eye. In a further embodiment, the preparation comprises at least about $10^3$-$10^9$ RPE cells.

In one embodiment, the RPE cell preparation comprises mature RPE cells. In another embodiment, the RPE cell preparation consist essentially of mature RPE cells. In a further embodiment, the preparation comprises at least about 75% RPE cells.

In one embodiment, the preparation is substantially free of viral, bacterial, and/or fungal contamination. In another embodiment, the preparation is formulated in a pharmaceutically acceptable carrier. In a further embodiment, the preparation is formulated for administration to the eye. In a still further, the preparation is formulated for administration to the sub-retinal space. In another embodiment, the RPE cells are functional RPE cells capable of integrating into the retina upon transplantation. In another embodiment, the preparation is substantially free of mouse embryo fibroblasts (MEF) and human embryonic stem cells (hES). In a further embodiment, the preparation is Good Manufacturing Practices (GMP) compliant.

In one embodiment, the invention provides a cryopreserved preparation comprising at least about $10^4$ human RPE cells, wherein the preparation is a substantially purified preparation of human RPE cells derived from human pluripotent stem cells, and wherein the RPE cells express RPE-65, Bestrophin, PEDF, CRALBP, Otx2, and Mit-F. In another embodiment, at least about 85% of the RPE cells retain viability following thawing.

In one embodiment, the invention provides a substantially purified preparation of human RPE cells differentiated from human pluripotent stem cells, wherein the RPE cells express, at the mRNA and protein level, RPE-65, Bestrophin, PEDF, CRALBP, Otx2, and Mit-F, and wherein the cells substantially lack expression of Oct-4, NANOG, and Rex-1. In another embodiment, the RPE cells comprise differentiated RPE cells and mature differentiated RPE cells, and wherein at least the mature differentiated RPE cells further express, at the mRNA and protein level, PAX2, pax-6, and tyrosinase. In another embodiment, the RPE cells are differentiated from human ES cells or human IPS cells.

In one embodiment, the invention provides for the use of a pharmaceutical preparation of RPE cells in the manufacture of a medicament for the treatment of retinal degeneration.

In one embodiment, the invention provides a method of cryopreserving RPE cells comprising
  (a) culturing RPE cells,
  (b) harvesting said RPE cells,
  (c) centrifuging said RPE cells, and
  (d) resuspending said RPE cells in 10% DMSO/90% FBS solution.

In one embodiment, the RPE cells are washed with $Ca^{2+}/Mg^+$ DPBS. In another embodiment, the RPE cells were cultured until bestrophin is organized at the cell membrane. In another embodiment, the RPE cells are cultured until they reach a medium pigmentation level. In another embodiment, step (a) comprising culturing at least two culture vessels of RPE cells. In another embodiment, the RPE cells are harvested and combined into a single lot. In another embodiment, the RPE cells are harvested and stored in FBS during the combination of RPE cells.

In one embodiment, the invention provides a method of treating retinal degeneration comprising a pharmaceutical preparation comprising administering an effective amount of RPE cells described herein. In another embodiment, the retinal degeneration is due to choroideremia, diabetic retinopathy, age-related macular degeneration, retinal detachment, retinitis pigmentosa, or Stargardt's Disease.

In one embodiment, the preparation is transplanted in a suspension, matrix, gel, colloid, scaffold, or substrate. In another embodiment, the preparation is administered by injection into the subretinal space of the eye.

In a further embodiment, the effective amount is at least about 20,000-200,000 RPE cells. In another embodiment, the effective amount is at least about 20,000, 50,000, 75,000, 100,000, 125,000, 150,000, 175,000, 180,000, 185,000, 190,000, or 200,000 RPE cells.

In one embodiment, the method further comprising monitoring the efficacy of the method by measuring electroretinogram responses, optomotor acuity threshold, or luminance threshold in the subject.

In one embodiment, the preparation is substantially free of viral, bacterial, or fungal contamination. In another embodiment, the RPE cells are functional RPE cells capable of integrating into the retina upon transplantation. In a further embodiment, the RPE cells improve visual acuity following transplantation.

The present invention provides methods for the treatment of eye disorders. In particular, these methods involve the use of RPE cells to treat or ameliorate the symptoms of eye disorders, particularly eye disorders caused or exacerbated, in whole or in part, by damage to or breakdown of the endogenous RPE layer (e.g., retinal degeneration).

In one embodiment, the RPE cells described herein are substantially free of genetic mutations that may lead to retinal degeneration.

In one embodiment, the RPE cells may be transplanted with a biocompatible polymer such as polylactic acid, poly (lactic-co-glycolic acid), 50:50 PDLGA, 85:15 PDLGA, and INION GTR® biodegradable membrane (mixture of biocompatible polymers).

In another embodiment, the RPE cells adhere to Bruch's membrane after transplantation, establish polarity, and integrate into the receipt's tissue.

In one embodiment, the RPE cells may improve visual acuity after transplantation. In another embodiment, the RPE cells may substantially improve visual acuity after transplantation.

In one embodiment, the RPE cells may be in compliance with at least one of the GTP and/or GMP Regulations as presented in Table 3 or 4. In another embodiment, the RPE cells may be produced in accordance with Good Manufacturing Practice (GMP). In a further embodiment, the RPE cells may be produced in accordance with Good Tissue Practice (GTP). In a further embodiment, the RPE cells may meet at least one of the criteria recited in Table 4. In a still further embodiment, the RPE cells may meet at least 1, 2, 3, 4, or 5 of the criteria recited in Table 4.

In one embodiment, the RPE cells lack substantial expression of embryonic stem cell markers including but not limited to Oct-4, NANOG, Rex-1, alkaline phosphatase, Sox2, TDGF-1, DPPA-2, and DPPA-4. In another embodiment, the RPE cells express RPE cell markers including but not limited to RPE65, CRALBP, PEDF, Bestrophin, MitF, Otx2, PAX2, Pax-6, and tyrosinase. In a further embodiment, the RPE cells express at least one of the genes listed in Table 5, and wherein expression of the at least one gene is increased in the RPE cells relative to expression in human ES cells. In a still further embodiment, the RPE cells express at least one of the genes listed in Table 6, and wherein expression of the at least one gene is decreased in the RPE cells relative to expression in human ES cells. In one embodiment, the RPE cells show increased alpha integrin subunit expression. In another embodiment, the alpha integrin subunit is alpha 1, 2, 3, 4, 5, 6, or 9. In yet another embodiment, the expression is mRNA expression, protein expression, or both mRNA and protein expression.

The present invention provides for a method of providing a RPE preparation to a clinical site comprising (a) thawing vials of cryopreserved RPE cells, (b) resuspending the RPE cells in media, (c) centrifuging the RPE cells, (d) resuspending the RPE cells in media, (e) aliqouting the RPE cells into vials, and (f) transferring to the clinical site. In one embodiment, the resuspension and centrifugation steps may be repeated at least 1, 2, 3, 4, or 5 times. In another embodiment, the RPE product is transported to the clinical site within at least about 1, 2, 3, 4, 5, 6, 7, 8, 9, or 10 hours of completion of step (e). In a further embodiment, the vials may be labeled.

The present invention also provides a method for a providing RPE cell preparation for sale comprising (a) producing RPE cells and (b) preparing said RPE cell preparations for transfer to a customer. In one embodiment, the method may comprise cryopreserving the RPE cells. In another embodiment, the method comprises offering said RPE cell preparations for sale. In a further embodiment, the method comprises advertising the RPE cell preparations.

The invention contemplates any combination of the aspects and embodiments described above or below. For example, preparations of RPE cells comprising any combination of differentiated RPE cells and mature RPE cells can be used in the treatment of any of the conditions described herein. Similarly, methods described herein for producing RPE cells using human embryonic stem cells as a starting material may be similarly performed using any human pluripotent stem as a starting material.

BRIEF DESCRIPTION OF THE DRAWINGS

FIG. 1 Production of RPE Cells: Step 1—Preparation of MEF Feeder Cells. The MEF feeder cells may be cultured in the presence of about 10-20 nm/mL human leukemia inhibitory factor (LW) and about 8-16 ng/mL human bFGF. See, e.g., Irina Klimanskaya, *Retinal Pigment. Epithelium Derived From Embryonic Stem Cells*, in STEM CELL ANTHOLOGY 335-346 (Bruce Carlson ed., 2009).

FIG. 2 Production of RPE Cells: Step 2—Seeding and Expansion of hES Cells.

FIG. 3 Production of RPE Cells: Step 3—Embryoid Body Formation.

FIG. 4 Production of RPE Cells: Step 4—RPE Derivation. Clusters of RPE cells may appear within 6-8 weeks, where RPE cells may appear on the surface of the embryoid bodies and then slowly spread to the entire embryoid body over time.

FIG. 5 Production of RPE Cells: Step 5—RPE Expansion and Differentiation. In one embodiment, the RPE cell cultures may be washed at least 1, 2, 3, 4, or 5 times to remove loose or isolated cells. The inventors found that this surprisingly improved the yield of RPE cells. The RPE cells may be characterized by the expression of RPE-specific cell markers such as CRALBP, bestrophin, RPE65, and PEDF. The RPE cells may also be characterized by functional tests including a RPE-specific phagocytosis assay and vitamin A metabolism assay. See, e.g., Irina Klimanskaya, Retinal Pigment Epithelium Derived From Embryonic Stein Cells, in STEM CELL ANTHOLOGY 335-346 (Bruce Carlson ed., 2009).

FIG. 6 Production of RPE Cells: Step 6—Harvest, Culturing, and Cryopreservation. In one embodiment, several flasks of RPE cells may be seeded and propagated to yield a large amount of RPE cells. As individual flasks of RPE cells are harvested (e.g., T-75 flasks), the RPE cells may be stored in FBS at about 4° C. during the harvesting steps. Additionally, the RPE cells may be considered ready for cryopreservation when the dystrophin is organized at the cell membrane and the PAX6 expression is low. The inventors found that this surprisingly improved the viability of the cryopreserved RPE cells.

FIG. 7 Production of RPE Cells: Step 7—Thawing of Cryopreserved RPE cells and Pharmaceutical Preparation.

FIG. 18 two examples of luminance threshold maps from mice receiving a 100,000 RPE cell dose with medium pigmentation. The luminance thresholds show serious deterioration on the untreated side, with more than one half the area being nonresponsive at P187 compared with P98, whereas responsiveness is still sensitive on the cell-injected side, although some reduction in thresholds has occurred (0.7 log units at P98 vs. 1.0 log units at P187).

Figure 1:
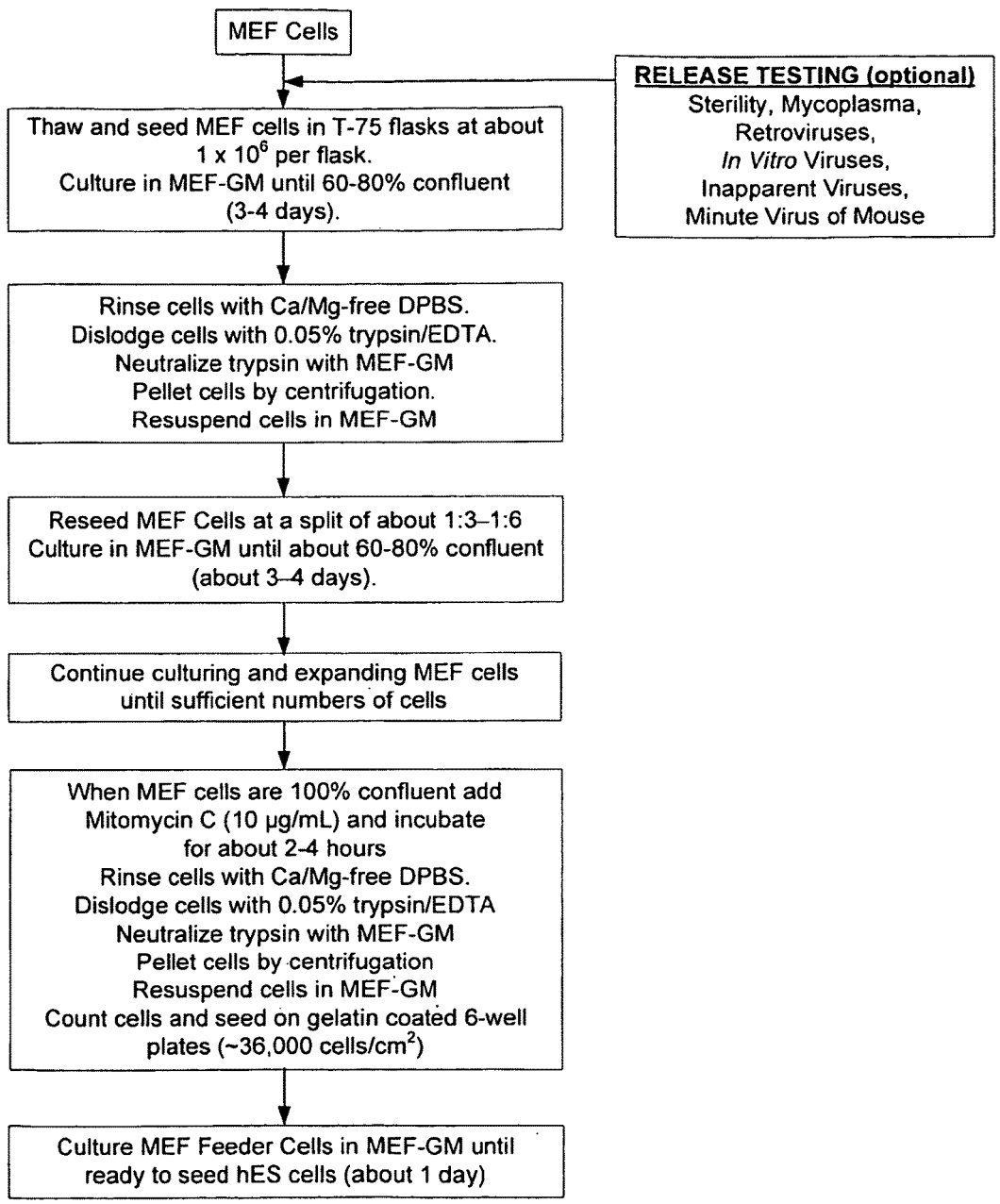
FIGS. 1-7 depict exemplary protocols for the production of RPE cells.

DETAILED DESCRIPTION OF THE INVENTION in order that the invention herein described may be fully understood, the following detailed description is set forth. Various embodiments of the invention are described in detail and may be further illustrated by the provided examples.

Definitions

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

In order to further define the invention, the following terms and definitions are provided herein.

As used in the description herein and throughout the claims that follow, the meaning of "a," "an," and "the" includes plural reference unless the context clearly dictates otherwise.

"Effective amount," as used herein, refers broadly to the amount of a compound or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and preexisting conditions, of the patient to be treated. The term "effective amount" is synonymous with "therapeutically effective amount" for purposes of this invention.

"Embryo" or "embryonic," as used herein refers broadly to a developing cell mass that has not implanted into the uterine membrane of a maternal host. An "embryonic cell" is a cell isolated from or contained in an embryo. This also includes blastomeres, obtained as early as the two-cell stage, and aggregated blastomeres.

"Embryonic stem cells" (ES cells), as used herein, refers broadly to cells derived from the inner cell mass of blastocysts or morulae that have been serially passaged as cell lines. The ES cells may be derived from fertilization of an egg cell with sperm or DNA, nuclear transfer, parthenogenesis, or by means to generate ES cells with homozygosity in the HLA region. ES cells may also refer to cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Embryonic stem cells, regardless of their source or the particular method used to produce them, can be identified based on the: (i) ability to differentiate into cells of all three germ layers, (ii) expression of at least Oct-4 and alkaline phosphatase, and (iii) ability to produce teratomas when transplanted into immunocompromised animals.

"Embryo-derived cells" (EDC), as used herein, refers broadly to morula-derived cells, blastocyst-derived cells including those of the inner cell mass, embryonic shield, or epiblast, or other pluripotent stem cells of the early embryo, including primitive endoderm, ectoderm, and mesoderm and their derivatives. "EDC" also including blastomeres and cell masses from aggregated single blastomeres or embryos from varying stages of development, but excludes human embryonic stem cells that have been passaged as cell lines.

"Macular degeneration," as used herein, refers broadly to diseases characterized by a progressive loss of central vision associated with abnormalities of Bruch's membrane, the neural retina, and the retinal pigment epithelium. Macular degeneration diseases include but are not limited to age-related macular degeneration, North Carolina macular dystrophy, Sorsby's fundus dystrophy, Stargardt's disease, pattern dystrophy, Best disease, malattia leventinese, Doyne's honeycomb choroiditis, dominant drusen, and radial drusen.

"Pluripotent stem cell," as used herein, refers broadly to a cell capable of prolonged or virtually indefinite proliferation in vitro while retaining their undifferentiated state, exhibiting normal karyotype (e.g., chromosomes), and having the capacity to differentiate into all three germ layers (i.e., ectoderm, mesoderm and endoderm) under the appropriate conditions.

"Pluripotent embryonic stem cells," as used herein, refers broadly cells that: (a) are capable of inducing teratomas when transplanted in immunodeficient (SCID) mice; (b) are capable of differentiating to cell types of all three germ layers (e.g., ectodermal, mesodermal, and endodermal cell types); and (c) express at least one molecular embryonic stem cell markers (e.g., express Oct 4, alkaline phosphatase, SSEA-3 surface antigen, SSEA-4 surface antigen, NANOG, TRA-1-60, TRA-1-81, SOX2, REX1).

"RPE cell," "differentiated RPE cell," "ES-derived RPE cell," and as used herein, may be used interchangeably throughout to refer broadly to an RPE cell differentiated from a pluripotent stem cell using a method of the invention. The term is used generically to refer to differentiated RPE cells, regardless of the level of maturity of the cells, and thus may encompass RPE cells of various levels of maturity. RPE cells can be visually recognized by their cobblestone morphology and the initial appearance of pigment. RPE cells can also be identified molecularly based on substantial lack of expression of embryonic stem cell markers such as Oct-4 and NANOG, as well as based on the expression of RPE markers such as RPE-65, PEDF, CRALBP, and bestrophin. Thus, unless otherwise specified, RPE cells, as used herein, refers to RPE cells differentiated in vitro from pluripotent stem cells.

"Mature RPE cell" and "mature differentiated RPE cell," as used herein, may be used interchangeably throughout to refer broadly to changes that occur following initial differentiating of RPE cells. Specifically, although RPE cells can be recognized, in part, based on initial appearance of pigment, after differentiation mature RPE cells can be recognized based on enhanced pigmentation.

"Pigmented," as used herein refers broadly to any level of pigmentation, for example, the pigmentation that initial occurs when RPE cells differentiate from ES cells. Pigmentation may vary with cell density and the maturity of the differentiated RPE cells. The pigmentation of a RPE cell may be the same as an average RPE cell after terminal differentiation of the RPE cell. The pigmentation of a RPE cell may be more pigmented than the average RPE cell after terminal differentiation of the RPE cell. The pigmentation of a RPE cell may be less pigmented than the average RPE cell after terminal differentiation.

"Signs" of disease, as used herein, refers broadly to any abnormality indicative of disease, discoverable on examination of the patient; an objective indication of disease, in contrast to a symptom, which is a subjective indication of disease.

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting or reducing the development of the disease or its clinical symptoms, and/or relieving the disease, causing regression of the disease or its clinical symptoms. Therapy encompasses prophylaxis, prevention, treatment, cure, remedy, reduction, alleviation, and/or providing relief from a disease, signs, and/or symptoms of a disease. Therapy encompasses an alleviation of signs and/or symptoms in patients with ongoing disease signs and/or symptoms (e.g., blindness, retinal deterioration.) Therapy also encompasses "prophylaxis" and "prevention". Prophylaxis includes preventing disease occurring subsequent to treatment of a disease in a patient or reducing the incidence or severity of the disease in a patient. The term "reduced", for purpose of therapy, refers broadly to the clinical significant reduction in signs and/or symptoms. Therapy includes treating relapses or recurrent signs and/or symptoms (e.g., retinal degeneration, loss of vision.) Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., blindness, retinal degeneration).

Retinal Pigment Epithelium (RPE) Cells

The present invention provides RPE cells that may be differentiated from pluripotent stem cells, such as human embryonic stem cells, and are molecularly distinct from embryonic stem cells, adult-derived RPE cells, and fetal-derived RPE cells. The inventors surprisingly discovered that the method by which the RPE cells are produced from a pluripotent stem cell is a critical factor in determining the structural and functional characteristics of the resulting RPE cells. The inventors found that the RPE cells produced by the methods described produced a different RPE cell product than previous methods and sources of RPE cells. For example, the manufacturing process steps described herein impart distinctive structural and functional characteristics to the final RPE cell product such that these cells closely resemble native RPE cells and are distinct from fetal derived RPE cells or RPE cell lines (e.g., APRE19). Further, the methods of producing RPE cells described herein are not permissive to ES cells. Thus, as ES cells cannot persist in the culture processes described herein, and they do not pose an unacceptable risk of contamination in the RPE cell cultures and preparations.

The cell types provided by this invention include, but are not limited to, RPE cells, RPE progenitor cells, iris pigmented epithelial (IPE) cells, and other vision associated neural cells, such as internuncial neurons (e.g., "relay" neurons of the inner nuclear layer (INL)) and amacrine cells. The invention also provides retinal cells, rods, cones, and corneal cells as well as cells providing the vasculature of the eye.

The RPE cells may be used for treating retinal degeneration diseases due to retinal detachment, retinal dysplasia, or retinal atrophy or associated with a number of vision-altering ailments that result in photoreceptor damage and blindness, such as, choroideremia, diabetic retinopathy, macular degeneration (e.g., age-related macular degeneration), retinitis pigmentosa, and Stargardt's Disease (fundus flavimaculatus).

The RPE cells may be stable, terminally differentiated RPE cells that do not de-differentiate to a non-RPE cell type. The RPE cells described herein may be functional RPE cells, characterized by the ability to integrate into the retina upon corneal, sub-retinal, or other administration into an animal.

In order to characterize developmental stages during the embryonic stem cell (ES) differentiation process into retinal pigmented epithelium (RPE), several assays were used to identify the expression levels of genes key to each representative stage of development. It was discovered that several genes were expressed at the mRNA and protein levels in RPE cells. The expression level of ES and RPE cell markers may be done at the mRNA by, for example, PCR (e.g., RT-PCT, quantitative PCR, real-time PCR) or Northern blotting, or at the protein level by, for example, Western blot, immunoblot, or other immunoassays.

The pluripotency of embryonic stem cells is maintained in part by the delicate reciprocal balance of the two transcription factors Oct4 (Pou5f1) and NANOG. During ES cell differentiation, the expression of these genes is downregulated, and recent evidence has suggested hypermethylation of the genes encoding these proteins to be responsible. Loss of the expression of either or both of these genes results in transcriptional activation of genes associated with cellular differentiation. For instance, it was discovered that PAX6 acts with PAX2 to terminally differentiate mature RPE cells via coordination of Mit-F and Otx2 to transcribe RPE-specific genes such as Tyrosinase (Tyr), and downstream targets such as RPE-65, Bestrophin, CRALBP, and PEDF.

The RPE cells may express RPE cell markers listed in Table 5. For example, the expression level of the RPE cell genes RPE65, PAX2, PAX6, and tyrosinase, bestrophin, PEDF, CRALBP, Otx2, and MitF may be equivalent to that in naturally occurring RPE cells. The level of maturity of the RPE cells may assessed by expression of at least one of PAX2, PAX6, and tyrosinase, or their respective expression levels.

In contrast, the RPE cells may not express. ES cell markers listed in Table 6. For example, the expression levels of the ES cell genes Oct-4, NANOG, and/or Rex-1 may be about 100-1000 fold lower in RPE cells than in ES cells. For example, the RPE cells may substantially lack expression of ES cell markers including but not limited to Octamer binding protein 4 (Oct-4, a.k.a., Pou5f1), stage specific embryonic antigens (SSEA)-3 and SSEA-4, tumor rejection antigen (TRA)-1-60, TRA-1-80, alkaline phosphatase, NANOG, and Rex-1. Thus, in comparison to ES cells, RPE cells are substantially lack expression of Oct-4, NANOG, and/or Rex-1.

The RPE cells described herein may also show elevated expression levels of alpha integrin subunits 1-6 or 9 as compared to uncultured RPE cells or other RPE cell preparations. The RPE cells described herein may also show elevated expression levels of alpha integrin subunits 1, 2, 3, 4, 5, or 9. The RPE cells described herein may be cultured under conditions that promote the expression of alpha integrin subunits 1-6. For example, the RPE cells may be cultured with integrin-activating agents including but not limited to manganese and the activating monoclonal antibody (mAb) TS2/16. See Afshari, et al. Brain (2010) 133(2): 448-464. The RPE cells may be plated on laminin (1 μg/mL) and exposed to $Mn^{2+}$ (500 μM) for at least about 8, 12, 24, 36, or 48 hours. Also, the RPE cells may be cultured for several passages (e.g., at least about 4, 5, 6, 7, or 8 passages) which increases alpha integrin subunit expression.

Table 1 describes some characteristics of the RPE cells that may be used to identify or characterize the RPE cells. In particular, the RPE cells may exhibit a normal karyotype, express RPE markers, and not express hES markers.

TABLE 1

Parameters of RPE cells

| Parameter | Specification for Representative Lot of RPE Cells |
| --- | --- |
| Karyotype | 46, XX Normal |
| Morphology at harvest | Normal cellular morphology, medium pigmentation |

TABLE 1-continued

Parameters of RPE cells

| Parameter | Specification for Representative Lot of RPE Cells |
|---|---|
| Post-thaw Viable Cell Count | ≥70% |
| qPCR Testing—<br>Presence of RPE Markers<br>Bestrophin<br>RPE-65<br>CRALBP<br>PEDF<br>PAX6<br>MITF | Present |
| qPCR Testing—<br>Absence of hES Markers<br>Oct-4<br>NANOG<br>Rex-1<br>Sox2 | Absent |
| Immunostaining—<br>Presence of RPE Markers<br>Bestrophin<br>CRALBP<br>PAX6<br>MITF<br>ZO-1 | Present |
| Immunostaining—<br>Absence of hES markers<br>Oct-4<br>Alkaline Phosphatase | Absent |

The distinct expression pattern of mRNA and proteins in the RPE cells of the invention constitutes a set of markers that separate these RPE cells from cells in the art, such as hES cells, ARPE-19 cells, and fetal RPE cells. Specifically, these cells are different in that they can be identified or characterized based on the expression or lack of expression, which may be assessed by mRNA or protein level, of at least one marker. For example, the RPE cells may be identified or characterized based on expression or lack of expression of at least one marker listed in Tables 5 or 6. See also Liao, et al. (2010) *Human Molecular Genetics* 19(21): 4229-38. The RPE cells may also be identified and characterized, as well as distinguished from other cells, based on their structural properties. Thus, the RPE cells described herein expressed multiple genes that were not expressed in hES cells, fetal RPE cells, or ARPE-19 cells. See WO 2009/051671; See also Dunn, et al. (1996) *Exp Eye Res.* 62(2): 155-169.

The RPE cells described herein may also be identified and characterized based on the degree of pigmentation of the cell. Pigmentation post-differentiation is not indicative of a change in the RPE state of the cells (e.g., the cells are still differentiated RPE cells). Rather, the changes in pigment post-differentiation correspond to the density at which the RPE cells are cultured and maintained. Mature RPE cells have increased pigmentation that accumulates after initial differentiation. For example, the RPE cells described herein may be mature RPE cells with increased pigmentation in comparison to differentiated RPE cells. Differentiated RPE cells that are rapidly dividing are lightly pigmented. However, when cell density reaches maximal capacity, or when RPE cells are specifically matured, RPE take on their characteristic phenotypic hexagonal shape and increase pigmentation level by accumulating melanin and lipofuscin. As such, initial accumulation of pigmentation serves as an indicator of RPE differentiation and increased pigmentation associated with cell density serves as an indicator of RPE maturity. For example, the RPE cells may be pigmented, to at least some extent. For example, the RPE cell may be derived from a human embryonic stem cell, which cell is pigmented and expresses at least one gene that is not expressed in a cell that is not a human retinal pigmented epithelial cell.

Mature RPE cells can be subcultured at a lower density, such that the pigmentation decreases. In this context, mature RPE cells may be cultured to produce RPE cells. Such RPE cells are still differentiated RPE cells that express markers of RPE differentiation. Thus, in contrast to the initial appearance of pigmentation that occurs when RPE cells begin to differentiate, pigmentation changes post-differentiation are phenomenological and do not reflect dedifferentiation of the cells away from an RPE fate.

The RPE cells described herein may maintain their phenotype for a long period of time in vitro. For example, the RPE cells may maintain their phenotype for at least 1, 2, 3, 4, 5, 6, 7, 8, 9, 10, 11, 12, 13, 14, 15, 16, 17, 18, 19, or 20 passages. The RPE cells may maintain their phenotype for at least about 1, 2, 3, 4, 5, 6, 7, 8, 9, 10, 11, 12, 13, 14, 15, 16, 17, 18, 19, or 20 days. The RPE cells may maintain their phenotype for at least about 1, 2, 3, 4, 5, 6, 7, 8, 9, or 10 weeks.

Moreover, the RPE cells described herein may maintain their phenotype following transplantation. The RPE cells may maintain their phenotype for the lifespan of the receipt after transplantation. For example, the RPE cells may maintain their phenotype following transplantation for at least about 1, 2, 3, 4, 5, 6, 7, 8, 9, 10, 11, 12, 13, 14, 15, 16, 17, 18, 19, or days. Further, the RPE cells may maintain their phenotype following transplantation for at least about 1, 2, 3, 4, 5, 6, 7, 8, 9, or 10 weeks. The RPE cells may maintain their phenotype following transplantation for at least about 1, 2, 3, 4, 5, 6, 7, 8, 9, 10, 11, or 12 months. The RPE cells may maintain their phenotype following transplantation for at least about 1, 2, 3, 4, 5, 6, 7, 8, 9, 10, 11, 12, 13, 14, 15, 16, 17, 18, 19, or 20 years.

The RPE cells have an increased ability to prevent neovascularization. The RPE cells may be produced by aging a somatic cell from a patient such that telomerase is shortened where at least 10% of the normal replicative lifespan of the cell has been passed, then the use of said somatic cell as a nuclear transfer donor cell to create cells that overexpress angiogenesis inhibitors such as Pigment Epithelium Derived Factor (PEDF/EPC-1). Alternatively such cells may be genetically modified with exogenous genes that inhibit neovascularization.

Preparations of RPE Cells

The present invention provides preparations of RPE cells. The invention described herein provides RPE cells, substantially purified populations of RPE cells, pharmaceutical preparations comprising RPE cells, and cryopreserved preparations of the RPE cells. The RPE cells described herein may be substantially free of at least one protein, molecule, or other impurity that is found in its natural environment (e.g., "isolated".) The RPE cells may be mammalian, including, human RPE cells. The invention also provides human RPE cells, a substantially purified population of human RPE cells, pharmaceutical preparations comprising human RPE cells, and cryopreserved preparations of the human RPE cells. The preparation may be a preparation comprising human embryonic stem cell-derived RPE cells, human iPS cell-derived RPE cells, and substantially purified (with respect to non-RPE cells) preparations comprising differentiated ES-derived RPE cells.

The RPE cell populations may include differentiated RPE cells of varying levels of maturity, or may be substantially pure with respect to differentiated RPE cells of a particular level of maturity. The RPE cells may be a substantially purified preparation comprising RPE cells of varying levels of maturity/pigmentation. For example, the substantially purified culture of RPE cells may contain both differentiated RPE cells and mature differentiated RPE cells. Amongst the mature RPE cells, the level of pigment may vary. However, the mature RPE cells may be distinguished visually from the RPE cells based on the increased level of pigmentation and the more columnar shape. The substantially purified preparation of RPE cells comprises RPE cells of differing levels of maturity (e.g., differentiated RPE cells and mature differentiated RPE cells). In such instances, there may be variability across the preparation with respect to expression of markers indicative of pigmentation. The pigmentation of the RPE cells in the cell culture may be homogeneous. Further, the pigmentation of the RPE cells in the cell culture may be heterogeneous, and the culture of RPE cells may comprise both differentiated RPE cells and mature RPE cells. Preparations comprising RPE cells include preparations that are substantially pure, with respect to non-RPE cell types, but which contain a mixture of differentiated RPE cells and mature differentiated RPE cells. Preparations comprising RPE cells also include preparations that are substantially pure both with respect to non-RPE cell types and with respect to RPE cells of other levels of maturity.

The percentage of mature differentiated RPE cells in the culture may be reduced by decreasing the density of the culture. Thus, the methods described herein may further comprise subculturing a population of mature RPE cells to produce a culture containing a smaller percentage of mature RPE cells. The number of RPE cells in the preparation includes differentiated RPE cells, regardless of level of maturity and regardless of the relative percentages of differentiated RPE cells and mature differentiated RPE cells. The number of RPE cells in the preparation refers to the number of either differentiated RPE cells or mature RPE cells. The preparation may comprise at least about 75%, 80%, 85%, 90%, 91%, 92%, 93%, 94%, 95%, 96%, 97%, 98%, 99%, or 100% differentiated RPE cells. The preparation may comprise at least about 75%, 80%, 85%, 90%, 91%, 92%, 93%, 94%, 95%, 96%, 97%, 98%, 99%, or 100% mature RPE cells. The RPE cell preparation may comprise a mixed population of differentiated RPE cells and mature RPE cells.

The invention provides a cell culture comprising human RPE cells which are pigmented and express at least one gene that is not expressed in a cell that is not a human RPE. For example, although such RPE cells may have substantially the same expression of RPE65, PEDF, CRALBP, and bestrophin as a natural human RPE cell. The RPE cells may vary, depending on level of maturity, with respect to expression of one or more of PAX2, Pax-6, MitF, and/or tyrosinase. Note that changes in pigmentation post-differentiation also correlate with changes in PAX2 expression. Mature RPE cells may be distinguished from RPE cells by the level of pigmentation, level of expression of PAX2, Pax-6, and/or tyrosinase. For example, mature RPE cells may have a higher level of pigmentation or a higher level of expression of PAX2, Pax-6, and/or tyrosinase compared to RPE cells.

The preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The RPE cell preparations may comprise at least about $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells. The RPE cell preparations may comprise at least about 5,000-10,000, 50,000-100,000, 100,000-200,000, 200,000-500,000, 300,000-500,000, or 400,000-500,000 RPE cells. The RPE cell preparation may comprise at least about 20,000-50,000 RPE cells. Also, the RPE cell preparation may comprise at least about 5,000, 10,000, 20,000, 30,000, 40,000, 50,000, 60,000, 70,000, 75,000, 80,000, 100,000, or 500,000 RPE cells.

The RPE cell preparations may comprise at least about $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^{7'}$, $5\times10^7$, $6\times10^7$, $7\times10^{7'}$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells/mL. The RPE cell preparations may comprise at least about 5,000-10,000, 50,000-100,000, 100,000-200,000, 200,000-500,000, 300,000-500,000, or 400,000-500,000 RPE cells/mL. The RPE cell preparation may comprise at least about 20,000-50,000 RPE cells/mL. Also, the RPE cell preparation may comprise at least about 5,000, 10,000, 20,000, 30,000, 40,000, 50,000, 60,000, 75,000, 80,000, 100,000, or 500,000 RPE cells/mL.

The preparations described herein may be substantially free of bacterial, viral, or fungal contamination or infection, including but not limited to the presence of HIV-1, HIV-2, HBV, HCV, CMV, HTLV-1, HTLV-2, parvovirus B19, Epstein-Barr virus, or herpesvirus 6. The preparations described herein may be substantially free of mycoplasma contamination or infection.

The RPE cells described herein may also act as functional RPE cells after transplantation where the RPE cells form a monolayer between the neurosensory retina and the choroid in the patient receiving the transplanted cells. The RPE cells may also supply nutrients to adjacent photoreceptors and dispose of shed photoreceptor outer segments by phagocytosis. Additionally, the RPE cells described herein may have undergone less senescence than cells derived from eye donors (e.g., the RPE cells are "younger" than those of eye donors). This allows the RPE cell described herein to have a longer useful lifespan than cells derived from eye donors.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant.)

RPE Cell Cultures

The present invention also provides substantially purified cultures of RPE cells, including human RPE cells. The RPE cultures described herein may comprise at least about 1,000; 2,000; 3,000; 4,000; 5,000; 6,000; 7,000; 8,000; or 9,000 RPE cells. The culture may comprise at least about $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10$ RPE cells.

The RPE cells are further cultured to produce a culture of mature RPE cells. The RPE cells may be matured, and the RPE cells may be further cultured in, for example MDBK-MM medium until the desired level of maturation is obtained. This may be determined by monitoring the increase in pigmentation level during maturation. As an alternative to MDBK-MM medium, a functionally equivalent or similar medium, may be used. Regardless of the particular medium used to mature the RPE cells, the medium may optionally be supplemented with a growth factor or agent. Both RPE cells and mature RPE cells are differentiated RPE cells. However, mature RPE cells are characterized by increased level of pigment in comparison to differentiated RPE cells. The level of maturity and pigmentation may be modulated by increasing or decreasing the density of the culture of differentiated RPE cells. Thus, a culture of RPE cells may be further cultured to produce mature RPE cells. Alternatively, the density of a culture containing mature RPE cells may be decreased to decrease the percentage of mature differentiated RPE cells and increase the percentage of differentiated RPE cells.

The RPE cells may be identified by comparing the messenger RNA transcripts of such cells with cells derived in vivo. An aliquot of cells is taken at various intervals during the differentiation of embryonic stem cells to RPE cells and assayed for the expression of any of the markers described above. These characteristic distinguish differentiated RPE cells.

The RPE cell culture may be a substantially purified culture comprising at least about 30%, 35%, 40%, or 45%, 50%, 55%, 60%, 65%, 70%, 75%, 80%, 85%, 90%, 91%, 92%, 93%, 94%, 95%, 96%, 97%, 98%, 99%, or 100% differentiated RPE cells. The substantially purified culture may comprise at least about 30%, 35%, 40%, or 45%, 50%, 55%, 60%, 65%, 70%, 75%, 80%, 85%, 90%, 91%, 92%, 93%, 94%, 95%, 96%, 97%, 98%, 99%, or 100% mature differentiated RPE cells.

The RPE cell cultures may be prepared in accordance with Good Manufacturing Practices (GMP) (e.g., the cultures are GMP-compliant) and/or current Good Tissue Practices (GTP) (e.g., the cultures may be GTP-compliant.)

Cryopreserved Preparations of RPE Cells

RPE cells may be frozen for storage. The RPE cells may be stored by any appropriate method known in the art (e.g., cryogenically frozen) and may be frozen at any temperature appropriate for storage of the cells. For example, the cells may be frozen at about −20° C., −80° C., −120° C., −130° C., −135° C., −140° C., −150° C., −160° C., −170° C., −180° C., −190° C., −196° C., at any other temperature appropriate for storage of cells. Cryogenically frozen cells may be stored in appropriate containers and prepared for storage to reduce risk of cell damage and maximize the likelihood that the cells will survive thawing. RPE cells may be cryopreserved immediately following differentiation, following in vitro maturation, or after some period of time in culture. The RPE cells may also be maintained at room temperature, or refrigerated at, for example, about 4° C.

Similarly provided are methods of cryopreserving RPE cells. The RPE cells may be harvested, washed in buffer or media, counted, concentrated (via centrifugation), formulated in freezing media (e.g., 90% FBS/10% DMSO), or any combination of these steps. For example, the RPE cells may be seeded in several culture vessels and serially expanded. As the RPE cells are harvested and maintained in FBS at about 4° C. while several flasks of RPE cells are combined into a single lot. The RPE cells may be also washed with saline solution (e.g., DPBS) at least 1, 2, 3, 4, or 5 times. Further, the RPE cells may be cryopreserved after dystrophin is organized at the cell membrane and PAX6 expression is low. In addition, the vials may be labeled, with a primary and/or secondary label. The information on the label may include the type of cell (e.g., hRPE cells), the lot number and date, the number of cells (e.g., $1 \times 10^6$ cells/mL), the expiration date (e.g., recommended date by which the vial should be used), manufacture information (e.g., name and address), warnings, and the storage means (e.g., storage in liquid nitrogen).

Cryopreserved RPE cell preparations described herein may comprise at least about 50,000-100,000 RPE cells. The cryopreserved RPE cell preparations may also comprise at least about 20,000-500,000 RPE cells. Also, the cryopreserved RPE cell preparations may comprise at least about 5,000, 10,000, 20,000, 30,000, 40,000, 50,000, 60,000, 75,000, 80,000, or 100,000 RPE cells. The cryopreserved RPE cell preparations may comprise at least about 1,000, 2,000, 3,000, 4,000, 5,000, 10,000, 20,000, 30,000, 40,000, 50,000, 60,000, 75,000, 80,000, 100,000, or 500,000 RPE cells. The cryopreserved RPE cell preparations may comprise at least about 1,000, 2,000, 3,000, 4,000, 5,000, 6,000, 7,000, 8,000, 9,000, $1 \times 10^4$, $2 \times 10^4$, $3 \times 10^4$, $4 \times 10^4$, $5 \times 10^4$, $6)(10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ RPE cells. The RPE cells of the cryopreserved RPE cell preparations may be mammalian RPE cells, including human RPE cells.

Further, the cryopreserved RPE cell preparations described herein may comprise at least about 50,000-100,000 RPE cells/mL. The cryopreserved RPE cell preparations may also comprise at least about 20,000-500,000 RPE cells/mL. Also, the cryopreserved RPE cell preparations may comprise at least about 5,000, 10,000, 20,000, 30,000, 40,000, 50,000, 60,000, 75,000, 80,000, and 100,000 RPE cells/mL. The cryopreserved RPE cell preparations may comprise at least about 1,000, 2,000, 3,000, 4,000, 5,000, 10,000, 20,000, 30,000, 40,000, 50,000, 60,000, 75,000, 80,000, 100,000, or 500,000 RPE cells/mL. The cryopreserved RPE cell preparations may comprise at least about 1,000, 2,000, 3,000, 4,000, 5,000, 6,000, 7,000, 8,000, 9,000, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells/mL. The RPE cells of the cryopreserved RPE cell preparations may be mammalian RPE cells, including human RPE cells.

The RPE cells of the invention may be recovered from storage following cryopreservation. The RPE cells recovered from cryopreservation also maintain their viability and differentiation status. For example, at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the RPE cells may retain viability and differentiation following cryopreservation. Further, the RPE cells of the invention may be cryopreserved and maintain their viability after being stored for at least about 1, 2, 3, 4, 5, 6, or 7 days. The RPE cells of the invention may also be cryopreserved and maintain their viability after being stored for at least about 1, 2, 3, 4, 5, 6, 7, 8, 9, 10, 11, or 12 months. The RPE cells of the invention may be cryopreserved and maintain their viability after being stored for at least about 1, 2, 3, 4, 5, 6, or 7 years. For example, the RPE cells of the invention may be cryopreserved for at least about 4 years and show at least about 80% viability. The cryopreservation preparation comprising RPE cells may be substantially free of DMSO.

Methods of Producing RPE Cells

The present invention provides a method of producing RPE cells from pluripotent stem cells. The cell types that may be produced using this invention include, but are not limited to, RPE cells, RPE progenitor cells, iris pigmented epithelial (IPE) cells, and other vision associated neural cells, such as internuncial neurons (e.g., "relay" neurons of the inner nuclear layer (INL)) and amacrine cells. Additionally, retinal cells, rods, cones, and corneal cells may be produced. Cells providing the vasculature of the eye may also be produced by the methods described herein.

Without being bound to a particular theory, the inventors found that the methods described herein may act through FGF, EGF, WNT4, TGF-beta, and/or oxidative stress to signal MAP-Kinase and potential C-Jun terminal Kinase pathways to induce the expression of the Paired-box 6 (PAX6) transcription factor. PAX6 acts synergistically with PAX2 to terminally differentiate mature RPE via the coordination of Mit-F and Otx2 to transcribe RPE-specific genes such as Tyrosinase (Tyr), and downstream targets such as RPE-65, Bestrophin, CRALBP, and PEDF. See WO 2009/051671, FIG. 1.

The RPE cells described herein may be differentiated from pluripotent stem cells, such as human embryonic stem cells, and are molecularly distinct from embryonic stem cells, adult-derived RPE cells, and fetal-derived RPE cells. The inventors surprisingly discovered that the method by which the RPE cells are produced from a pluripotent stem cell is a critical factor in determining the structural and functional characteristics of the resulting RPE cells. The inventors found that the RPE cells produced by the methods described produced a different RPE cell product than previous methods and sources of RPE cells. For example, the manufacturing process steps described herein impart distinctive structural and functional characteristics to the final RPE cell product such that these cells closely resemble native RPE cells and are distinct from fetal derived RPE cells or RPE cell lines (e.g., APRE19). Further, the methods of producing RPE cells described herein are not permissive to ES cells. Thus, as ES cells cannot persist in the culture processes described herein, and they do not pose an unacceptable risk of contamination in the RPE cell cultures and preparations.

The invention provides a method for producing a RPE cell comprising: (a) providing pluripotent stem cells; (b) culturing the pluripotent stem cells as embryoid bodies in nutrient rich, low protein medium, wherein the medium optionally comprises serum free B-27 supplement; (c) culturing the embryoid bodies as an adherent culture in nutrient rich, low protein medium, wherein the medium optionally comprises serum free B-27 supplement; (d) culturing the adherent culture of cells of (c) in nutrient rich, low protein medium, wherein the medium does not comprise serum free B-27 supplement; (e) culturing the cells of (d) in medium capable of supporting growth of high-density somatic cell culture, whereby RPE cells appear in the culture of cells; (f) contacting the culture of (e) with an enzyme; (g) selecting the RPE cells from the culture and transferring the RPE cells to a separate culture containing medium supplemented with a growth factor to produce an enriched culture of RPE cells; and (g) propagating the enriched culture of RPE cells to produce a RPE cell. These method steps may be performed at least once to produce a substantially purified culture of RPE cells. Further, these method steps may be repeated at least 1, 2, 3, 4, 5, 6, 7, 8, 9, or 10 times to produce more RPE cells.

Additionally, the invention also provides a method for producing a mature retinal pigment epithelial (RPE) cell comprising: (a) providing pluripotent stem cells; (b) culturing the pluripotent stem cells as embryoid bodies in nutrient rich, low protein medium, wherein the medium optionally comprises serum free B-27 supplement; (c) culturing the embryoid bodies as an adherent culture in nutrient rich, low protein medium, wherein the medium optionally comprises serum free B-27 supplement; (d) culturing the adherent culture of cells of step (c) in nutrient rich, low protein medium, wherein the medium does not comprise serum free B-27 supplement; (e) culturing the cells of (d) in medium capable of supporting growth of high-density somatic cell culture, whereby RPE cells appear in the culture of cells; (f) contacting the culture of (e) with an enzyme; (g) selecting the RPE cells from the culture and transferring the RPE cells to a separate culture containing medium supplemented with a growth factor to produce an enriched culture of RPE cells; (h) propagating the enriched culture of RPE cells; and (i) culturing the enriched culture of RPE cells to produce a mature RPE cell. These method steps may be performed at least once to produce a substantially purified culture of mature RPE cells. Further, these method steps may be repeated at least 1, 2, 3, 4, 5, 6, 7, 8, 9, or 10 times to produce more mature RPE cells.

For any of the articulated steps, the cells may be cultured for at least about 1-10 weeks. For example, the cells may be cultured for at least about 3-6 weeks. For any of the articulated steps, the cells may be cultured for between about 1 days and 50 days, for example, for at least about 1-3, 3-4,7, 4-9, 7-10, 7-12, 8-11, 9-12, 7-14, 14-21, and 3-45 days. The cells may be cultured for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days. The cells may be cultured for about 1, 2, 3, 4, 5, 6, 7, 8, 9, 10, 11, 12, 13, 14, 15, 16, 17, 18, 19, 20, 21, 22, 23, or 24 hours. For example, the cells may be cultured for 2-4 and 3-6 hours. For each of the above articulated method steps, the cells may be cultured for the same period of time at each step or for differing periods of time at one or more of the steps. Additionally, any of the above articulated method steps may be repeated to produce more RPE cells (e.g., scaled up to produce large numbers of RPE cells).

Figure 4:
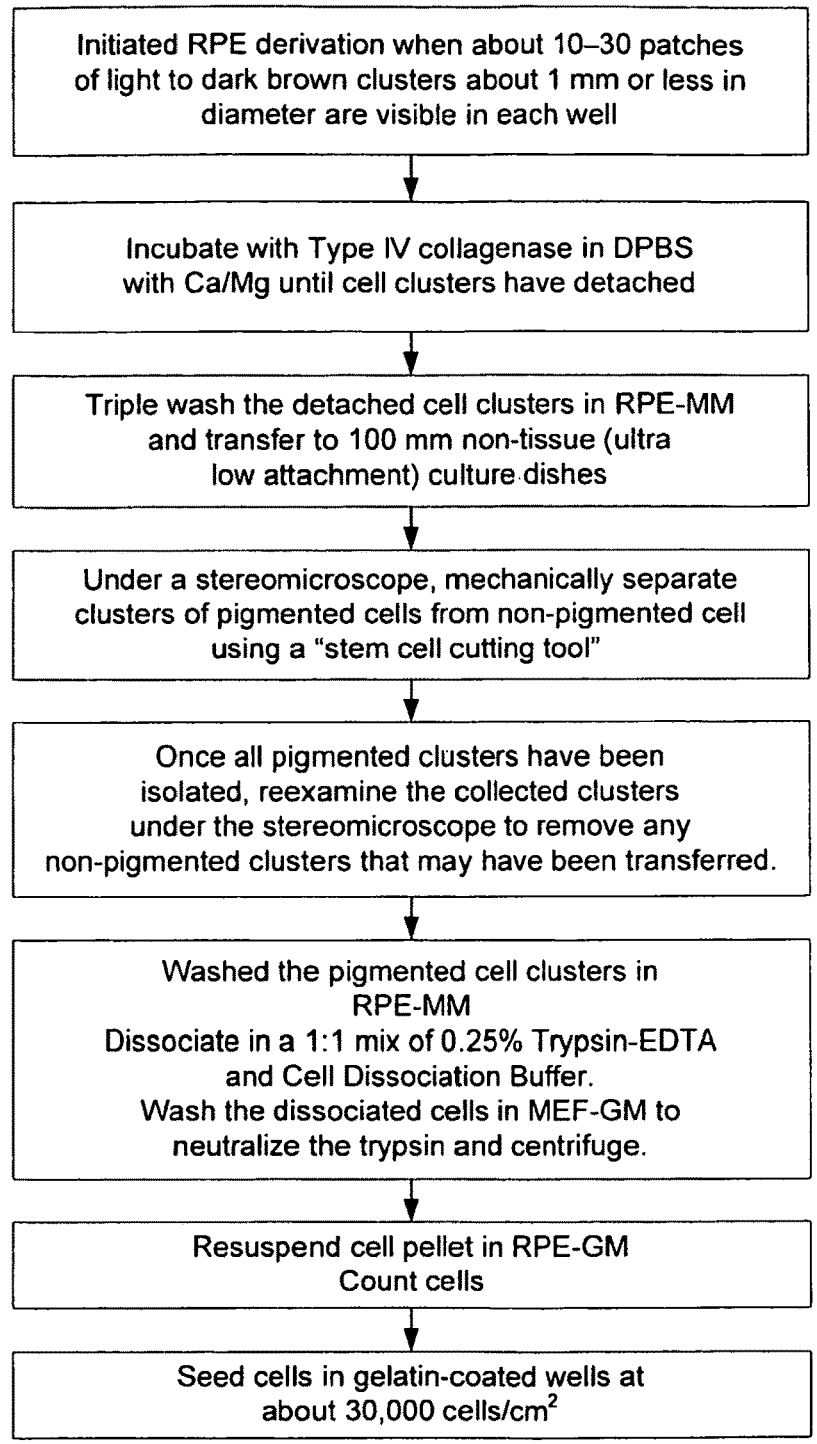

In the methods described herein, the RPE cells may begin to differentiate from amongst cells in the adherent culture of EBs. RPE cells may be visually recognized based on their cobblestone morphology and the initial appearance of pigmentation. As RPE cells continue to differentiate, clusters of RPE cells may be observed. See FIG. 4.

Mechanical or enzymatic methods are used to select RPE cells from amongst clusters of non-RPE cells in a culture of embryoid body, or to facilitate sub-culture of adherent cells. Exemplary mechanical methods include, but are not limited to, titration with a pipette or cutting with a pulled needle. Exemplary enzymatic methods include, but are not limited to, any enzymes appropriate for disassociating cells (e.g., trypsin (e.g., Trypsin/EDTA), collagenase (e.g., collagenase B, collagenase IV), dispase, papain, mixture of collagenase and dispase, a mixture of collagenase and trypsin). A non-enzymatic solution is used to disassociate the cells, such as a high EDTA-containing solution e.g., Hanks-based cell disassociation buffer.

The RPE cells differentiate from the embryoid bodies. Isolating RPE cells from the EBs allows for the expansion of the RPE cells in an enriched culture in vitro. For human cells, RPE cells may be obtained from EBs grown for less than 90 days. Further, RPE cells may arise in human EBs grown for at least about 7-14 days, 14-28 days, 28-45 days, or 45-90 days. The medium used to culture pluripotent stem cells, embryoid bodies, and RPE cells may be removed and/or replaced with the same or different media at any interval. For example, the medium may be removed and/or replaced after at least about 0-7 days, 7-10 days, 10-14 days, 14-28 days, or 28-90 days. Further, the medium may be replaced at least daily, every other day, or at least every 3 days.

Figure 5:
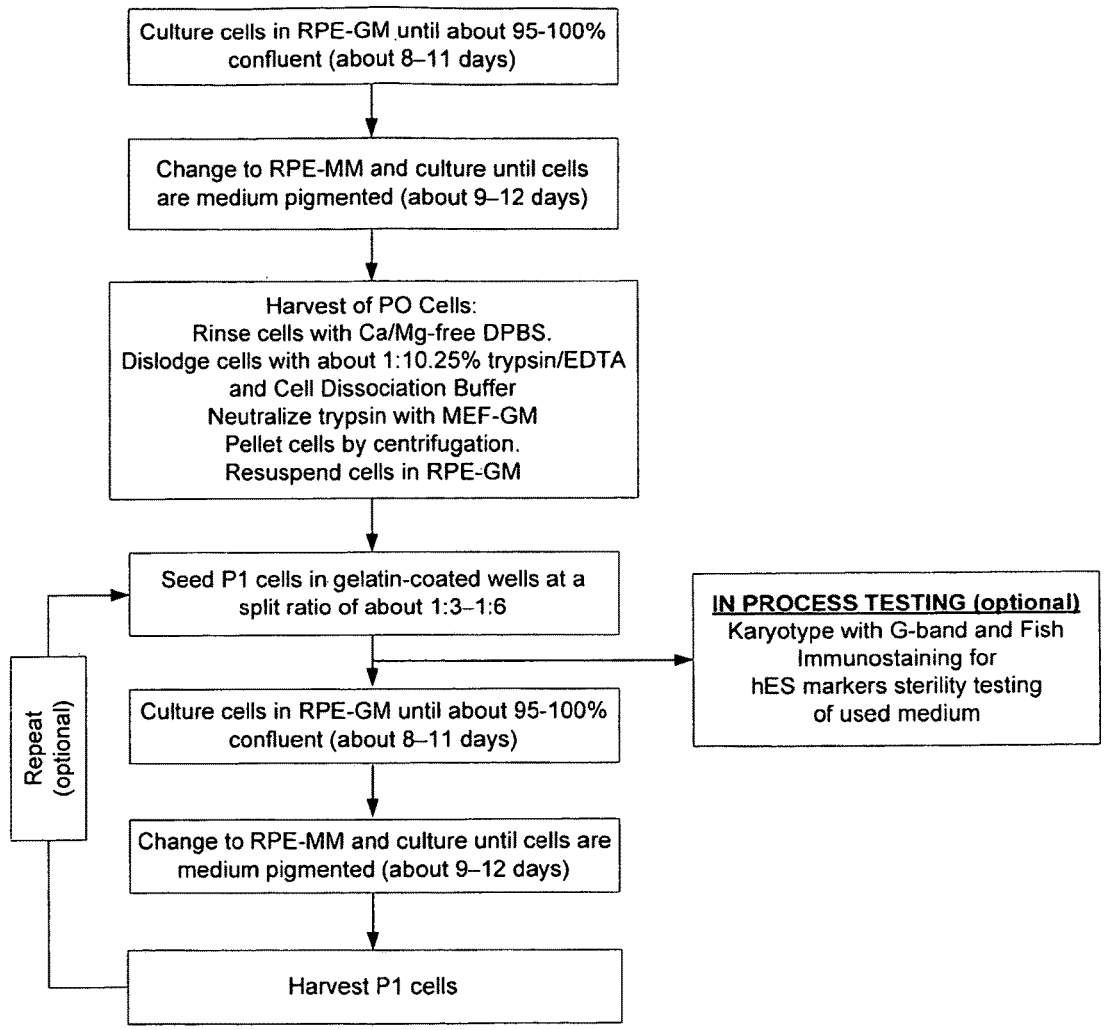

To enrich for RPE cells and to establish substantially purified cultures of RPE cells, RPE cells are dissociated from each other and from non-RPE cells using mechanical and/or chemical methods. A suspension of RPE cells may then be transferred to fresh medium and a fresh culture vessel to provide an enriched population of RPE cells. See FIG. 5.

RPE cells may be selected from the dissociated cells and cultured separately to produce a substantially purified culture of RPE cells. RPE cells are selected based on characteristics associated with RPE cells. For example, RPE cells can be recognized by cobblestone cellular morphology and pigmentation. In addition, there are several known markers of the RPE, including cellular retinaldehyde-binding protein (CRALBP), a cytoplasmic protein that is also found in apical microvilli; RPE65, a cytoplasmic protein involved in retinoid metabolism; bestrophin, the product of the Best vitelliform macular dystrophy gene (VMD2), and pigment epithelium derived factor (PEDF), a 48 kD secreted protein with angiostatic properties. The messenger RNA transcripts of these markers may be assayed using PCR (e.g., RT-PCR) or Northern blots. Also, the protein levels of these markers may be assaying using immunoblot technology or Western blots.

The RPE cells may also be selected based on cell function, such as by phagocytosis of shed rod and cone outer segments, absorption of stray light, vitamin A metabolism, regeneration of retinoids, and tissue repair. Evaluation may also be performed using behavioral tests, fluorescent angiography, histology, tight junctions conductivity, or evaluation using electron microscopy.

The enriched cultures of RPE cells may be cultured in appropriate medium, for example, EGM-2 medium. This, or a functionally equivalent or similar medium, may be supplemented with a growth factor or agent (e.g., bFGF, heparin, hydrocortisone, vascular endothelial growth factor, recombinant insulin-like growth factor, ascorbic acid, or human epidermal growth factor). The RPE cells may be phenotypically stable over a long period of time in culture (e.g., >6 weeks).

Pluripotent Stem Cells

The methods described herein may use pluripotent stem cells to produce RPE cells. Suitable pluripotent stem cells include but are not limited to embryonic stem cells, embryo-derived stem cells, and induced pluripotent stem cells, regardless of the method by which the pluripotent stem cells are derived. Pluripotent stem cells may be generated using, for example, by methods known in the art. Exemplary pluripotent stem cells include embryonic stem cells derived from the inner cell mass (ICM) of blastocyst stage embryos, as well as embryonic stem cells derived from one or more blastomeres of a cleavage stage or morula stage embryo (optionally without destroying the remainder of the embryo). Such embryonic stem cells may be generated from embryonic material produced by fertilization or by asexual means, including somatic cell nuclear transfer (SCNT), parthenogenesis, cellular reprogramming, and androgenesis. Further, suitable pluripotent stem cells include but are not limited to human embryonic stem cells, human embryo-derived stem cells, and human induced pluripotent stem cells, regardless of the method by which the pluripotent stem cells are derived.

The pluripotent stem cells (e.g., hES cells) may be cultured as a suspension culture to produce embryoid bodies (EBs). The embryoid bodies may be cultured in suspension for about 7-14 days. However, in certain embodiments, the EBs may be cultured in suspension for fewer than 7 days (less than 7, 6, 5, 4, 3, 2, or less than 1 day) or greater than 14 days. The EBs may be cultured in medium supplemented with B-27 supplement.

After culturing the EBs in suspension culture, the EBs may be transferred to produce an adherent culture. For example, the EBs may be plated onto gelatin coated plates in medium. When cultured as an adherent culture, the EBs may be cultured in the same type of media as when grown in suspension. The media may not supplemented with B-27 supplement when the cells are cultured as an adherent culture. Also, the medium is supplemented with B-27 initially (e.g., for less than or equal to about 7 days), but then subsequently cultured in the absence of B-27 for the remainder of the period as an adherent culture. The EBs may be cultured as an adherent culture for at least about 14-28. However, in certain embodiments, the EBs may be cultured as an adherent culture for fewer than about 14 days (less than 14, 13, 12, 11, 10, 9, 8, 7, 6, 5, 4, 3, 2, or less than 1 day) or greater than about 28 days.

Human Embryonic Stem Cells

Human embryonic stem (hES) cells may be used as a pluripotent stem cell in the methods described herein. Human embryonic stem cells (hES) are progeny of the inner cell mass (ICM) of a blastocyst and may remain pluripotent virtually indefinitely. The hES cells may be derived from one or more blastomeres of an early cleavage stage embryo, optionally without destroying the embryo. The hES cells may be cultured in any way known in the art, such as in the presence or absence of feeder cells. For example, the hES cells may be cultured in MDBK-GM, hESC Medium, INVITROGEN® Stem Cell Media, OptiPro SFM, VP-SFM, EGM-2, or MDBK-MM. See Stem Cell Information (Culture of Human Embryonic Stem Cells (hESC)) [NIH website, 2010]. The hES cells may be used and maintained in accordance with GMP standards.

When grown in culture on a feeder layer in defined conditions hES cells maintain a specific morphology, forming flat colonies comprised of small, tightly packed cells with a high ratio of nucleus to cytoplasm, clear boundaries between the cells, and sharp, refractile colony borders. hES cells express a set of molecular markers, such as Octamer binding protein 4 (Oct-4, a.k.a., Pou5f1), stage specific embryonic antigens (SSEA)-3 and SSEA-4, tumor rejection antigen (TRA)-1-60, TRA-1-80, alkaline phosphatase, NANOG, and Rex-1. Similar to the cells of the ICM that differentiate into predetermined lineages, hES cells in culture may be induced to differentiate. For example, hES cells may be differentiated into human RPE under the defined conditions described herein.

Human ES cells may produced using any method known in the art. For example, the hES cells may be derived from blastocyst stage embryos that were the product of in vitro fertilization of egg and sperm. Alternatively, the hES cells may be derived from one or more blastomeres removed from an early cleavage stage embryo, optionally, without destroying the remainder of the embryo. The hES cells may be produced using nuclear transfer. Also, cryopreserved hES cells may be used.

Human embryonic stem cells that may be used include, but are not limited to, MA01, MA09, ACT-4, No, 3, H1, H7, H9, H14 and ACT30 embryonic stem cells. See also NIH Human Embryonic Stem Cell Registry. An exemplary human embryonic stem cell line that may be used is MA09 cells. The isolation and preparation of MA09 cells was previously described in Klimanskaya, et al. (2006) "Human Embryonic Stem Cell lines Derived from Single Blastomeres." *Nature* 444: 481-485.

Figure 2:
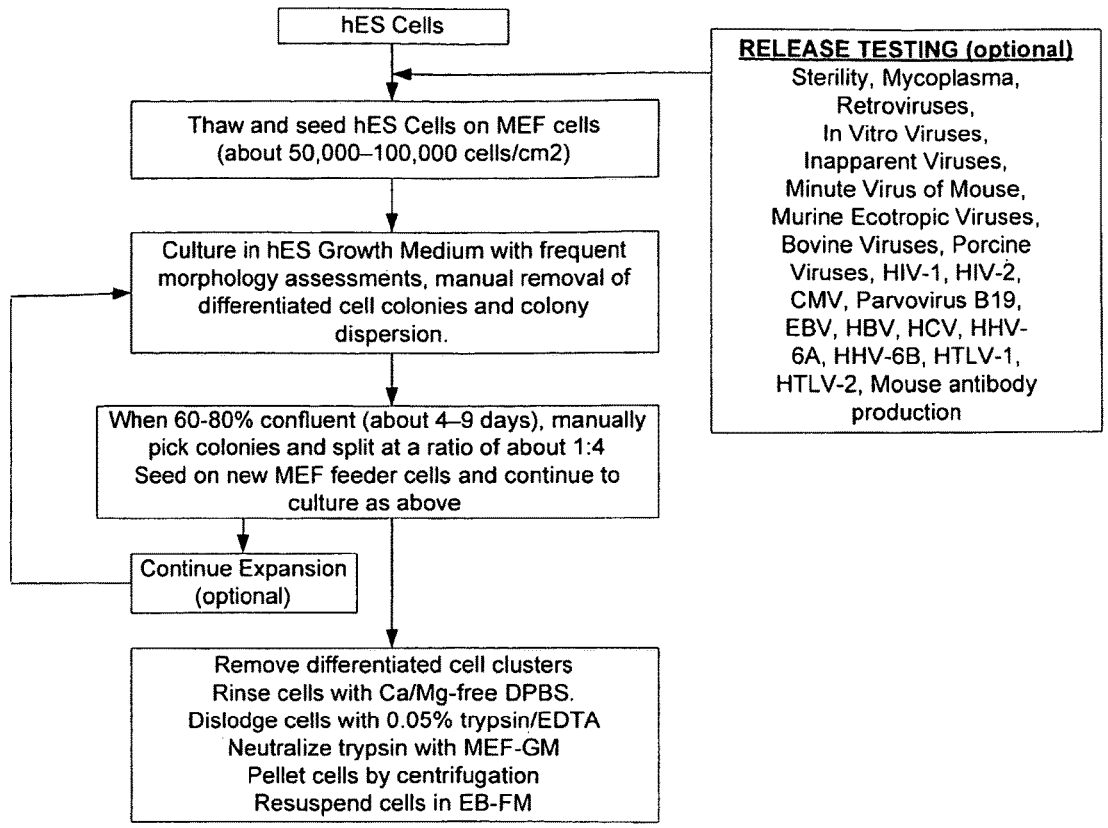
Figure 3:
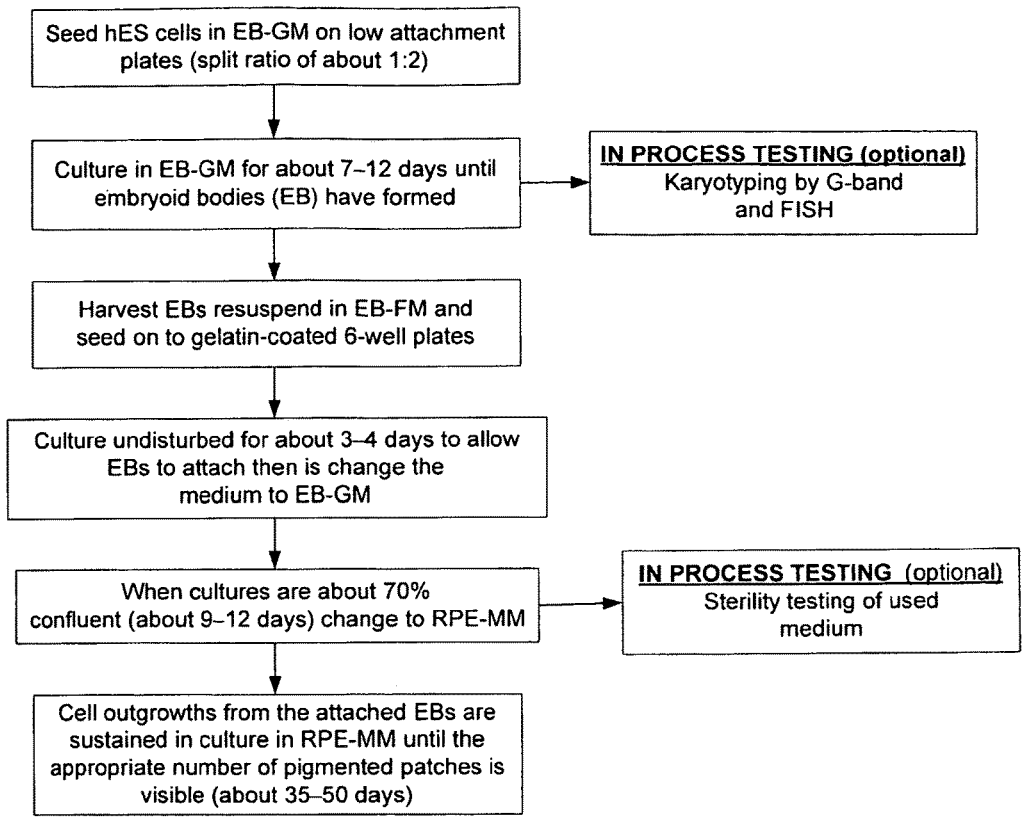

The hES cells may be initially co-cultivated with murine embryonic feeder cells (MEF) cells. The MEF cells may be mitotically inactivated by exposure to mitomycin C prior to seeding hES cells in co-culture, and thus the MEFs do not propagate in culture. See FIG. 1. Additionally, hES cell cultures are examined microscopically and colonies containing non-hES cell morphology are picked and discarded using a stem cell cutting tool. See FIG. 2. After the point of harvest of the hES cells for seeding for embryoid body formation no additional MEF cells are used in the process. See FIG. 3. The time between MEF removal and RPE cells described herein harvest may be a minimum of at least one, two, three, four, or five passages and at least about 5, 10, 20, 30, 40, 50, 60, 70, 80, 90, or 100 days in MEF-free cell culture. The time between MEF removal and harvesting the RPE cells may also be a minimum of at least about 3 passages and at least about 80-90 days in MEF-free cell culture. Due to the methods of production described herein, the RPE cell cultures and preparations described herein may be substantially free of mouse embryo fibroblasts (MEF) and human embryonic stem cells (hES).

Induced Pluripotent Stein Cells (iPS Cells)

Further exemplary pluripotent stem cells include induced pluripotent stem cells (iPS cells) generated by reprogramming a somatic cell by expressing or inducing expression of a combination of factors ("reprogramming factors"). iPS cells may be generated using fetal, postnatal, newborn, juvenile, or adult somatic cells. iPS cells may be obtained from a cell bank. Alternatively, iPS cells may be newly generated by methods known in the art prior to commencing differentiation to RPE cells. The making of iPS cells may be an initial step in the production of RPE cells. iPS cells may be specifically generated using material from a particular patient or matched donor with the goal of generating tissue-matched RPE cells. iPS cells are universal donor cells that are not substantially immunogenic.

The induced pluripotent stem cell may be produced by expressing or inducing the expression of one or more reprogramming factors in a somatic cell. The somatic cell is a fibroblast, such as a dermal fibroblast, synovial fibroblast, or lung fibroblast, or a non-fibroblastic somatic cell. The somatic cell is reprogrammed by expressing at least 1, 2, 3, 4, 5. The reprogramming factors may be selected from Oct 3/4, Sox2, NANOG, Lin28, c-Myc, and Klf4. Expression of the reprogramming factors may be induced by contacting the somatic cells with at least one agent, such as a small organic molecule agents, that induce expression of reprogramming factors.

The somatic cell may also be reprogrammed using a combinatorial approach wherein the reprogramming factor is expressed (e.g., using a viral vector, plasmid, and the like) and the expression of the reprogramming factor is induced (e.g., using a small organic molecule.) For example, reprogramming factors may be expressed in the somatic cell by infection using a viral vector, such as a retroviral vector or a lentiviral vector. Also, reprogramming factors may be expressed in the somatic cell using a non-integrative vector, such as an episomal plasmid. When reprogramming factors are expressed using non-integrative vectors, the factors may be expressed in the cells using electroporation, transfection, or transformation of the somatic cells with the vectors. For example, in mouse cells, expression of four factors (Oct3/4, Sox2, c-myc, and Klf4) using integrative viral vectors is sufficient to reprogram a somatic cell. In human cells, expression of four factors (Oct3/4, Sox2, NANOG, and Lin28) using integrative viral vectors is sufficient to reprogram a somatic cell.

Once the reprogramming factors are expressed in the cells, the cells may be cultured. Over time, cells with ES characteristics appear in the culture dish. The cells may be chosen and subcultured based on, for example, ES morphology, or based on expression of a selectable or detectable marker. The cells may be cultured to produce a culture of cells that resemble ES cells—these are putative iPS cells.

To confirm the pluripotency of the iPS cells, the cells may be tested in one or more assays of pluripotency. For examples, the cells may be tested for expression of ES cell markers; the cells may be evaluated for ability to produce teratomas when transplanted into SCID mice; the cells may be evaluated for ability to differentiate to produce cell types of all three germ layers. Once a pluripotent iPS cell is obtained it may be used to produce RPE cells.

Engineering MHC Genes in Human Embryonic Stem Cells to Obtain Reduced-Complexity RPE Cells Human embryonic stem (hES) cells may be derived from a library of human embryonic stem cells. The library of human embryonic stem cells may comprise stem cells, each of which is hemizygous, homozygous, or nullizygous for at least one MHC allele present in a human population, wherein each member of said library of stem cells is hemizygous, homozygous, or nullizygous for a different set of MHC alleles relative to the remaining members of the library. The library of human embryonic stem cells may comprise stem cells that are hemizygous, homozygous, or nullizygous for all MHC alleles present in a human population. In the context of this invention, stem cells that are homozygous for one or more histocompatibility antigen genes include cells that are nullizygous for one or more (and in some embodiments, all) such genes. Nullizygous for a genetic locus means that the gene is null at that locus (i.e., both alleles of that gene are deleted or inactivated.)

A hES cell may comprise modifications to one of the alleles of sister chromosomes in the cell's MHC complex. A variety of methods for generating gene modifications, such as gene targeting, may be used to modify the genes in the MHC complex. Further, the modified alleles of the MHC complex in the cells may be subsequently engineered to be homozygous so that identical alleles are present on sister chromosomes. Methods such as loss of heterozygosity (LOH) may be utilized to engineer cells to have homozygous alleles in the MHC complex. For example, one or more genes in a set of MHC genes from a parental allele can be targeted to generate hemizygous cells. The other set of MHC genes can be removed by gene targeting or LOH to make a null line. This null line can be used further as the embryonic cell line in which to drop arrays of the HLA genes, or individual genes, to make a hemizygous or homozygous bank with an otherwise uniform genetic background. Stem cells that are nullizygous for all MHC genes may be produced by standard methods known in the art, such as, for example, gene targeting and/or loss of heterozygosity (LOH.). See, for example, United States Patent Application Publications 2004/0091936, 2003/0217374 and 2003/0232430, and U.S. Provisional Patent Application No. 60/729,173.

Accordingly, the present invention relates to methods of obtaining RPE cells, including a library of RPE cells, with reduced MHC complexity. RPE cells with reduced MHC complexity may be used to increase the supply of available cells for therapeutic applications as it may eliminate the difficulties associated with patient matching. Such cells may be derived from stem cells that are engineered to be hemizygous or homozygous for genes of the MHC complex.

The invention also provides a library of RPE cells (and/or RPE lineage cells), wherein several lines of ES cells are selected and differentiated into RPE cells. These RPE cells and/or RPE lineage cells may be used for a patient in need of a cell-based therapy. The invention also provides a library of RPE cells, each of which is hemizygous, homozygous, or nullizygous for at least one MHC allele present in a human population, wherein each member of said library of RPE cells is hemizygous, homozygous, or nullizygous for a different set of MHC alleles relative to the remaining members of the library. The invention provides a library of human RPE cells that are hemizygous, homozygous, or nullizygous for all MHC alleles present in a human population.

Culture Medium

Any medium that is capable of supporting high-density cultures may be used in the methods described herein, such as medium for viral, bacterial, or eukaryotic cell culture. For example, the medium may be high nutrient, protein-free medium or high nutrient, low protein medium. Further, the medium also may include nutrient components such as albumin, B-27 supplement, ethanolamine, fetuin, glutamine, insulin, peptone, purified lipoprotein material, sodium selenite, transferrin, vitamin A, vitamin C, or vitamin E. For example, nutrient rich, low protein medium may be any medium which supports the growth of cells in culture and has a low protein content. For example, nutrient rich, low protein media includes but is not limited to MDBK-GM, OptiPro SFM, VP-SFM, DMEM, RPMI Media 1640, IDMEM, MEM, F-12 nutrient mixture, F-10 nutrient mixture EGM-2, DMEM/F-12 media, media 1999, or MDBK-MM. See also Table 2. Further, the nutrient rich, low protein medium may be a medium that does not support the growth or maintenance of embryonic stem cells.

When low protein medium is used, the medium may contain at least about 20%, 19%, 18%, 17%, 16%, 15%, 14%, 13%, 12%, 11%, 10%, 9%, 8%, 7%, 6%, 5%, 4%, 3%, 2.5%, 2%, 1.5%, 1%, 0.75%, 0.5%, 0.25%, 0.20%, 0.10%, 0.05%, 0.02%, 0.016%, 0.015%, or 0.010% animal-derived protein (e.g., 10% FBS). Note that reference to the percentage of protein present in low protein medium refers to the medium alone and does not account for protein present in, for example, B-27 supplement. Thus, it is understood that when cells are cultured in low protein medium and B-27 supplement, the percentage of protein present in the medium may be higher.

The low protein or protein free medium are supplemented with serum free B-27 supplement. Nutrient components of B27 supplement may comprise biotin, L-carnitine, corticosterone, ethanolamine, D+-galactose, reduced glutathione, linoleic acid, linolenic acid, progesterone, putrescine, retinyl acetate, selenium, triodo-1-thyronine (T3), DL-alpha-tocopherol (vitamin E), DL-alpha-tocopherol acetate, bovine serum albumin, catalase, insulin, superoxide dismutase, and transferrin. When cells are cultured in protein free medium supplemented with B-27, protein free refers to the medium prior to addition of B-27.

Growth factors, agents, and other supplements described herein may be used alone or in combination with other factors, agents, or supplements for inclusion in media. Factors, agents, and supplements may be added to the media immediately, or any time during or after cell culture.

The medium may also contain supplements such as heparin, hydrocortisone, ascorbic acid, serum (e.g., fetal bovine serum), or a growth matrix (e.g., extracellular matrix from bovine corneal epithelium, MATRIGEL® (basement membrane matrix), or gelatin), fibronectin, proteolytic fragments of fibronectin, laminin, thrombospondin, aggrecan, and syndezan.

The culture media may be supplemented with one or more factors or agents.

Growth factors that may be used include, for example, EGF, FGF, VEGF, and recombinant insulin-like growth factor. Growth factors that may be used in the present invention also include 6Ckine (recombinant), activin A, α-interferon, alpha-interferon, amphiregulin, angiogenin, β-endothelial cell growth factor, beta cellulin, β-interferon, brain derived neurotrophic factor, cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoiten, estrogen receptor-α, estrogen receptor-β, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5 S nerve growth factor (NGF), 7S-NGF, macrophage inflammatory protein-1β, macrophage inflammatory protein-2, macrophage inflammatory protein-3α, macrophage inflammatory protein-3β, monocyte chemotactic protein-1, monocyte chemotactic protein-2, monocyte chemotactic protein-3, neurotrophin-3, neurotrophin-4, NGF-β (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoetin, transforming growth factor alpha, transforming growth factor-β1, transforming growth factor-β2, transforming growth factor-β3, transforming growth-factor-β5, tumor necrosis factor (α and β, and vascular endothelial growth factor.

Agents that may be used according to the present invention include cytokines such as interferon-α, interferon-α A/D, interferon-β, interferon-γ, interferon-γ-inducible protein-10, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-15, interleukin-17, keratinocyte growth factor, leptin, leukemia inhibitory factor, macrophage colony-stimulating factor, and macrophage inflammatory protein-1 α.

The culture media may be supplemented with hormones and hormone antagonists, including but not limited to 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5'-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin. The culture media may be supplemented with antibodies to various factors including but not limited to anti-low density lipoprotein receptor antibody, anti-progesterone receptor, internal antibody, anti-alpha interferon receptor chain 2 antibody, anti-c-c chemokine receptor 1 antibody, anti-CD 118 antibody, anti-CD 119 antibody, anti-colony stimulating factor-1 antibody, anti-CSF-1 receptor/c-fms antibody, anti-epidermal growth factor (AB-3) antibody, anti-epidermal growth factor receptor antibody, anti-epidermal growth factor receptor, phospho-specific antibody, anti-epidermal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor antibody, anti-fibroblast growth factor receptor antibody, anti-fibroblast growth factor, basic antibody, anti-gamma-interferon receptor chain antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progesterone receptor antibody, anti-retinoic acid receptor-alpha antibody, anti-thyroid hormone nuclear receptor antibody, anti-thyroid hormone nuclear receptor-alpha 1/Bi antibody, anti-transforming receptor/CD71 antibody, anti-transforming growth factor-alpha antibody, anti-transforming growth factor-B3 antibody, anti-rumor necrosis factor-alpha antibody, and anti-vascular endothelial growth factor antibody.

Growth medias suitable for use in the methods described herein are listed in Table 2.

TABLE 2

GROWTH MEDIA FORMULATIONS

| NAME OF MEDIUM | FORMULATION |
|---|---|
| MEF Growth (MEF-GM) | 500 mL of IMDM |
| | 55 mL FBS |
| hES Growth (hES-GM) | 200 mL Knockout ® D-MEM |
| | 30 mL Knockout ® Serum Replacement |
| | 2 mL GlutaMAX ® -I |
| | 2 mL NEAA |
| | 200 μL 2-mercaptoethanol |
| | 10 ng/mL bFGF |
| | 10 ng/mL LIF |
| EB Growth (EB-GM) | 1 L EX-CELL ® MDBK-GM |
| | 16.5 mL GlutaMAX ® -I or |
| | 1 L OptiPRO-SFM |
| | 20 mL GlutaMAX ® -I |
| EB Formation (EB-FM) | 1 L EX-CELL ® MDBK-GM |
| | 16.5 mL GlutaMAX ® -I |
| | 20 mL B-27 Supplement or |
| | 1 L OptiPRO-SFM |
| | 20 mL GlutaMAX ® -I |
| | 20 mL B-27 Supplement |
| RPE Maintenance (RPE-MM) | 1 L EX-CELL ® MDBK-MM |
| | 20 mL GlutaMAX ® -I or |
| | 1 L VP-SFM |
| | 20 mL GlutaMAX ® -I |
| RPE Growth (RPE-GM) | 500 mL EBM ® -2 |
| | 10 mL FBS |
| | 0.2 mL hydrocortisone |
| | 2.0 mL rhFGF-B |
| | 0.5 mL R3-IGF- 1 |
| | 0.5 mL ascorbic Acid |
| | 0.5 mL rhEGF |
| | 0.5 mL heparin |
| | 0.5 mL VEGF |

Therapeutic Methods

The RPE cells and pharmaceutically preparations comprising RPE cells produced by the methods described herein may be used for cell-based treatments. The invention provides methods for treating a condition involving retinal degeneration comprising administering an effective amount of a pharmaceutical preparation comprising RPE cells, wherein the RPE cells are derived from pluripotent stem cells in vitro. Conditions involving retinal degeneration include, for example, choroideremia, diabetic retinopathy, retinal atrophy, retinal detachment, retinal dysplasia, and retinitis pigmentosa. The RPE cells described herein may also be used in methods for treating macular degeneration including but are not limited to age related macular degeneration (dry or wet), North Carolina macular dystrophy, Sorsby's fundus dystrophy, Stargardt's disease, pattern dystrophy, Best disease, malattia leventinese, Doyne's honeycomb choroiditis, dominant drusen, and radial drusen. The RPE cells described herein may also be used in methods of treating Parkinson's disease (PD).

A common feature of cell transplantation is low graft survival, for example, in many cell transplantation studies there tends to be a loss of cells immediately following transplantation (e.g., within the first week). This loss of cells does not appear to be due to rejection of the transplanted cells but rather an inability of a certain percentage of the cells to be retained at the transplant site. This lack of cell retention is most likely due to a number of factors such as the failure of the cells to attach to an underlying structure, a lack of sufficient nutrients, or physical stresses at the transplant site. Following this initial drop-off of cell number, the cell survival at various time after transplantation can vary considerably from study to study. Thus, although some studies show a steady decline in numbers, other show results where the grafted cells can reach a stable number. However, an important factor in considering the success of a transplantation is the percentage of recipients with surviving grafts following cell transplant.

In contrast with previous preparations, the RPE cells in the pharmaceutical preparations described herein may survive long term following transplantation. For example, the RPE cells may survive at least about 1, 2, 3, 4, 5, 6, 7, 8, 9, or 10 days. Additionally, the RPE cells may survive at least about 1, 2, 3, 4, 5, 6, 7, 8, 9, or 10 weeks; at least about 1, 2, 3, 4, 5, 6, 7, 8, 9, or months; or at least about 1, 2, 3, 4, 5, 6, 7, 8, 9, or 10 years. Further, the RPE cells may survive throughout the lifespan of the receipt of the transplant. Additionally, at least 10, 20, 30, 40, 50, 60, 70, 80, 90, 95, 96, 97, 98, 99, or 100% of the receipts of RPE cells described herein may show survival of the transplanted RPE cells. Further, the RPE cells described herein may successfully incorporate into the RPE layer in the transplantation receipt, forming a semi-continuous line of cells and retain expression of key RPE molecular markers (e.g., RPE65 and bestrophin). The RPE cells described herein may also attach to the Bruch's membrane, forming a stable RPE layer in the transplantation receipt. Also, the RPE cells described herein are substantially free of ES cells and the transplantation receipts does not show abnormal growth or tumor formation at the transplantation site.

The methods of treating a patient suffering from a condition associated with retinal degeneration may comprise administering a composition of the invention locally (e.g., by intraocular injection or insertion of a matrix comprising the pharmaceutical preparation of the invention). Intraocular administration of pharmaceutical preparation of the invention include, for example, delivery into the vitreous body, transcorneally, sub-conjunctival, juxtascleral, posterior scleral, and sub-tenon portions of the eye. See, for example, U.S. Pat. Nos. 7,794,704; 7,795,025; 6,943,145; and 6,943,153.

The invention also provides a method of administering human RPE cells that have been derived from reduced-complexity embryonic stem cells to a patient. This method may comprise: (a) identifying a patient that needs treatment involving administering human RPE cells to him or her; (b) identifying MHC proteins expressed on the surface of the patient's cells; (c) providing a library of human RPE cells of reduced MHC complexity made by the method for producing RPE cells of the present invention; (d) selecting the RPE cells from the library that match this patient's MHC proteins on his or her cells; (e) administering any of the cells from step (d) to said patient. This method may be performed in a regional center, such as, for example, a hospital, a clinic, a physician's office, and other health care facilities. Further, the RPE cells selected as a match for the patient, if stored in small cell numbers, may be expanded prior to patient treatment.

The RPE cells may be cultured under conditions to increase the expression of alpha integrin subunits 1-6 or 9 as compared to uncultured RPE cells or other RPE cell preparations prior to transplantation. The RPE cells described herein may be cultured to elevate the expression level of alpha integrin subunits 1, 2, 3, 4, 5, 6, or 9. The RPE cells described herein may be cultured under conditions that promote the expression of alpha integrin subunits 1-6. For example, the RPE cells may be cultured with integrin-activating agents including but not limited to manganese and the activating monoclonal antibody (mAb) TS2/16. See Afshari, et al. Brain (2010) 133(2): 448-464.

The particular treatment regimen, route of administration, and adjuvant therapy may be tailored based on the particular condition, the severity of the condition, and the patient's overall health. Administration of the pharmaceutical preparations comprising RPE cells may be effective to reduce the severity of the symptoms and/or to prevent further degeneration in the patient's condition. For example, administration of a pharmaceutical preparation comprising RPE cells may improve the patient's visual acuity. Additionally, in certain embodiments, administration of the RPE cells may be effective to fully restore any vision loss or other symptoms. Further, the RPE cell administration may treat the symptoms of injuries to the endogenous RPE layer.

Pharmaceutical Preparations of RPE Cells

The RPE cells may be formulated with a pharmaceutically acceptable carrier. For example, RPE cells may be administered alone or as a component of a pharmaceutical formulation. The subject compounds may be formulated for administration in any convenient way for use in medicine. Pharmaceutical preparations suitable for administration may comprise the RPE cells, in combination with one or more pharmaceutically acceptable sterile isotonic aqueous or non-aqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents.

When administered, the pharmaceutical preparations for use in this invention may be in a pyrogen-free, physiologically acceptable form. The preparation comprising RPE cells used in the methods described herein may be transplanted in a suspension, gel, colloid, slurry, or mixture. Further, the preparation may desirably be encapsulated or injected in a viscous form into the vitreous humor for delivery to the site of retinal or choroidal damage. Also, at the time of injection, cryopreserved RPE cells may be may be resuspended with commercially available balanced salt solution to achieve the desired osmolality and concentration for administration by subretinal injection.

The RPE cells of the invention may be delivered in a pharmaceutically acceptable ophthalmic formulation by intraocular injection. When administering the formulation by intravitreal injection, for example, the solution may be concentrated so that minimized volumes may be delivered. Concentrations for injections may be at any amount that is effective and non-toxic, depending upon the factors described herein. The pharmaceutical preparations of RPE cells for treatment of a patient may be formulated at doses of at least about $10^4$ cells/mL. The RPE cell preparations for treatment of a patient are formulated at doses of at least about $10^3$, $10^4$, $10^5$, $10^6$, $10^7$, $10^8$, $10^9$, or $10^{10}$ RPE cells/mL. For example, the RPE cells may be formulated in a pharmaceutically acceptable carrier or excipient.

The pharmaceutical preparations of RPE cells described herein may comprise at least about 1,000; 2,000; 3,000; 4,000; 5,000; 6,000; 7,000; 8,000; or 9,000 RPE cells. The pharmaceutical preparations of RPE cells may comprise at least about $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10'$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ RPE cells. The pharmaceutical preparations of RPE cells may comprise at least about $1\times10^2$-$1\times10^3$, $1\times10^2$-$1\times10^4$-$1\times10^5$, or $1\times10^3$-$1\times10^6$ RPE cells. The pharmaceutical preparations of RPE cells may comprise at least about 10,000, 20,000, 25,000, 50,000, 75,000, 100,000, 125,000, 150,000, 175,000, 180,000, 185,000, 190,000, or 200,000 RPE cells. For example, the pharmaceutical preparation of RPE cells may comprise at least about 20,000-200,000 RPE cells in a volume at least about 50-200 µL. Further, the pharmaceutical preparation of RPE cells may comprise at least about 180,000 RPE cells in a volume at least about 150 µL.

RPE cells may be formulated for delivery in a pharmaceutically acceptable ophthalmic vehicle, such that the preparation is maintained in contact with the ocular surface for a sufficient time period to allow the cells to penetrate the affected regions of the eye, as for example, the anterior chamber, posterior chamber, vitreous body, aqueous humor, vitreous humor, cornea, iris/ciliary, lens, choroid, retina, sclera, suprachoridal space, conjunctiva, subconjunctival space, episcleral space, intracorneal space, epicorneal space, pars plana, surgically-induced avascular regions, or the macula.

The volume of preparation administered according to the methods described herein may dependent on factors such as the mode of administration, number of RPE cells, age and weight of the patient, and type and severity of the disease being treated. If administered by injection, the volume of a pharmaceutical preparations of RPE cells of the invention may be from at least about 1, 1.5, 2, 2.5, 3, 4, or 5 mL. The volume may be at least about 1-2 mL. For example, if administered by injection, the volume of a pharmaceutical preparations of RPE cells of the invention may be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 µL (microliters). For example, the volume of a preparation of the invention may be from at least about 10-50, 20-50, 25-50, or 1-200 µL. The volume of a preparation of the invention may be at least about 10, 20, 30, 40, 50, 100, 110, 120, 130, 140, 150, 160, 170, 180, 190, or 200 µL.

For example, the preparation may comprise at least about $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, or $9\times10^4$ RPE cells per µL. The preparation may comprise 2000 RPE cells per µL, for example, 100,000 RPE cells per 50 µL or 180,000 RPE cells per 90 µL.

The method of treating retinal degeneration may further comprise administration of an immunosuppressant. Immunosuppressants that may be used include but are not limited to anti-lymphocyte globulin (ALG) polyclonal antibody, anti-thymocyte globulin (ATG) polyclonal antibody, azathioprine, BASILIXIMAB® (anti-IL-2Rα receptor antibody), cyclosporin (cyclosporin A), DACLIZUMAB® (anti-IL-2Rα receptor antibody), everolimus, mycophenolic acid, RITUXIMAB® (anti-CD20 antibody), sirolimus, and tacrolimus. The immunosuppressants may be dosed at least about 1, 2, 4, 5, 6, 7, 8, 9, or 10 mg/kg. When immunosuppressants are used, they may be administered systemically or locally, and they may be administered prior to, concomitantly with, or following administration of the RPE cells. Immunosuppressive therapy continues for weeks, months, years, or indefinitely following administration of RPE cells. For example, the patient may be administered 5 mg/kg cyclosporin for 6 weeks following administration of the RPE cells.

The method of treatment of retinal degeneration may comprise the administration of a single dose of RPE cells. Also, the methods of treatment described herein may comprise a course of therapy where RPE cells are administered multiple times over some period. Exemplary courses of treatment may comprise weekly, biweekly, monthly, quarterly, biannually, or yearly treatments. Alternatively, treatment may proceed in phases whereby multiple doses are required initially (e.g., daily doses for the first week), and subsequently fewer and less frequent doses are needed.

If administered by intraocular injection, the RPE cells may be delivered one or more times periodically throughout the life of a patient. For example, the RPE cells may be delivered once per year, once every 6-12 months, once every 3-6 months, once every 1-3 months, or once every 1-4 weeks. Alternatively, more frequent administration may be desirable for certain conditions or disorders. If administered by an implant or device, the RPE cells may be administered one time, or one or more times periodically throughout the lifetime of the patient, as necessary for the particular patient and disorder or condition being treated. Similarly contemplated is a therapeutic regimen that changes over time. For example, more frequent treatment may be needed at the outset (e.g., daily or weekly treatment). Over time, as the patient's condition improves, less frequent treatment or even no further treatment may be needed.

The methods described herein may further comprises the step of monitoring the efficacy of treatment or prevention by measuring electroretinogram responses, optomotor acuity threshold, or luminance threshold in the subject. The method may also comprise monitoring the efficacy of treatment or prevention by monitoring immunogenicity of the cells or migration of the cells in the eye.

The RPE cells may be used in the manufacture of a medicament to treat retinal degeneration. The invention also encompasses the use of the preparation comprising RPE cells in the treatment of blindness. For example, the preparations comprising human RPE cells may used to treat retinal degeneration associated with a number of vision-altering ailments that result in photoreceptor damage and blindness, such as, diabetic retinopathy, macular degeneration (including age-related macular degeneration, e.g., wet age-related macular degeneration and dry age-related macular degeneration), retinitis pigmentosa, and Stargardt's Disease (fundus flavimaculatus). The preparation may comprise at least about 5,000-500,000 RPE cells (e.g., 100,00 RPE cells) which may be administered to the retina to treat retinal degeneration associated with a number of vision-altering ailments that result in photoreceptor damage and blindness, such as, diabetic retinopathy, macular degeneration (including age-related macular degeneration), retinitis pigmentosa, and Stargardt's Disease (fundus flavimaculatus).

The RPE cells provided herein may be human RPE cells. Note, however, that the human cells may be used in human patients, as well as in animal models or animal patients. For example, the human cells may be tested in mouse, rat, cat, dog, or non-human primate models of retinal degeneration. Additionally, the human cells may be used therapeutically to treat animals in need thereof, such as in veterinary medicine.

Modes of Administration

The pharmaceutical preparation may be formulated in a pharmaceutically acceptable carrier according to the route of administration. For example, the preparation may be formulated to be administered to the subretinal space of the eye. The preparation comprising RPE cells may be administered to one eye or both eyes in the same patient. The administration to both eyes may be sequential or simultaneous. For example, the preparation comprising RPE cells may be formulated as a suspension, solution, slurry. gel, or colloid.

RPE cells of the invention may be administered locally by injection (e.g., intravitreal injection), or as part of a device or implant (e.g., an implant). For example, the preparation may be administered by injection into the subretinal space of the eye. Also, the preparation may be administered transcorneally. For example, the cells of the present invention may be transplanted into the subretinal space by using vitrectomy surgery. Additionally, at the time of injection, RPE cells may be may be resuspended with commercially available balanced salt solution to achieve the desired osmolality and concentration for administration by subretinal injection.

Depending on the method of administration, the RPE cells may be added to buffered and electrolyte balanced aqueous solutions, buffered and electrolyte balanced aqueous solutions with a lubricating polymer, mineral oil or petrolatum-based ointment, other oils, liposomes, cylcodextrins, sustained release polymers or gels.

Matrices for Use with RPE Cells

The methods described herein may comprise a step of administering RPE cells of the invention as an implant or device. In certain embodiments, the device is bioerodible implant for treating a medical condition of the eye comprising an active agent dispersed within a biodegradable polymer matrix, wherein at least about 75% of the particles of the active agent have a diameter of less than about 10 µm. The bioerodible implant is sized for implantation in an ocular region. The ocular region may be any one or more of the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina. The biodegradable polymer may be, for example, a poly(lactic-co-glycolic)acid (PLGA) copolymer, biodegradable poly(DL-lactic-co-glycolic acid) films, or PLLA/PLGA polymer substrates. The ratio of lactic to glycolic acid monomers in the polymer is about 25/75, 40/60, 50/50, 60/40, 75/25 weight percentage, more preferably about 50/50. The PLGA copolymer may be about 20, 30, 40, 50, 60, 70, 80 to about 90 percent by weight of the bioerodible implant. The PLGA copolymer may be from about 30 to about 50 percent by weight, preferably about 40 percent by weight of the bioerodible implant. The RPE cells may be transplanted in conjunction with a biocompatible polymer such as polylactic acid, poly(lactic-co-glycolic acid), 50:50 PDLGA, 85:15 PDLGA, and INION GTR® biodegradable membrane (mixture of biocompatible polymers). See U.S. Pat. Nos. 6,331,313; 7,462,471; and 7,625,582. See also Hutala, et al. (2007) "In vitro biocompatibility of degradable biopolymers in cell line cultures from various ocular tissues: Direct contact studies." *Journal of Biomedical Materials Research* 83A(2): 407-413; Lu, et al. (1998) *J Biomater Sci Polym Ed* 9: 1187-205; and Tomita, et al. (2005) *Stem Cells* 23: 1579-88.

Screening Assays

The invention provides a method for screening to identify agents that modulate RPE cell maturity. For example, RPE cells differentiated from human ES cells may be used to screen for agents that promote RPE maturation. Identified agents may be used, alone or in combination with RPE cells, as part of a treatment regimen. Alternatively, identified agents may be used as part of a culture method to improve the survival of RPE cells differentiated in vitro.

The RPE cells may be used a research tool in settings such as a pharmaceutical, chemical, or biotechnology company, a hospital, or an academic or research institution. Such uses include the use of RPE cells differentiated from embryonic stem cells in screening assays to identify, for example, agents that may be used to promote RPE survival in vitro or in vivo, or that may be used to promote RPE maturation. Identified agents may be studied in vitro or in animal models to evaluate, for example, their potential use alone or in combination with RPE cells.

The invention provides a method for identifying agents that promote RPE maturation comprising providing a RPE cell, contacting said RPE cell with an agent, assessing said RPE cell for signs of maturity, and then identifying an agent that promotes RPE maturation when said agent causes RPE cell to show signs of maturity. The signs of maturity may be pigmentation level, gene expression levels, and morphology as discussed herein.

Commercial Applications and Methods

Certain aspects of the present invention pertain to the production of RPE cells to reach commercial quantities. The RPE cells may be produced on a large scale, stored if necessary, and supplied to hospitals, clinicians or other healthcare facilities.

Accordingly certain aspects of the present invention relate to methods of production, storage, and distribution of RPE cells produced by the methods disclosed herein. Following RPE production, RPE cells may be harvested, purified, and optionally stored prior to a patient's treatment. RPE cells may optionally be patient specific or specifically selected based on HLA or other immunologic profile. For example, once a patient presents with an indication such as, for example, diabetic retinopathy, macular degeneration (including age-related macular degeneration), retinitis pigmentosa, retinal atrophy, retinal detachment, retinal dysplasia, and Stargardt's Disease (fundus flavimaculatus), RPE cells may be ordered and provided in a timely manner. Accordingly, the present invention relates to methods of producing RPE cells to attain cells on a commercial scale, cell preparations comprising RPE cells derived from said methods, as well as methods of providing (i.e., producing, optionally storing, and selling) RPE cells to hospitals and clinicians. The production of differentiated RPE cells or mature differentiated RPE cells may be scaled up for commercial use.

The present invention also provides for methods of conducting a pharmaceutical business comprising establishing a distribution system for distributing the preparation for sale or may include establishing a sales group for marketing the pharmaceutical preparation.

The present invention provides methods of supplying RPE cells to hospitals, healthcare centers, and clinicians, whereby RPE cells produced by the methods disclosed herein are stored, ordered on demand by a hospital, healthcare center, or clinician, and administered to a patient in need of RPE cell therapy. A hospital, healthcare center, or clinician orders RPE cells based on patient specific data, RPE cells are produced according to the patient's specifications and subsequently supplied to the hospital or clinician placing the order. For example, after a particular RPE cell preparation is chosen to be suitable for a patient, it is thereafter expanded to reach appropriate quantities for patient treatment.

Further aspects of the invention relate to a library of RPE cells that can provide matched cells to potential patient recipients. Accordingly, the invention provides a method of conducting a pharmaceutical business, comprising the step of providing RPE cell preparations that are homozygous for at least one histocompatibility antigen, wherein cells are chosen from a bank of such cells comprising a library of RPE cells that may be expanded by the methods disclosed herein, wherein each RPE cell preparation is hemizygous or homozygous for at least one MHC allele present in the human population, and wherein said bank of RPE cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the RPE cells.

The present invention also includes methods of obtaining human ES cells from a patient and then generating and expanding RPE cells derived from the ES cells. These RPE cells may be stored. In addition, these RPE cells may be used to treat the patient from which the ES were obtained or a relative of that patient.

The present disclosure demonstrates that human RPE cells may be reliably differentiated and expanded from human ES cells under well-defined and reproducible conditions—representing an inexhaustible source of cells for patients with retinal degenerative disorders. The concentration of these cells would not be limited by availability, but rather could be titrated to the precise clinical requirements of the individual. Repeated infusion or transplantation of the same cell population over the lifetime of the patient would also be possible if deemed necessary by the physician. Furthermore, the ability to create banks of matching or reduced-complexity HLA hES lines from which RPE cells could be produced could potentially reduce or eliminate the need for immunosuppressive drugs and/or immunomodulatory protocols altogether.

The present invention will now be more fully described with reference to the following examples, which are illustrative only and should not be considered as limiting the invention described above.

EXAMPLES

The invention now being generally described, it will be more readily understood by reference to the following examples, which are included merely for purposes of illustration of certain aspects and embodiments of the present invention, and are not intended to limit the invention.

Example 1

Method of Making Human RPE Cells Using HES Cells

Mouse embryo fibroblasts (MEF) were grown in MEF-GM medium supplemented with about 10% fetal bovine serum (FBS). When sufficient numbers of MEFs were obtained, feeder cells were prepared by mitotically blocking the MEFs with mitomycin-C and seeding into 6-well plates coated with gelatin. See FIG. 1. Vials of hES were thawed, seeded on to the MEF feeder cells, and co-cultured in hES Growth Medium. See Table 2 and FIG. 2. The hES cells were expanded several times at a split ratio of about 1:3. When a sufficient number of hES cells were propagated, the cells were harvested and placed into suspension culture in low attachment 6-well plates in EB Formation Medium (this allows for the formation of embryoid bodies (EBs)). See Table 2 and FIG. 3.

Figure 6:
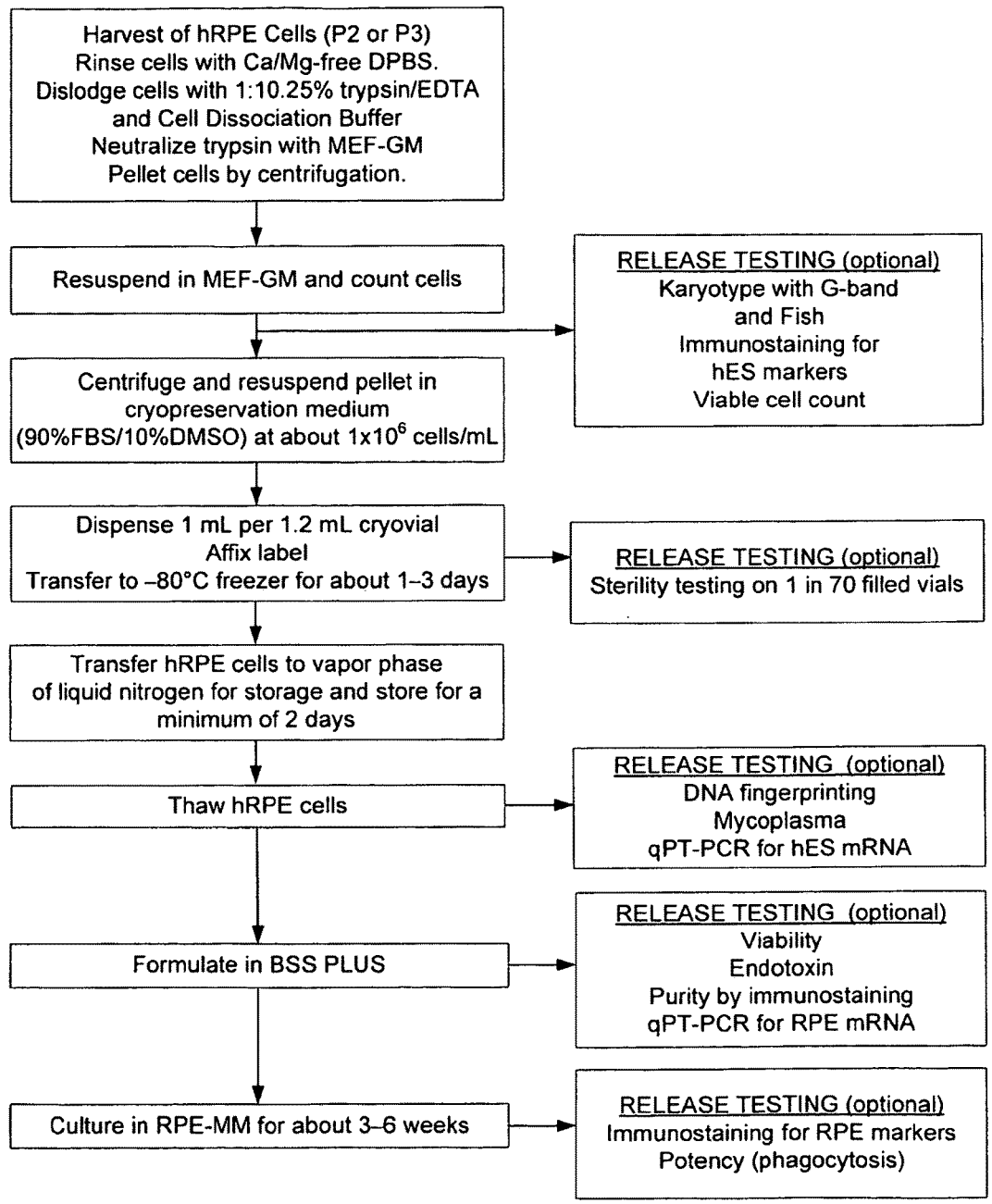

The EBs were then be transferred to gelatin-coated 6-well plates to allow for the outgrowth of RPEs. The initial growth medium is EB Outgrowth Medium, but once the EBs were attached this was changed to EB Maintenance Medium. See Table 2. When cultures were about 70% confluent the medium was changed to MDBK-MM. Once sufficient numbers of RPE cell clusters were visible, the RPE cells were isolated and further propagated in EGM-2 medium until confluent. When confluent the RPE cells were cultured in MDBK-MM until the cells reach a medium pigment morphology and pigmentation. See FIGS. 4 and 5. The RPE cells were then harvested and stored frozen at below about −135° C. (e.g., in the vapor phase of liquid nitrogen). See FIG. 6. The RPE cells were produced in compliance with GMP. Thus, this method yields an effective amount of human RPE cells suitable for use in transplantation.

Example 2

Seeding and Expansion of hES Cells

Figure 7:
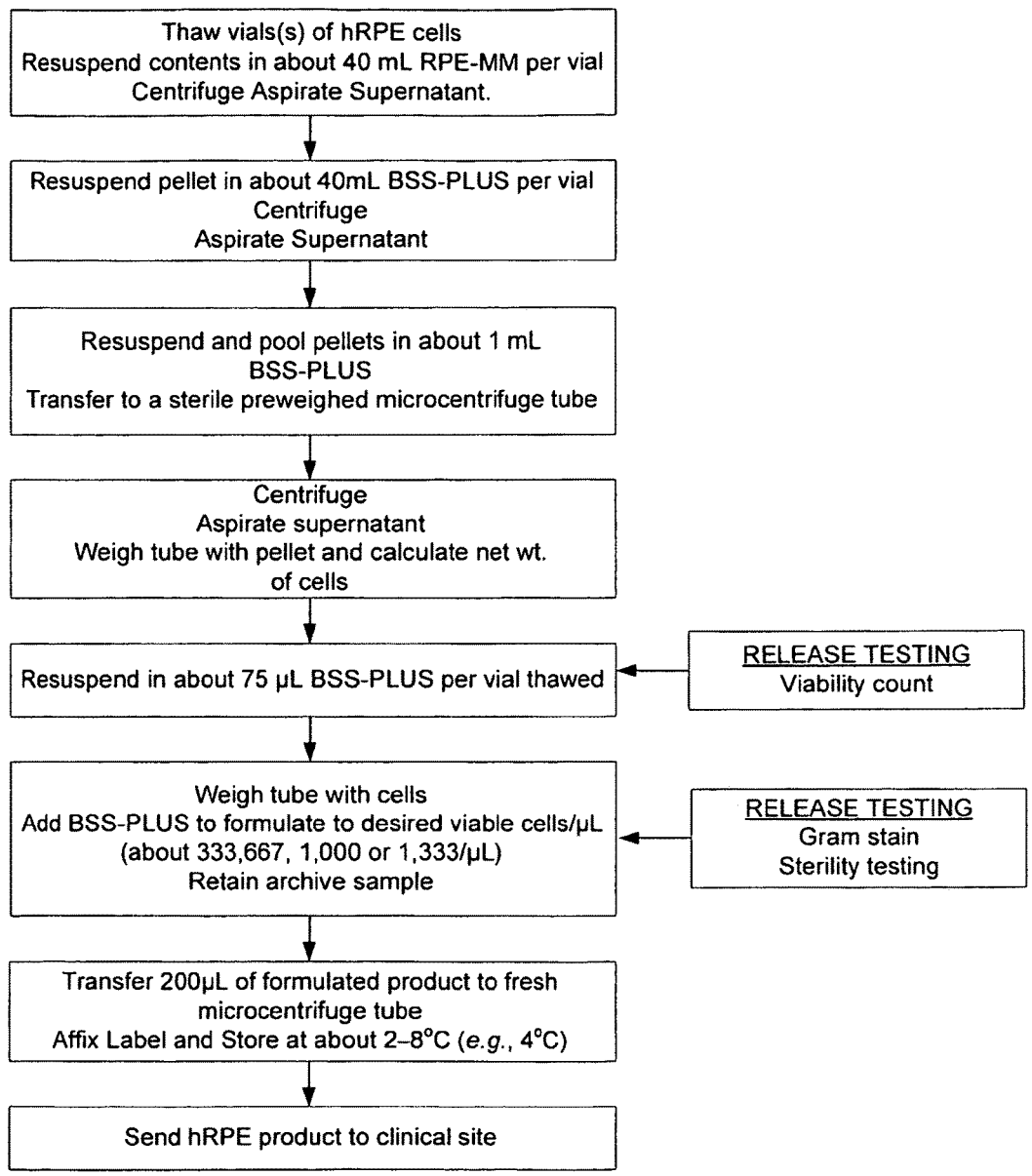

Cryopreserved human embryonic stem cells (hES) cells were thawed, washed with hES-GM, and inoculated onto the mitotically inactivated mouse embryonic feeder (MEF) cells in the gelatin-coated 6-well plates. See FIG. 7. The contents of each vial (~1 million cryopreserved cells) of hES were seeded into one well of a 6-well plate, and co-cultures of hES and MEF are incubated for about 4-9 days until about 60-80% confluent. During this time the cultures were examined microscopically: larger colonies displaying mostly hES morphology were dispersed into smaller pieces to prevent spontaneous differentiation. Mosaic colonies with large areas of undifferentiated cells were trimmed by removing those portions comprised of differentiated cells. Colonies containing predominately differentiated cells or non hES cell morphology were picked and discarded, using a stem cell cutting tool using photographs as a guide to the morphology of the colonies. See FIG. 2.

When 60-80% confluent, the hES cells were passaged by washing with $Ca^{2+}/Mg^{2+}$-free DPBS and treated with 0.05% trypsin/EDTA for about 2-5 minutes until detached. The trypsin was neutralized with MEF-GM and the cells collected by centrifugation. The hES cells are then reseeded on fresh MEF feeder layers. The hES cells were expanded several times at a split ratio of about 1:4 or less. See FIG. 3.

When a sufficient number of hES cells were propagated, hES cells were harvested. The cells were wash with $Ca^{2+}/Mg^{2+}$-free DPBS and treated with 0.05% trypsin/EDTA for about 2-5 minutes until detached. The trypsin was neutralized with MEF-GM and the cells collected by centrifugation. The hES cells were then resuspended in EB Formation Medium (EB-FM).

No additional MEF cells were used. The time between MEF removal and RPE cells harvest was 3 passages and about 80-90 days in MEF-free cell culture. The hES cell made by this method were further tested and confirmed to be substantially free of MEF cells by, for example, assaying for mouse specific markers. Upon testing of hES cell made by this method, it was found that the hES cells were substantially free of MEF cells.

Example 3

Human Embryoid Body Formation and Outgrowth hES cells were inoculated onto low-attachment, 6-well plates (at a split ratio of 1:2) and cultured for about 7-12 days until embryoid bodies were formed and matured. Embryoid bodies in suspension were harvested from the low attachment wells, resuspended in EB-FM, and plated onto gelatin-coated 6-well culture plates. The plates were cultured undisturbed for about 3-4 days to allow the embryoid bodies to attach. At this time, medium was changed to EB Growth Medium (EB-GM). When cultures were about 70% confluent (e.g., after about 9-12 days), the medium was changed to RPE Maintenance Medium (RPE-MM). See FIG. 3. Cell outgrowths from the attached EBs were sustained in culture in RPE-MM until the appropriate number of pigmented clusters were visible (e.g., after about 35-50 days after changing to RPE-MM). Thus, embryoid bodies were formed and isolated substantially free of non-human cells and thus not "xenotransplantation" material. These EB may then be differentiated to produce human RPE cells.

Example 4

Use of Cryopreserved hES Cells for Human Embryoid Bodies

Cryopreserved hES cells (e.g., MA01 and MA09) were thawed and placed into suspension culture on Lo-bind Nunclon Petri dishes in MDBK-Growth Medium or Optim-Pro SFM supplemented with L-Glutamine, Penicillin/Streptomycin, and B-27 supplement. The hES cells had been previously derived from single blastomeres biopsied from early cleavage stage human embryos. The remainder of the human embryo was not destroyed. The cells were cultured for at least about 7-14 days as embryoid bodies (EBs).

After at least about 7-14 days, the EBs were plated onto tissue culture plates coated with gelatin from porcine skin. The EBs were grown as adherent cultures for an at least about an additional 14-28 days in MDBK-Growth Medium or OptimPro SFM supplemented with L-Glutamine, and Penicillin/Streptomycin, without B-27 supplement. From amongst the cells in the adherent culture of EBs, RPE cells became visible and were recognized by their cobblestone cellular morphology and emergence of pigmentation. Therefore, cryopreserved hES cells may be thawed, cultured, and used to form EBs that may, in turn, be used to produce human RPE cells without the use of MEF cells.

Example 5

Human RPE Cell Derivation

Human RPE cell derivation was initiated when about 10-30 patches of light to dark brown clusters ~1 mm or less in diameter were visible in each well. This may require about 40-50 days after switching to RPE-MM. Embryoid body cellular outgrowths containing pigmented patches were harvested by incubating in Type IV collagenase in DPBS with $Ca^{2+}/Mg^{2+}$ until cell clusters have detached. The detached cell clusters were triple washed in RPE-MM and transferred to 100 mm non-tissue (ultra low attachment) culture dishes. Under a stereomicroscope, clusters of pigmented cells were mechanically separated from non-pigmented cell clusters using a stem cell cutting tool. Once all the pigmented clusters have been isolated, the collected clusters were examined under the stereomicroscope to remove any non-pigmented clusters that may have been transferred. Pigmented cell clusters were washed in RPE-MM and then dissociated in a 1:1 mix of 0.25% Trypsin-EDTA and Cell Dissociation Buffer. The dissociated cells were washed in MEF-GM to neutralize the trypsin and centrifuged. Cell pellets were resuspended in RPE Growth Medium (RPE-GM) before plating in gelatin-coated 6-well plates. See FIG. 4. Accordingly, cultures of human RPE cells that are substantially free of hES cells may be differentiated and isolated without the use of non-human feeder cells. Therefore, the human RPE cells prepared in accordance with the methods described herein may be considered substantially free of non-human cells, thus not a xenotransplantation material, and hES cells, thus not tumorigenic.

Example 6

Human RPE Expansion

Resuspended human RPE cells were inoculated onto gelatin-coated 4-well or 6-well plates at a density of 50,000 or 250,000 cells, respectively in RPE-GM and cultured until confluent (about 8-11 days). At this time, the medium was changed to RPE-MM and incubated for about 9-14 days until the RPE cultures display a medium level of pigmentation. Passage 0 (P0) RPE cultures were harvested with a 1:1 mix of 0.25% Trypsin-EDTA and Cell Dissociation Buffer, neutralized with MEF-GM and collected by centrifugation. Cell pellets were resuspended in RPE-GM and reinoculated onto gelatin-coated plates at a ratio of 1:3 to 1:6. RPE cell cultures were expanded at least twice (undergoing two 1:3 to 1:6 splits (passage 2 designation). At this time the human RPE cells were harvested. In this manner, the number of RPE cells may be greatly increased including to reach therapeutically useful amounts of human RPE cells (e.g., at least about $1 \times 10^3$-$10^6$ RPE cells).

Example 7

Propagation of Mature Human RPE Cells

RPE cells were cultured in an adherent culture. As differentiated RPE cells appear in the adherent cultures, clusters of differentiated RPEs may become visibly noticeable based on cell shape. Frozen collagenase IV (20 mg/ml) was thawed and diluted to 7 mg/ml. The collagenase IV was applied to the adherent culture containing RPE clusters (1.0 ml to each well in a 6-well plate). Over about 1-3 hours, the collagenase IV dissociated the cell clusters. By dissociating the RPE clusters from other cells in the culture, an enriched suspension of RPE cells was obtained. The enriched RPE cell suspension was removed from the culture plate and transferred to a 100 mm tissue culture dish with 10 ml of MEF medium. Pigmented clumps were transferred with a stem cell cutting tool (Swemed-Vitrolife) to a well of a 6-well plate containing 3 ml of MEF media. After all clumps have been picked up, the suspension of pigmented cells was transferred to a 15 ml conical tube containing 7 ml of MEF medium and centrifuged at 1000 rpm for five minutes. The supernatant was removed. 5 ml of a 1:1 mixture of 0.25% trypsin and cell dissociation buffer was added to the cells. The cells were incubated for 10 minutes at 37° C. The cells were dispersed by pipetting in a 5 ml pipette until few clumps were remaining. 5 ml of MEF medium was added to the cells and the cells centrifuged at 1000 rpm for 5 minutes. The supernatant was removed and the cells were plated on gelatin coated plates with a split of 1:3 of the original culture in EGM-2 culture medium. See FIG. 4.

The culture of RPE cells was expanded by continued culture in EGM-2 medium. The cells were passaged, as necessary, at a 1:3 to 1:6 ratio using a 1:1 mixture of 0.25% trypsin EDTA and Cell Dissociation Buffer. To enrich for mature differentiated RPE cells, the cells were grown to near confluency in EGM-2. The medium was then changed to MDBK-MM (SAFC Biosciences) to further promote maturation of the RPE cells. Accordingly, mature human RPE cells may be prepared for use in therapeutic methods.

Example 8

RPE Cells Harvest and Cryopreservation

The human RPE cells were grown to near confluency and the medium changed to RPE Maintenance Medium. The RPE cells were then cultured until the cells reach a medium pigment morphology and pigmentation. This may take at least about one additional month of culture time. The medium pigment is based on a culture that appears to contain about half of the cells in the dense cobblestone state and half the culture in the lighter, less dense morphology. Pictures may be utilized to help standardize the process. The medium pigment morphology was chosen because the viability post-thaw is maintained, the recovery of the cells is better than the high pigment, and the pharmacology showed similar efficacy to the other morphologies.

P2 or P3 medium-pigmented RPE cells in culture were harvested by washing and treatment with 0.25% Trypsin-EDTA. Detached RPE cells were washed with MEF-GM to neutralize the trypsin, centrifuged, counted and resuspended in a solution of 90% FBS and 10% DMSO at a concentration of 1 million cells/mL. One mL of cell product suspension was dispensed into an appropriately labeled, sterile, 1.2 mL cryovials. Vials were stored for 1-3 days at −80° C. prior to transfer to the vapor phase of liquid nitrogen storage (−135° C.) See FIG. 6. Thus the cryopreserved preparations of RPE cells may be manufactured.

Example 9

Compliance with GTP and/or GMP Regulations

Human RPE cells, either harvested or thawed from cryopreserved vials may be tested and characterized in compliance with GTP and/or GMP Regulations as presented in Table 3. See also 21 C.F.R. § 210 and § 211.

TABLE 3

Release Specifications for RPE cells

| Test | Method | Specification |
|---|---|---|
| Sterility | USP | Negative |
| Mycoplasma | Direct culture | Negative |
|  | Hoechst stain | Negative |
| Mouse DNA | PCR | Negative |
| Mouse Antibody Production | Inoculation into mice with LCMV challenge for antibodies to 19 viruses plus LDHE and LC viruses | Negative |
| Endotoxin | Endotoxin specific turbidimetric method | <0.50 EU/ml |
| In vitro viruses | Indicator Cells—cytopathic effect | Negative |
|  | Indicator Cells—hemadsorption | Negative |
|  | Indicator Cells—hemagglutination | Negative |
|  | Inoculation into suckling mice | Negative |
|  | Inoculation into adult mice | Negative |
|  | Inoculation into embryonated hen eggs allantoic route | Negative |
|  | Inoculation into embryonated hen eggs—yolk sac route | Negative |
| Viability | Trypan blue dye exclusion | >85% |
| Karyotype | G banding with FISH | Normal 46 XX |
| Morphology at harvest | Visual examination | Confluent, RPE morphology, medium pigmentation |
| Presence of RPE Markers Bestrophin RPE-65 CRALBP PEDF PAX6 MITF | qPCR | All present |
| Absence of hES markers Oct-4 NANOG Rex-1 Sox2 | qPCR | All absent |
| Presence of RPE Markers Bestrophin CRALBP PAX6 MITF ZO-1 | Immunostaining | All present |
| Absence of hES Markers Oct-4 Alkaline phosphatase | Immunostaining | All absent |
| Potency | Phagocytosis assay | Positive |
| Purity | Immunostaining for PAX6 and MITF | >95% staining for PAX6 and/or MITF |
|  | Immunostaining for PAX6 and bestrophin | >95% staining for PAX6 and/or bestrophin |
|  | Immunostaining for ZO-1 | >95% staining |
| Viability Prior to cryopreservation Post cryopreservation | Trypan blue exclusion | ≥85% ≥70% |

Table 4 provides a description of the tests that may be performed for characterization and qualification during the production of RPE cells including RPE cells preparations for use in transplantation therapies. The RPE cells produced in accordance with the methods described herein may be tested by at least one of the tests listed in Table 4.

TABLE 4

Description of Tests for Characterization and Qualification

| Test | Manufacturing Step Where Performed | Assay and Description |
| --- | --- | --- |
| Sterility | | |
| Sterility | Release of MEF cells<br>Release of hES seed bank<br>Release of hES MCB<br>(Master Cell Bank) | This assay may detect the presence of one or more species of bacterial and fungal contaminants in the test article. This determination is made using a membrane filtration meeting USP <71>. Bacteriostasis and fungistasis testing may also included. |
| Mycoplasma | | |
| Mycoplasma | Release of MEF cells<br>Release of hES seed bank<br>Release of hES MCB<br>Release of Product | This assay may be used to determine the presence of Mycoplasma in the test article based on the ability of Mycoplasma to grow in one of the test systems. In the direct culture procedure, broth and two types of agar plates are inoculated and incubated aerobically and microaerophilically. The inoculated broth bottles are subcultured on three separate occasions onto agar plates. All plates are examined for the presence of Mycoplasma colonies at least 14 days after inoculation. In addition the test article is inoculated into VERO cell cultures, incubated for three to five days and then stained using Hoechst DNA fluorochrome stain. These stained cultures are then examined microscopically. |
| Purity (Endotoxin) | | |
| Endotoxin | Release of Product | This assay may detect and quantify gram negative bacterial endotoxins (lipopolysaccharides) using an endotoxin specific turbidimetric method. After a minimum of 2 days in liquid nitrogen, product vials are thawed and formulated as per BR @ 1333 viable RPE/µL. |
| Purity (Other Contaminants) | | |
| Retrovirus detection using feline PG-4 (S*L) cells | Release of MEF cells<br>Release of hES MCB | This assay may detect replication competent retroviruses. In the direct assay the MEF cells are inoculated directly feline PG-4 (S*L) cells prepared in the presence of 4 µg/mL of polybrene and allowed to absorb for 60-90 minutes. After the absorption period, growth medium was added to the cells. And foci were enumerated on Day 5. In the amplified assay the test cells were inoculated into flasks of Mus Dunni cells treated with 8 µg/mL of polybrene. The cells are cultured for 14 days, with subpassage as needed. Culture fluids were harvested after the final sub pass and inoculated onto feline PG-4 (S*L) cells as described for the direct assay. |
| Viral reverse transcriptase detection | Release of MEF cells<br>Release of hES MCB | This assay may detect the presence of retroviruses by detecting viral reverse transcriptase activity using a PCR-based assay. If reverse transcriptase is present, RNA is reverse transcribed to cDNA. After reverse transcription, the samples are subjected to PCR and amplification monitored by fluorescence detection. The assay may detect as few as 55 viral particles. |
| Ultrastructural evaluation for virus-like particles | Release of MEF cells<br>Release of hES MCB | This assay may be used to examine 200 test article cells using transmission electron microscopy techniques to determine if virus-like particles are present. If retrovirus-like particles are present, the cells are evaluated for particle morphology (A, B, C, D, or R-type) and the number of cells with retrovirus-like particles is tabulated. |
| In vitro viral agents | Release of MEF<br>Release of hES MCB | This assay may be used to determine whether adventitious viral contaminants are present in cells by direct inoculation and observation of indicator cells for cytopathic effects, hemadsorption, and hemagglutination. The indicator cell lines used were MRC-5 (human diploid lung cells), Vero 76 (African green monkey kidney cells), and HeLa (human epithelioid carcinoma cells). This assay included sub-cultures for an additional 14 days. Hemagglutination and hemadsorption was tested using chicken, guinea pig and human O erythrocytes. |
| Detection of inapparent viruses | Release of MEF<br>Release of hES MCB | This assay may detect viruses present in the test article, which do not have a discernable effect in cell culture systems. The test article is inoculated into adult and suckling mice, guinea pigs, and embryonated hen's eggs (yolk sac and allantoic route). Suckling mice are subpassaged. All animals are observed for signs of illness and any that become sick are examined in an attempt to establish the cause of illness or death. Allantoic fluid and yolk sac are subpassaged. Both direct and subpassaged allantoic fluids are tested for hemagglutination temperature using guinea pig, human type O, and chick erythrocytes. Embryos may be examined for viability. |
| Detection of MVM | Release of MEF | This assay may detect the presence of MVM DNA sequences in the MEF cells. Genomic DNA was isolated from MEF cells. The DNA was amplified using PCR with primers and fluorescent probes specific for MVM and with fluorescence detection of amplification. |
| Murine ecotropic viruses | Release of hES MCB | This assay may detect the presence of infectious ecotropic murine leukemia retroviruses (E-MuLv). The assay utilizes a mixed culture of SC-1 cells (feral mouse) and XC cells (derived from a Wistar rat |

TABLE 4-continued

Description of Tests for Characterization and Qualification

| Test | Manufacturing Step Where Performed | Assay and Description |
|---|---|---|
| | | tumor induced by Rous Sarcoma virus). The assay is designed such that SC-1 cells (pretreated with polybrene). E-MuLv is capable of replicating in the SC-1 cells, however no morphological changes are observed. After several passages XC cells are placed in contact with the infected SC-1 cells. The XC undergo characteristic morphological changes (syncytium formation) due to E-MuLv infection. |
| Bovine viruses | Release of hES MCB | This assay may detect bovine viruses that may be cultured with BT (bovine turbinate) and Vero cells. The detection of these viruses is based upon microscopic observation of viral cytopathic effects in the indicator cells, immunofluorescent staining with virus-specific antibodies for viruses (bovine viral diarrhea virus, bovine parvovirus, bovine adenovirus, bovine respiratory syncytial virus, reovirus, blue tongue virus, and rabies virus), and a hemadsorption assay using chicken and guinea pig erythrocytes. |
| Porcine Viruses | Release of hES MCB | This assay may detect porcine viruses that may be by cultured with ST (swine testis) and Vero cells. The detection of these viruses is based upon microscopic observation of viral cytopathic effects in the indicator cells, immunofluorescent staining with virus-specific antibodies for viruses (bovine viral diarrhea virus, porcine parvovirus, porcine adenovirus, reovirus, transmissible gastroenteritis virus (also known as porcine coronavirus type 1), hemaggluting encephalitis virus, and rabies virus), and a hemadsorption assay using chicken and guinea pig erythrocytes. |
| HIV-1 virus | Release of hES MCB | This assay may detect the presence of HIV-1 sequences in the test article (genomic DNA, 0.5 μg) by PCR amplification using HIV-1-specific primers. The amplification products are then analyzed by fluorescence. |
| HIV-2 virus | Release of hES MCB | This assay may detect the presence of HIV-2 sequences in the test article (genomic DNA, 0.5 μg) by PCR amplification using HIV-2 -specific primers. The amplification products are then analyzed by fluorescence. |
| Human Cytomegalovirus | Release of hES MCB | This assay may detect the presence of CMV sequences in the test article (genomic DNA, 0.5 μg) by PCR amplification using CMV-specific primers. The amplification products are then analyzed The amplification products are then analyzed by fluorescence. |
| Human Parvovirus B19 | Release of hES MCB | This assay may detect the presence of HumanParvovirus B19 sequences in the test article (genomic DNA, 0.5 μg) by PCR amplification using Human Parvovirus B19-specific primers. The amplification products are then analyzed by fluorescence. |
| Human Epstein-Barr virus | Release of hES MCB | This assay may detect the presence of EBV sequences in the test article (genomic DNA, 0.5 μg) by PCR amplification using EBV-specific primers. The amplification products are then analyzed by fluorescence. |
| Human Hepatitis B virus | Release of hES MCB | This assay may detect the presence of HBV sequences in the test article (genomic DNA, 0.5 μg) by PCR amplification using HBV-specific primers. The amplification products may then be analyzed by fluorescence. |
| Human Hepatitis C Virus | Release of hES MCB | This assay may detect the presence of HCV sequences in the test article (genomic DNA, 0.5 μg) by PCR amplification using HCV-specific primers. The amplification products may then be analyzed by fluorescence. |
| Human Herpesvirus 6 Variant A (HHV-6A) and B (HHV-6B) | Release of hES MCB | This assay may detect the presence of HHV-6A and HHV-6B sequences in the test article (genomic DNA, 0.5 μg) by PCR amplification using HHV-6A and HHV-6B-specific primers. The amplification products may then be analyzed by fluorescence. |
| Human T-cell Lymphotropic Virus 1 and 2 (HTLV-1 and -2) | Release of hES MCB | This assay may detect the presence of HTLV-1 and HTLV-2 sequences in the test article (genomic DNA, 0.5 μg) by PCR amplification using HTLV-1 and HTLV-2-specific primers. The amplification products may then be analyzed by fluorescence. |
| Mouse antibody production | Release of hES MCB | This assay may detect the presence of murine viruses. The hES cells were administered to mice (intraperitoneally, intranasaly, and per os) on Day 1. Nine days later blood samples were collected from a subset for measurement of lactate dehydrogenase activity. On Day 23, a further subset of mice was challenged with a lethal dose of lymphocytic choriomeningitis virus (LCMV). Finally on Day 28 serum was collected from the remaining animals for assay of viral antibodies. Antibodies were detected by ELISA of IFA. |
| Cell Purity | Release of Product | This assay may detect the presence of RPE markers using immunostaining for MITF, PAX6 and DAPI. After cryopreservation, vials of Product may be thawed and formulated in the clinical diluent. The cells may then be centrifuged, resuspended in RPE-GM and plated onto gelatin-coated plates and cultured. The cells may be stained 1-3 days post-seeding. |

TABLE 4-continued

Description of Tests for Characterization and Qualification

| Test | Manufacturing Step Where Performed | Assay and Description |
|---|---|---|
| Identity | | |
| Gene Expression | Release of hES MCB | This assay may be used to determine the gene expression in the cells and compare to the morphological features Human Affymetrix HG-U133 Plus 2.0 microarray platform and performed subsequent informatic analysis |
| Karyotype | Release of hES MCB In process testing (hES Cell expansion) Release of Product | This assay may be used to confirm that the cells have maintained a normal chromosomal complement. It may be done using G-band staining with FISH |
| Morphology | In process. Release of Product | This assay may be used to confirm that the cells are of morphology consistent with RPE cells. |
| Presence of ES markers (q-PCR) | Release of hES MCB | This assay may detect the presence of ES markers Rex1, NANOG, TDGF-1, Sox-2, DPPA-2, DPPA-4 by RT-qPCR for RPE mRNA expression. The amplification products may then be analyzed by fluorescence. |
| Presence of RPE markers (q-PCR) | Release of Product | This assay may detect the presence of RPE markers bestrophin, RPE-65, CRALBP, PEDF, PAX6, MITF, ZO-1) by RT-qPCR for RPE mRNA expression. The amplification products may then be analyzed by fluorescence. After a minimum of 2 days in LN2, the cryopreserved product vials are thawed and formulated in the clinical diluent. RNA from the cells is extracted extract RNA used to generate cDNA and analyzed. |
| Presence of RPE markers (immunostaining) | Release of Product | This assay may detect lhe presence of RPE markers bestrophin, RPE-65, CRALBP, PEDF, PAX6, MITF, ZO-1) by immunostaining After a minimum of 2 days in LN2, the cryopreserved product vials are thawed and formulated in the clinical diluent. The cells may then be centrifuged, resuspended in RPE-GM and plated onto gelatin-coated plates and cultured. The cells may be stained 2-3 weeks after plating to mature into medium-pigmented RPE. |
| Absence of ES markers (q-PCR) | Release of Product | This assay may detect the absence of ES specific markers by PCR amplification. The amplification products may then be analyzed by fluorescence. After a minimum of 2 days in LN2, the cryopreserved product vials are thawed and formulated in the clinical diluent. RNA from the cells is extracted extract RNA used to generate cDNA and analyzed. |
| Absence of ES markers (immunostaining) | Release of Product | This assay may be used to confirm that no ES cells are absent in the Cell Product markers. Cells are collected prior to last centrifugation and addition of cryopreservation medium. The cells may be seeded into gelatin-coated and cultured until 30-60% confluent. The cells may then be stained. |
| Potency | | |
| Potency | Release of Product | This assay may be used to characterize the RPE product using a RPE-specific phagocytosis. Cells may be seeded in gelatin-coaled wells of a 96-well plate and grown in RPE-MM until medium-pigmented. The cells may then be incubated fluorescent polystyrene. The plates were incubated for 24-36 hours at 37° C. Negative control was performed with the same plates incubated at 1-4° C. for the same duration. After the incubation, the plates were rinsed 3 times with PBS to remove the remaining particles. fixed with 2% paraformaldehyde in PBS, rinsed twice with PBS and examined and photographed under the fluorescence inverted microscope. |
| Cell Viability | | |
| Viability | Harvest and cryo-preservation of Product | This assay may be used to measure the number of cells that have survived the manufacturing process using trypan blue exclusion. |
| Viability | Post thaw | After a minimum of 2 days in LN2, the cryopreserved product vials are thawed and formulated in the clinical diluent. The cells may then he centrifuged, resuspended in RPE-GM and plated onto gelatin-coated plates and cultured. The cells may be stained 2-3 weeks after plating to mature into medium-pigmented RPE. |

These assays were performed on representative cultures and preparations of human RPE cells and confirmed that the methods described herein yielded therapeutically useful amounts of human RPE cells that met the GTP and/or GMP standards. Further, the RPE cells described herein may comply with at least one of the standards recited in Tables 3 or 4. Therefore, the methods described herein may be used to produce therapeutically useful amounts of human RPE cells that meet GTP and/or GMP standards for use in therapeutic applications (e.g., treating retinal degeneration.)

Example 10

RPE Characterization and Testing

RPE cells may be seeded on gelatin. The RPE cells seeded on gelatin usually show loose pigmentation and epithelial morphology as they divide and migrate away from the initial attachment site. See, e.g., Klimanskaya, et al. (2004) *Cloning and Stem Cells* 6(3):1-29, FIG. 1. However, once confluency is reestablished, the RPE cells may revert to epithelial morphology and re-expressed pigment. See, e.g., id., FIG. 2. Various tests may be performed to confirm that the RPE cells maintain their RPE phenotype (e.g., phenotype stability) including RPE molecular markers, assaying for phagocytic activity, and confirming the absence of adventitious viruses. See, e.g., id.

RPE Molecular Markers

RPE cells express several characteristic RPE proteins in vivo, including bestrophin, RPE65, CRALBP, and PEDF. See, e.g., id., FIG. 3. Pigmented epithelial morphology of RPE-like differentiated derivatives of hES cells, may be lost in proliferating cultures and re-established upon reaching confluency as well as the presence of RPE molecular markers RPE65, CRALBP, bestrophin, and PEDF. Therefore, the RPE cells described herein are similar to natural RPE cells. See also id.

Phagocytosis Assay

Functional tests for characterization of the RPE cells include RPE-specific phagocytosis using an assay with labeled rod fragments or fluorescent *S. aurelius* particles. RPE cells provide functional support to photoreceptors through phagocytosis of shed photoreceptor fragments. Therefore, phagocytosis represents a major functional characteristic identifying RPE cells.

Approximately 500,000 formulated RPE cells may be seeded in gelatin-coated wells of a 4-well plate and cultured until medium-pigmentation is observed. The cells may then be incubated with fluorescent *S. aurelius* particles for at least about 24-36 hours at about 37° C. A negative control may be performed with the same plates incubated at about 1-4° C. for the same duration. After the incubation, the plates may be rinsed 3 times with PBS to remove the remaining particles, fixed with 2% paraformaldehyde in PBS, rinsed twice with PBS and examined and photographed under the fluorescence inverted microscope.

Human RPE cells produced according to the methods described herein are capable of phagocytosis of both latex beads and photoreceptor fragments.

Morphological Assessment

Manually-purified, hES cell-differentiated RPE in vitro may undergo significant morphological events in culture during the expansion phase. Single-cell suspensions plated in thin cultures depigment and cells tend to increase in surface area. The human RPE cells maintain this morphology during expansion when the cells are rapidly dividing. However, when cell density reaches maximal capacity, RPE may take on their characteristic phenotypic hexagonal shape and increase pigmentation level by accumulating melanin and lipofuscin.

Routine morphological assessment may be done using a phase contrast inverted light microscope throughout the duration of the production process. Digital microphotographs may be taken at key stages. Morphological assessment may be performed to confirm maintenance of the RPE phenotype. Human RPE produced according to the methods described herein show a stable RPE phenotype, lasting over 9 months. See Example 19.

Karyotyping

Karyotyping (e.g., by G-banding and FISH) may be performed to ensure that only cells maintain a normal ploidy (e.g., 46 chromosomes for humans). This karyotype analysis may be performed after harvest and seeding of hES cells for EB formation, after seeding of the P1 passage of RPE cells, and at the harvest of the RPE cells described herein prior to cryopreservation, for example. Human RPE produced according to the methods described herein show a stable karyotype (e.g., 46 chromosomes for humans). See Table 1.

Adventitious Viruses

In order to confirm the absence of viral contamination RPE cells, a batch of RPE cells (RPE MA09p32) were prepared in accordance with the methods described herein. The RPE cells were passaged an additional two times prior to harvest and testing for viruses, to ensure that any virus is given the maximum chance to be expressed. At passage 4, RPE MA09p32+4 cells were harvested and tested for inapparent viruses and in vitro viruses. A portion of the cells was passaged one further time (lot RPE MA09p32+5) before being sent for ultrastructural evaluation of viral particles. These cells were substantially free of viral contamination indicating that the manufacture of RPE cells does not result in hidden viruses.

Stability Testing

To verify the RPE cells may produce the desired characteristics after cryopreservation, vials of the RPE cells may thawed and characterized. The RPE cells may then be tested 1, 2, 3, 6, 12, 18 and 24 months post freeze. A vial of RPE cells were prepared, cryopreserved, and thawed then tested. These RPE cells showed a normal, 46 chromosome (XX) karyotype†, was viable, substantially free from viruses, and viable after 6-9 months of cryostorage. Additionally, the RPE cells showed a normal, 46 chromosome (XX) karyotype†, was viable, substantially free from viruses, and viable after 1-4 years of cryostorage.

†These RPE cells were derived from the female human embryonic stem cell line MA09. See Klimanskaya, et al. (2007) *Nat. Protoc.* 2(8): 1963-72 and Klimanskaya, et al. (2006) *Nature* 444(7118): 481-5.

Example 11

Microarray Gene Expression Profiling of RPE Cells

A global gene expression analysis via microarray was performed on the human RPE cells derived from both of the single blastomere-derived hES cell lines MA01 and MA09 to test for the presence of RPE markers and the absence of ES markers. Additionally, fetal RPE, ARPE-19, and retinoblastoma cell lines were analyzed as controls.

The data indicates that this phenotypic change to RPE is driven by a change in the global gene expression pattern of these cells, specifically with regard to the expression of PAX6, PAX2, Otx2, MitF, and Tyr. Based on ANOVA analysis comparing the respective hES cell line to its RPE counterpart, we selected the 100 highest and lowest expressed genes, and performed computational analysis to select genes related to pluripotency and eye development. Upregulated genes are shown in Table 5. Downregulated genes are shown in Table 6.

TABLE 5

Upregulated genes of interest reported on microarrays

| Gene Symbol | Gene Name | Associated with | Description |
| --- | --- | --- | --- |
| BEST1/VMD2 | bestrophin (vitelliform macular dystrophy 2) | RPE development | Predominantly expressed in the basolateral membrane of the retinal pigment epithelium. forms calcium-sensitive chloride channels. May conduct other physiologically significant anions such as bicarbonate. Defects in BEST1 are the cause of vitelliform macular dystrophy type 2 (VMD2); also known as Best macular dystrophy (BMD). VMD2 is an autosomal dominant form of macular degeneration that usually begins in childhood or adolescence. VMD2 is characterized by typical "egg-yolk" macular lesions due to abnormal accumulation of lipofuscin within and beneath the retinal pigmented epithelium cells. Progression of the disease leads to destruction of the retinal pigmented epithelium and vision loss. Defects in BEST1 are a cause of adult-onset vitelliform macular dystrophy (AVMD). AVMD is a rare autosomal dominant disorder with incomplete penetrance and highly variable expression. Patients usually become symptomatic in the fourth or fifth decade of life with a protracted disease of decreased visual acuity. |
| CLUL1 (retinal) | clusterin-like 1 (retinal) | retinal development | Associated strongly with cone photoreceptors and appears in different tissues throughout retinal development. |
| CRX | cone-rod homeobox | retinal development | Phosphoreceptor (cone, rod) specific paired-like homeo domain protein, expressed in developing and mature phosphoreceptor cells, binding and transactivating rhodopsin, homolog to Drosophila orthodenticle (Otx). Essential for the maintenance of mammalian photoreceptors. |
| CRYAA | Crystallin, alpha A | eye development | Crystallins are the dominant structural components of the vertebrate eye lens. May contribute to the transparency and refractive index of the lens. Defects in CRYAA are the cause of zonular central nuclear cataract one of a considerable number of phenotypically and genotypically distinct forms of autosomal dominant cataract. This congenital cataract is a common major abnormality of the eye that frequently causes blindness in infants. Crystallins do not turn over as the lens ages, providing ample opportunity for post-translational modifications or oxidations. These modifications may change crystallin solubility properties and favor senile cataract. |
| CRYBA1 | crystallin, beta A1 | eye development | Crystallins are the dominant structural components of the vertebrate eye lens. Crystallins do not turn over as the lens ages, providing ample opportunity for post-translational modifications or oxidations. These modifications may change crystallin solubility properties and favor senile cataract. |
| CRYBA2 | crystallin, beta A2 | eye development | Crystallins are the dominant structural components of the vertebrate eye lens. Crystallins do not turn over as the lens ages, providing ample opportunity for post-translational modifications or oxidations. These modifications may change crystallin solubility properties and favor senile cataract. |
| CRYBA4 | crystallin, beta A4 | eye development | Crystallins are the dominant structural components of the vertebrate eye lens. Defects in CRYBA4 are the cause of lamellar cataract 2. Cataracts are a leading cause of blindness worldwide, affecting all societies. A significant proportion of cases are genetically determined. More than 15 genes for cataracts have been identified, of which the crystallin genes are the most commonly mutated. Lamellar cataract 2 is an autosomal dominant congenital cataract. Defects in CRYBA4 are a cause of isolated microphthalmia with cataract 4 (MCOPCT4). Microphthalmia consists of a development defect causing moderate or severe reduction in size of the eye. Opacities of the cornea and lens, scaring of the retina and choroid, and other abnormalities like cataract may also be present Crystallins do not turn over as the lens ages, providing ample opportunity for post-translational modifications or oxidations. These modifications may change crystallin solubility properties and favor senile cataract. |

TABLE 5-continued

Upregulated genes of interest reported on microarrays

| Gene Symbol | Gene Name | Associated with | Description |
| --- | --- | --- | --- |
| CRYBB1 | crystallin, beta B1 | eye development | Crystallins are the dominant structural components of the vertebrate eye lens. |
| CRYBB2 | crystallin, beta B2 | eye development | Crystallins are the dominant structural components of the vertebrate eye lens. Defects in CRYBB2 are the cause of congenital cerulean cataract 2 (CCA2); also known as congenital cataract blue dot type 2. CCA2 is a form of autosomal dominant congenital cataract (ADCC). Cerulean cataracts have peripheral bluish and white opacifications in concentric layers with occasional central lesions arranged radially. Although the opacities may be observed during fetal development and childhood, usually visual acuity is only mildly reduced until adulthood, when lens extraction is generally necessary. Defects in CRYBB2 are the cause of sutural cataract with punctate and cerulean opacities (CSPC). The phenotype associated with this form of autosomal dominant congenital cataract differed from all other forms of cataract reported. Defects in CRYBB2 are a cause of Coppock-like cataract (CCL). Crystallins do not turn over as the lens ages, providing ample opportunity for post-translational modifications or oxidations. |
| CRYBB3 | crystallin, beta B3 | eye development | Crystallins are the dominant structural components of the vertebrate eye lens. Defects in CRYBB3 are the cause of autosomal recessive congenital nuclear cataract 2 (CATCN2); a form of non-syndromic congenital cataract. Non-syndromic congenital cataracts vary markedly in severity and morphology, affecting the nuclear, cortical, polar, or subcapsular parts of the lens or, in severe cases, the entire lens, with a variety of types of opacity. They are one of the major causes of vision loss in children worldwide and are responsible for about one third of blindness in infants. Congenital cataracts can lead to permanent blindness by interfering with the sharp focus of light on the retina during critical developmental intervals. Crystallins do not turn over as the lens ages, providing ample opportunity for post-translational modifications or oxidations. These modifications may change crystallin solubility properties and favor senile cataract. |
| DCT/TYRP2 | dopachrome tautomerase (dopachrome delta-isomerase, tyrosine-related protein 2) | pigmented cells | Tyrosine metabolism and Melanin biosynthesis. |
| LHX2 | LIM homeobox 2 | development/differentiation | Transcriptional regulatory protein involved in the control of cell differentiation in developing lymphoid and neural cell types. |
| LIM2 | lens intrinsic membrane protein 2, 19kDa | eye development | Present in the thicker 16-17 nm junctions of mammalian lens fiber cells, where it may contribute to cell junctional organization. Acts as a receptor for calmodulin. May play an important role in both lens development and cataractogenesis. |
| MITF | microphthalmia-associated transcription factor | RPE development | Transcription factor for tyrosinase and tyrosinase-related protein 1. Binds to a symmetrical DNA sequence (E-boxes) (5'-CACGTG-3') found in the tyrosinase promoter. Plays a critical role in the differentiation of various cell types as neural crest-derived melanocytes, mast cells, osteoclasts and optic cup-derived retinal pigmented epithelium. Highly expressed in retinal pigmented epithelium. |
| OCA2 | oculocutaneous albinism II (pink-eye dilution homolog, mouse) | pigmented cells | Could be involved in the transport of tyrosine, the precursor to melanin synthesis, within the melanocyte. Regulates the pH of melanosome and the melanosome maturation. One of the components of the mammalian pigmentary system. Seems to regulate the postranslational processing of tyrosinase, which catalyzes the limiting reaction in melanin synthesis. May serve as a key control point at which ethnic skin color variation is determined. Major determinant of brown and/or blue eye |

TABLE 5-continued

Upregulated genes of interest reported on microarrays

| Gene Symbol | Gene Name | Associated with | Description |
|---|---|---|---|
| | | | color. Defects in OCA2 are the cause of oculocutaneous albinism type II (OCA2). OCA2 is an autosomal recessive form of albinism, a disorder of pigmentation in the skin, hair, and eyes. The phenotype of patients with OCA2 is typically somewhat less severe than in those with tyrosinase-deficient OCA1. There are several forms of OCA2, from typical OCA to relatively mild 'autosomal recessive ocular albinism' (AROA). OCA2 is the most prevalent type of albinism throughout the world. The gene OCA2 is localized to chromosome 15 at 15q 11.2-q12 |
| OPN3 | opsin 3 | eye development | May play a role in encephalic photoreception. Strongly expressed in brain. Highly expressed in the preoptic area and paraventricular nucleus of the hypothalamus. Shows highly patterned expression in other regions of the brain, being enriched in selected regions of the cerebral cortex, cerebellar Purkinje cells, a subset of striatal neurons, selected thalamic nuclei, and a subset of interneurons in the ventral horn of the spinal cord. |
| OPN5 | opsin 5 | eye development | Associated with visual perception and phototransduction. |
| OTX2 | orthodenticle homolog 2 (*Drosophila*) | retinal development | Probably plays a role in the development of the brain and the sense organs. Defects in OTX2 are the cause of syndromic microphthalmia 5 (MCOPS5). Microphthalmia is a clinically heterogeneous disorder of eye formation, ranging from small size of a single eye to complete bilateral absence of ocular tissues. Up to 80% of cases of microphthalmia occur in association with syndromes that include non-ocular abnormalities such as cardiac defects, facial clefts, microcephaly and hydrocephaly. MCOPS5 patients manifest unilateral or bilateral microphthalmia/clinical anophthalmia and variable additional features including coloboma, microcornea, cataract, retinal dystrophy, hypoplasia or agenesis of the optic nerve, agenesis of the corpus callosum, developmental delay, joint laxity, hypotonia, and seizures. |
| PAX6 | paired box gene 6 (aniridia, keratitis) | RPE development | Transcription factor with important functions in the development of the eye, nose, central nervous system and pancreas. Required for the differentiation of pancreatic islet alpha cells (By similarity). Competes with PAX4 in binding to a common element in the glucagon, insulin and somatostatin promoters (By similarity). Isoform 5a appears to function as a molecular switch that specifies target genes. Defects in PAX6 results in a number of eye defects and malformations. |
| PHC2 | polyhomeotic-like 2 (*Drosophila*) | development/ differentiation | Component of the Polycomb group (PcG) multiprotein PRC1 complex, a complex required to maintain the transcriptionally repressive state of many genes, including Hox genes, throughout development. PeG PRC1 complex acts via chromatin remodeling and modification of histones: it mediates monoubiquitination of histone H2A 'Lys-119', rendering chromatin heritably changed in its expressibility. |
| PKNOX2 | PBX/knotted 1 homeobox 2 | development/ differentiation | Known to be involved in development and may, along with MEIS, control PAX6. |
| PRKCA | protein kinase C, alpha | cellular signaling | Very important for cellular signaling pathways such as the MAPK, Wnt, P13, VEGF and Calcium pathways. |
| PROX1 | prospero-related homeobox 1 | eye development | May play a fundamental role in early development of CNS. May regulate gene expression and development of postmitotic undifferentiated young neurons. Highly expressed in lens, retina, and pancreas. |
| PRRX1 | paired related homeobox 1 | development/ differentiation | Necessary for development. Transcription coactivator, enhancing the DNA-binding activity of serum response factor. |
| RAI1 | retinoic acid induced 1 | development/ differentiation | May function as a transcriptional regulator. Regulates transcription through chromatin remodeling by interacting with other proteins in chromatin as well as |

TABLE 5-continued

Upregulated genes of interest reported on microarrays

| Gene Symbol | Gene Name | Associated with | Description |
|---|---|---|---|
| | | | proteins in the basic transcriptional machinery. May be important for embryonic and postnatal development. May be involved in neuronal differentiation. |
| RARA | retinoic acid receptor, alpha | development/ differentiation | This is a receptor for retinoic acid. This metabolite has profound effects on vertebrate development. This receptor controls cell function by directly regulating gene expression. |
| RARB | retinoic acid receptor, beta | development/ differentiation | This is a receptor for retinoic acid. This metabolite has profound effects on vertebrate development. This receptor controls cell function by directly regulating gene expression. |
| RARRES1 | retinoic acid receptor responder (tazarotene induced) 1 | development/ differentiation | Associated with differentiation and control of cell proliferation. May be a growth regulator that mediates some of the growth suppressive effects of retinoids. |
| RAX | retina and anterior neural fold homeobox | eye development | Plays a critical role in eye formation by regulating the initial specification of retinal cells and/or their subsequent proliferation. Binds to the photoreceptor conserved element-I (PCE-1/Ret 1) in the photoreceptor cell-specific arrestin promoter. |
| RB1 | retinoblastoma 1 (including osteosarcoma) | development/ differentiation | An important regulator of other genes and cell growth. Defects in RBI are the cause of childhood cancer retinoblastoma (RB). RB is a congenital malignant tumor that arises from the nuclear layers of the retina. |
| RDH5 | retinol dehydrogenase 5 (11-cis/9-cis) | RPE development | retinol dehydrogenase 5, 11-cis, expressed in retinal pigmented epithelium, formerly RDH 1. Stereospecific 11-cis retinol dehydrogenase, which catalyzes the final step in the biosynthesis of 11-cis retinaldehyde, the universal chromophore of visual pigments: Abundant in the retinal pigmented epithelium. Defects in RDH5 are a cause of fundus albipunctatus (FA). FA is a rare form of stationary night blindness characterized by a delay in the regeneration of cone and rod photopigments. |
| RGR | retinal G protein coupled receptor | RPE development | Preferentially expressed at high levels in the retinal pigmented epithelium (RPE) and Mueller cells of the neural retina. Retinal opsin related, (rhodopsin homolog)expressed in the retinal pigmented epithelium, encoding a retinaldehyde, preferentially all-trans retinal, binding protein, G protein coupled receptor superfamily. |
| RLBP1/ CRALBP1 | retinaldehyde binding protein 1 | RPE development | Carries I 1-cis-retinol and 11-cis-retinaldehyde as endogenous ligands and may be a functional component of the visual cycle. Defects in RLBP1 are a cause of autosomal recessive retinitis pigmentosa (arRP). Retinitis pigmentosa (RP) leads to degeneration of retinal photoreceptor cells. dystrophy, also known as Vasterbotten dystrophy. It is another form of autosomal recessive retinitis pigmentosa. Defects in RLBP1 are the cause of Newfoundland rod-cone dystrophy (NFRCD). NFRCD is a retinal dystrophy reminiscent of retinitis punctata albescens but with a substantially lower age at onset and more-rapid and distinctive progression. |
| RPE65 | retinal pigment epithelium- specific protein 65kDa | RPE development | Retinal pigmented epithelium specific. Retinal pigmented epithelium-specific 65, major microsomal protein, minor role in the isomerisation of all-trans to 11-cis retinal, associated with the endoplasmic reticulum, also expressed in renal tumor cells. Plays important roles in the production of 11-cis retinal and in visual pigment regeneration. |
| RRH | retinal pigment epithelium- derived rhodopsin homolog | RPE development | Found only in the eye, where it is localized to the retinal pigment epithelium (RPE). In the RPE, it is localized to the microvilli that surround the photoreceptor outer segments. May play a role in rpe physiology either by detecting light directly or by monitoring the concentration of retinoids or other photoreceptor-derived compounds. |

TABLE 5-continued

Upregulated genes of interest reported on microarrays

| Gene Symbol | Gene Name | Associated with | Description |
| --- | --- | --- | --- |
| RTN 1 | reticulon 1 | development/ differentiation | Expressed in neural and neuroendocrine tissues and cell cultures derived therefrom. Expression of isoform RTN1-C is strongly correlated with neuronal differentiation. |
| RXRB | retinoid X receptor, beta | development/ differentiation | Nuclear hormone receptor. Involved in the retinoic acid response pathway. Binds 9-cis retinoic acid (9C-RA), obligate member of heterodimeric nuclear receptors. steroid/thyroid/retinoic receptor superfamily. |
| RXRG | retinoid X receptor, gamma | development/ differentiation | Nuclear hormone receptor. Involved in the retinoic acid response pathway. Binds 9-cis retinoic acid (9C-RA), obligate member of heterodimeric nuclear receptors. steroid/thyroid/retinoic receptor superfamily. |
| SERPINF1/ PEDF | serpin peptidase inhibitor, clade F (alpha-2 antiplasmin, pigment epithelium derived factor), member 1 | RPE development | Specific expression in retinal pigment epithelial cells and blood plasma. Neurotrophic protein; induces extensive neuronal differentiation in retinoblastoma cells. |
| SIX3 | sine oculis homeobox homolog 3 (*Drosophila*) | eye development | Expressed during eye development in midline forebrain and in anterior region of the neural plate especially inner retina and later in ganglion cells and in cells of the inner nuclear layer, involved in regulation of eye development. |
| SOX10 | SRY (sex determining region Y)-box 10 | development/ differentiation | Transcription factor that seems to function synergistically with other development associated proteins. Could confer cell specificity to the function of other transcription factors in developing and mature glia. |
| SOX5 | SRY (sex determining region Y)-box 5 | development/ differentiation | Expression is associated with craniofacial, skeletal and cartilage development and is highly expressed in brain, testis and various tissues. |
| SOX6 | SRY (sex determining region Y)-box 6 | development/ differentiation | Expression is associated with craniofacial, skeletal and cartilage development and is highly expressed in brain, testis and various tissues. |
| SOX8 | SRY (sex determining region Y)-box 8 | development/ differentiation | May play a role in central nervous system, limb and facial development |
| SOX9 | SRY (sex determining region Y)-box 9 (campomelic dysplasia, autosomal sex-reversal) | development/ differentiation | Plays an important role in the normal development. May regulate the expression of other genes involved for skeletal and cartilage formation by acting as a transcription factor for these genes. |
| TIMP3 | TIMP metallopeptidase inhibitor 3 (Sorsby fundus dystrophy, pseudoinflam matory) | RPE development | Matrix metalloproteinase, tissue inhibitor 3, expressed in retinal pigment epithelium, placenta, localized in extracellular matrix. Complexes with metalloproteinases (such as collagenases) and irreversibly inactivates them. May form part of a tissue-specific acute response to remodeling stimuli. Defects in TIMP3 are the cause of Sorsby fundus dystrophy (SFD). SFD is a rare autosomal dominant macular disorder with an age of onset in the fourth decade. It is characterized by loss of central vision from subretinal neovascularization and atrophy of the ocular tissues. |
| TTR | transthyretin (prealbumin, amyloidosis type I) | | Thyroid hormone-binding protein. Probably transports thyroxine from the bloodstream to the brain. Defects in TTR are the cause of amyloidosis VII; also known as leptomeningeal amyloidosis or meningocerebrovascular amyloidosis. Leptomeningeal amyloidosis is distinct from other forms of transthyretin amyloidosis in that it exhibits primary involvement of the central nervous system. Neuropathologic examination shows amyloid in the walls of leptomeningeal vessels, in pia arachnoid, |

TABLE 5-continued

Upregulated genes of interest reported on microarrays

| Gene Symbol | Gene Name | Associated with | Description |
|---|---|---|---|
| | | | and subpial deposits. Some patients also develop vitreous amyloid deposition that leads to visual impairment (oculoleptomeningeal amyloidosis). |
| TYR | tyrosinase (oculocutaneous albinism 1A) | pigmented cells | This is a copper-containing oxidase that functions in the formation of pigments such as melanins and other polyphenolic compounds. Defects in TYR are the cause of oculocutaneous albinism type IA (OCA-IA). OCA-I, also known as tyrosinase negative oculocutaneous albinism, is an autosomal recessive disorder characterized by absence of pigment in hair, skin and eyes. OCA-I is divided into 2 types: type IA, characterized by complete lack of tyrosinase activity due to production of an inactive enzyme, and type IB characterized by reduced activity of tyrosinase. OCA-IA patients presents with the lifelong absence of melanin pigment after birth and manifest increased sensitivity to ultraviolet radiation and to predisposition to skin cancer defects in TYR are the cause of oculocutaneous albinism type IB (OCA-IB); also known as albinism yellow mutant type. OCA-IB patients have white hair at birth that rapidly turns yellow or blond. |
| TYRP1 | tyrosinase-related protein 1 | pigmented cells | Specific expression in Pigment cells. Oxidation of 5,6-dihydroxyindole-2-carboxylic acid (DHICA) into indole-5, 6-quinone-2-carboxylic acid. May regulate or influence the type of melanin synthesized. Defects in TYRP1 are the cause of rufous oculocutaneous albinism (ROCA). ROCA occurs in blacks and is characterized by bright copper-red coloration of the skin and hair and dilution of the color of the iris. Defects in TYRP1 are the cause of oculocutaneous albinism type III (OCA-III); also known as OCA3. OCA-III is a form of albinism with only moderate reduction of pigment. Individuals with OCA-III are recognized by their reddish skin and hair color. |

TABLE 6

Downregulated genes of interest reported on microarrays

| Gene Symbol | Gene Name | Associated with | Description |
|---|---|---|---|
| ALPL | alkaline phosphatase | ES cells | Elevated expression of this enzyme is associated with undifferentiated pluripotent stem cell. |
| CECR2 | cat eye syndrome chromosome region, candidate 2 | | Part of the CERF (CECR2-containing-remodeling factor) complex, which facilitates the perturbation of chromatin structure in an ATP-dependent manner. May be involved through its interaction with LRPPRC in the integration of cytoskeletal network with vesicular trafficking, nucleocytosolic shuttling, transcription, chromosome remodeling and cytokinesis. Developmental disorders are associated with the duplication of the gene. |
| DCAMKL1 | doublecortin and CaM kinase-like 1 | Embryonic development | Probable kinase that may be involved in a calcium-signaling pathway controlling neuronal migration in the developing brain. |
| DPPA2 | developmental pluripotency associated 2 | ES cells | May play a role in maintaining cell pluripotentiality. |
| DPPA3 | developmental pluripotency associated 3 | ES cells | May play a role in maintaining cell pluripotentiality. |
| DPPA4 | developmental pluripotency associated 4 | ES cells | May indicate cell pluripotentiality. |
| DPPA5/Esg1 | developmental pluripotency associated | ES cells | Embryonic stem cell marker. |

TABLE 6-continued

Downregulated genes of interest reported on microarrays

| Gene Symbol | Gene Name | Associated with | Description |
|---|---|---|---|
| FOXD3 | 5/Embryonic stem cell specific gene 1 forkhead box D3 | Pluripotence | Required for maintenance of pluripotent stem cells in the pre-implantation and peri-implantation stages of embryogenesis. |
| LITDIECAT11 | LINE-1 type transposase domain containing 1/ES cell associated transcript 11 | ES cells | Embryonic stem cell marker. |
| NANOG | NANOG homeobox | ES cells | Embryonic stem cell marker. Transcription regulator involved in inner cell mass and embryonic stem (ES) cells proliferation and self-renewal. Imposes pluripotency on ES cells and prevents their differentiation towards extraembryonic endoderm and trophectoderm lineages. |
| NCAM1 | neural cell adhesion molecula 1 | neuroprogenitors | This protein is a cell adhesion molecule involved in neuron-neuron adhesion, neurite fasciculation, outgrowth of neurites, etc. |
| NES/Nestin | nestin | ES cells | Neuralprogenitor cells. |
| NODAL | nodal | Embryonic development | Essential for mesoderm formation and axial patterning during embryonic development. |
| NR5A2/FTF | nuclear receptor subfamily 5, group A, member 2 | Embryonic development | May contribute to the development and regulation of liver and pancreas-specific genes and play important roles in embryonic development. |
| POU5Fl/ Oct-3/4 | POU domain, class 5, transcription factor 1 | ES cells | Embryonic stem cell marker. Indicator of "Sternness". Transcription factor that binds to the octamer motif (5'-ATITGCAT-3'). Prime candidate for an early developmental control gene. |
| SOX17 | SRY (sex determining region Y)-box 17 | Inhibitor of differentiation | Negative regulator of the Wnt signaling pathway. |
| SOX2 | SRY (sex determining region Y)-box 2 | ES cells | Indicator of "Sternness". Expressed in inner cell mass, primitive ectoderm and developing CNS. |
| TBX3 | T-box 3 (ulnar mammary syndrome) | Embryonic development | Transcriptional repressor involved in developmental processes. Murine T-box gene Tbx3 (T, brachyury) homolog, putative transcription factor, pairing with TBX5, homolog to Drosophila optomotor-blind gene (omb), involved in optic lobe and wing development, involved in developmental regulation, expressed in anterior and posterior mouse limb buds, widely expressed in adults |
| TDGFl/Cripto-1 | teratocarcinoma-derived growth factor 1 | ES cells | Indicator of "Sternness". Could play a role in the determination of the epiblastic cells that subsequently give rise to the mesoderm. |
| TEK/VMCM | TEK tyrosine kinase, endothelial (venous malformations, multiple cutaneous and mucosal) | Early Endothelial progenitors | This protein is a protein tyrosine-kinase transmembrane receptor for angiopoietin 1. It may constitute the earliest mammalian endothelial cell lineage marker. Probably regulates endothelial cell proliferation, differentiation and guides the proper patterning of endothelial cells during blood vessel formation |
| TUBB2A, TUBB2B | tubulin, beta 2A, tubulin, beta 2B | neuroprogenitors | Tubulin is the major constituent of microtubules. It binds two moles of GTP, one at an exchangeable site on the beta chain and one at a non-exchangeable site on the alpha-chain. Often associated with the formation of gap junctions in neural cells. |
| TUBB2A, TUBB2B, TUBB2C, TUBB3, TUBB4 | tubulin, beta 2A, tubulin, beta 2B, tubulin, beta 2C, tubulin, beta 3, tubulin, beta 4 | neuroprogenitors | Tubulin is the major constituent of microtubules. It binds two moles of GTP, one at an exchangeable site on the beta chain and one at a non-exchangeable site on the alpha-chain. Often associated with the formation of gap junctions in neural cells. |
| TUBB3 | tubulin, beta 3 | neuroprogenitors | Tubulin is the major constituent of microtubules. It hinds two moles of GTP, one at an exchangeable site on the beta chain and one at a non-exchangeable |

TABLE 6-continued

Downregulated genes of interest reported on microarrays

| Gene Symbol | Gene Name | Associated with | Description |
|---|---|---|---|
| | | | site on the alpha-chain. Often associated with the formation of gap junctions in neural cells. |
| TWIST1 | twist homolog 1 | Inhibitor of differentiation | Probable transcription factor, which negatively regulates cellular determination and differentiation. |
| UTF1 | undifferentiated embryonic cell transcription factor 1 | ES cells | Embryonic stem cell marker. Acts as a transcriptional coactivator of ATF2. |
| VSNL1 | visinin-like 1 | Inhibitor of rhodopsin | Regulates the inhibition of rhodopsin phosphorylation. |
| ZFP42/Rex-1 | zinc finger protein 42 | ES cells | Embryonic Stem cell marker. |

The results of the microarray assay demonstrates that RPE cells made by the methods described herein express multiple genes that are not expressed by hES cells, fetal RPE cells, or ARPE-19 cells. The distinctive molecular fingerprint of mRNA and protein expression in the ES-cell derived RPE cells of the invention constitutes a set of markers, such as RPE-65, Bestrophin, PEDF, CRABLP, Otx2, Mit-F, PAX6 and PAX2, that make these RPE cells distinct from cells in the art, such as hES cells, ARPE-19 cells, and fetal RPE cells.

Example 12

RPE-Specific mRNA Expression Measured by Quantitative, Real-Time, Reverse Transcription PCR (QPCR)

In order to characterize developmental stages during the human embryonic stem cell (hES) differentiation process into retinal pigmented epithelium (RPE) assays were employed to identify the expression levels of genes key to each representative stage of development. qPCR was developed to provide a quantitative and relative measurement of the abundance of cell type-specific mRNA transcripts of interest in the RPE differentiation process. qPCR was used to determine genes that are expressed in human embryonic stem cells, in neuroretinal cells during eye development, and in RPE cells differentiated from human embryonic stem cells. The genes for each cell type are listed below in Table 7.

TABLE 7

Genes specific to hES, neuroretina/eye, and RPE cells

| ES Cell-Specific | Neuroectoderm /Neuroretina | RPE-Specific Genes |
|---|---|---|
| Oct-4 (POU5F1) | Chx 10 | PAX-6 |
| NANOG | NCAM | PAX2 |
| Rex-1 | Nestin | RPE-65 |
| TDGF-1 | β-Tubulin | PEDF |
| SOX-2 | | CRALBP |
| DPPA-2 | | Bestrophin |
| | | MitF |
| | | Otx-2 |
| | | Tyr |

It was determined that hES-specific genes included Oct-4 (POU5F1), NANOG, Rex-1, TDGF-1, SOX-2, and DPPA-2. Genes specific to neural ectoderm/neural retina include CHXIO, NCAM, Nestin, and β-Tubulin. By contrast, RPE cells differentiated from human embryonic stem cells were found to express PAX-6, PAX2, RPE-65, PEDF, CRALBP, Bestrophin, MitF, Otx-2, and Tyr by qPCR measurement.

As evident from the qPCR tests, hES-specific genes are grossly downregulated (near 1000-fold) in RPE cells derived from hES, whereas genes specific for RPE and neuroectoderm are vastly upregulated (about 100-fold) in RPE cells derived from hES. In addition, qPCR analysis of fully mature RPE demonstrated a high level expression of the RPE-specific markers RPE65, Tyrosinase, PEDF, Bestrophin, MitF, and PAX6. This agrees with current literature regarding the Pax2-induced regulation of MitF and downstream activation of genes associated with terminally differentiated RPE.

The results of the assay demonstrates that RPE cells made by the methods described herein express multiple genes at the mRNA level that are not expressed by hES cells or neural ectoderm/neural retina cells. Thus the distinctive molecular fingerprint of mRNA in the ES-cell derived RPE cells of the invention constitutes a set of markers, such as RPE-65, tyrosinase, Bestrophin, PEDF, Mit-F, and PAX6, that make these RPE cells distinct from cells in the art, such as hES cells and neural ectoderm/neural retina cells. This assay also confirms that the human RPE cell preparations made in accordance with the methods described herein are substantially free from hES cell contamination.

Example 13

RPE-Specific Protein Expression Identified by Western Blot Analysis

To identify proteins expressed in the human RPE cells, a subset of hES-specific and RPE-specific markers were assayed by Western Blot. Actin was used as protein loading control.

The Western blot analysis confirms that the human RPE cells derived from hES cells did not express the hES-specific proteins Oct-4, NANOG, and Rex-1, whereas they expressed RPE65, CRALBP, PEDF, Bestrophin, PAX6, and Otx2. These proteins are therefore prominent markers of RPE cells differentiated from hES cells. By contrast, APRE-19 cells showed an inconclusive pattern of proteomic marker expression. See WO 2009/051671, FIG. 6.

The results of the assay demonstrates that RPE cells made by the methods described herein express multiple genes at the protein level that are not expressed by hES cells or APRE-19 cells. Thus the distinctive molecular fingerprint of protein expression in the ES-cell derived RPE cells of the invention constitutes a set of markers, such as RPE65, CRALBP, PEDF, Bestrophin, PAX6, and Otx2, that make these RPE cells distinct from cells in the art, such as hES cells and APRE-19 cells. This assay also confirms that the human RPE cell preparations made in accordance with the methods described herein are substantially free from hES cell contamination.

Example 14

Cryopreserved Preparations of Human RPE Cells

It is preferable that human RPE cells require reach a level of medium pigmentation prior to cryopreservation. PCR may used to determine if the cells are ready for cryopreservation (e.g., appropriate levels of RPE specific markers). Seven lots of human RPE cells (090621, 090606, 1211606, AB3, A090609, A090714, and A020101R04) manufactured assayed for the selected hES and RPE markers.

Figure 8:
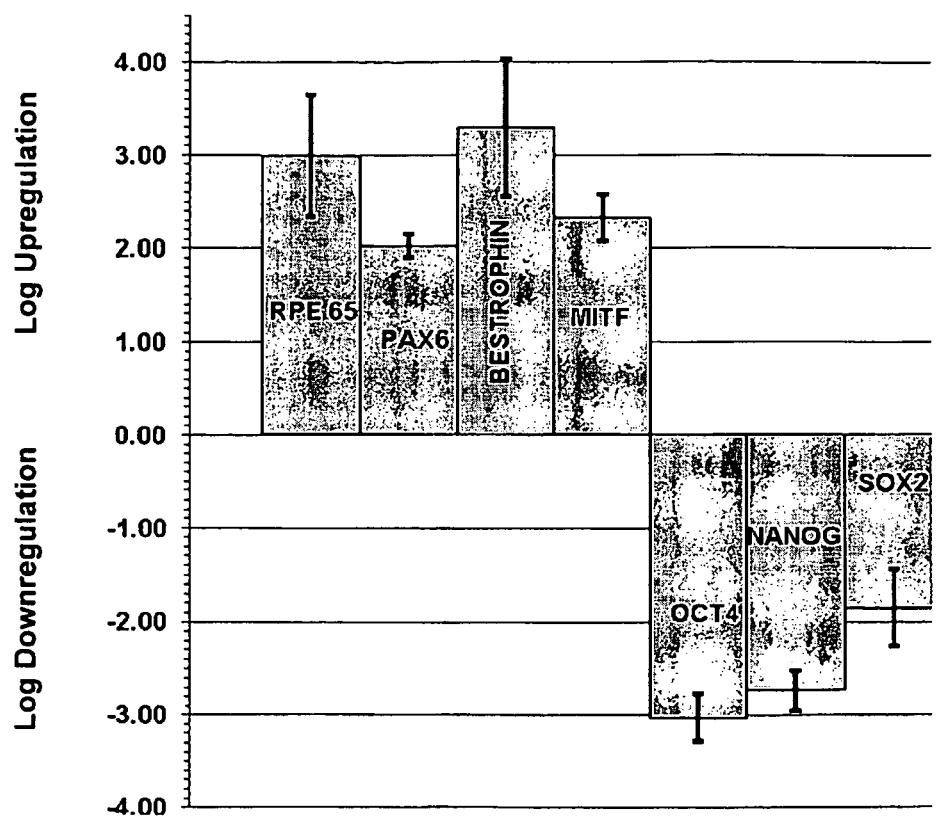
FIG. 8 depicts the Log up- or downregulation of ES and RPE markers, respectively, in RPE cells. The mean±SD relative gene expression of seven representative lots of RPE are shown. Data have been normalized to β-actin control levels for each sample and are expressed relative to the levels of expression observed in MA09 hES cells. The four upregulated RPE markers (e.g., RPE-65, PAX6, Bestrophin, and MIT) are shown on the left; the three downregulated hES markers (e.g., OCT4, NANOG and SOX2) are shown on the right.

For each lot, qRT-PCR assays for the seven markers were conducted in triplicate on at least 2 and up to 5 separate days. Data were normalized to the β-actin expression observed in each sample during each run and compared to the level of expression in the MA09 hES reference, also determined in each experimental run (MA09 hES cells were used as the pluripotent stem cells in the methods to make these seven lots of human RPE cells). For each of the seven lots, the mean expression for each marker was then calculated. To give each lot equal weight, the mean of the means for the seven RPE lots was then determined. Individual RPE lot means and the collective means for the four RPE markers and the three hES markers are shown in Table 8. Also shown are the highest and the lowest individual observed value for each of the markers. The data presented in Table 8 were plotted in the bar graph depicted in FIG. 8.

PAX6, and Otx2, that make these RPE cells distinct from hES cells. Accordingly, the human RPE cells described herein show upregulation of the RPE cell markers, RPE65, PAX6, bestrophin, and MITE, and downregulation of the ES cell markers, OCT4, NANOG, and SOX2, confirming that the human RPE cells are fully differentiated and have lost their pluripotency. This assay also confirms that the human RPE cell preparations are substantially free from hES cell contamination. Further, these RPE cells are at a desirable level of pigmentation so that they may be cryopreserved and thawed with high levels of viability after thawing.

Example 15

Pharmaceutical Preparations of Human RPE Cells

Manufacture of Pharmaceutical Preparations of human RPE
Pharmaceutical preparations of human RPE cells may be manufactured aseptically in a Class 100 biological safety cabinet. The diluent utilized for the pharmaceutical preparations may be ALCON BSS Plus® Intraocular Irrigating Solution, a sterile balanced salt solution, comprising sodium chloride (NaCl) 7.14 mg, potassium chloride (KCl) 0.38 mg, calcium chloride dihydrate ($CaCl_2*H_2O$) 0.154 mg, magnesium chloride hexahydrate ($MgCl_2*6H_2O$) 0.2 mg, dibasic sodium phosphate ($HNa_2PO_4$) 0.42 mg, sodium bicarbonate ($NaHCO_3$) 2.1 mg, dextrose 0.92 mg, glutathione disulfide 0.184 mg, and sodium hydroxide and/or hydrochloric acid to adjust pH and water for injection per milliliter (mL). The pH is about 7.5 and the osmolality about 305 mOsm/Kg.

Prior to injection, the RPE cells may be thawed for use. The vial of cells may be removed from the liquid nitrogen freezer, placed in a water bath at 37° C., and constantly agitated until the entire contents are liquid. For each cryovial, the thawed contents may be resuspended in 1 mL of

TABLE 8

RPE Gene Expression Relative to MA09 hES

| RPE Lot | Mean Log 10 Upregulation RPE Cells Markers | | | | Mean Log 10 Downregulation hES Cell Markers | | |
|---|---|---|---|---|---|---|---|
| | RPE65 | PAX6 | BESTROPHIN | MITF | OCT4 | NANOG | SOX2 |
| 090621 | 3.55 | 1.99 | 3.66 | 2.48 | −3.05 | −2.87 | −1.74 |
| | (n = 4) | (n = 5) | (n = 5) | (n = 5) | (n = 5) | (n = 3) | (n = 5) |
| 090606 | 2.06 | 1.89 | 2.03 | 2.20 | −2.87 | −2.92 | −1.54 |
| | (n = 2) | (n = 2) | (n = 2) | (n = 2) | (n = 2) | (n = 2) | (n = 2) |
| 1211606 | 2.63 | 2.24 | 2.53 | 2.22 | −2.68 | −2.63 | −1.19 |
| | (n = 2) | (n = 2) | (n = 2) | (n = 2) | (n = 2) | (n = 2) | (n = 2) |
| AB3 | 3.43 | 2.14 | 3.94 | 2.24 | −2.83 | −2.87 | −2.20 |
| | (n = 3) | (n = 4) | (n = 4) | (n = 5) | (n = 4) | (n = 3) | (n = 4) |
| A090609 | 3.18 | 1.95 | 3.47 | 2.42 | −3.17 | −2.44 | −2.26 |
| | (n = 4) | (n = 4) | (n = 5) | (n = 5) | (n = 5) | (n = 4) | (n = 4) |
| A090714 | 3.76 | 2.06 | 4.05 | 2.78 | −3.13 | −2.44 | −1.80 |
| | (n = 4) | (n = 4) | (n = 5) | (n = 5) | (n = 5) | (n = 4) | (n = 5) |
| A020101R04 | 2.33 | 1.95 | 3.35 | 2.00 | −3.45 | −2.93 | −2.28 |
| | (n = 3) | (n = 3) | (n = 4) | (n = 5) | (n = 4) | (n = 3) | (n = 4) |
| MEAN of MEANS | 2.99 | 2.03 | 3.29 | 2.33 | −3.03 | −2.73 | −1.86 |
| | (n = 7) | (n = 7) | (n = 7) | (n = 7) | (n = 7) | (n = 7) | (n = 7) |
| SD | 0.65 | 0.12 | 0.74 | 0.25 | 0.26 | 0.22 | 0.41 |
| Low | 1.80 | 1.30 | 1.59 | 1.80 | −2.56 | −2.10 | −1.14 |
| High | 4.50 | 3.00 | 4.50 | 3.50 | −3.70 | −3.30 | −2.60 |

The results of the assay demonstrates that human RPE cells made by the methods described herein express multiple genes that are not expressed by hES cells. Thus the distinctive molecular fingerprint of protein expression in the ES-cell derived RPE cells of the invention constitutes a set of markers, such as RPE65, CRALBP, PEDF, Bestrophin, PAX6, RPE-MM and transferred to a separate sterile 50 mL tube. RPE-MM are added to each conical tube to bring the volume to 40 mL. The tube may then centrifuged, the supernatant aspirated and the pellet resuspended in 40 mL of BSS-Plus. The cell suspension may be again centrifuged, the supernatant aspirated. The pellet may be resuspended in a second volume of 40 mL of BSS-Plus and the cells pelleted by centrifugation a third time.

The resulting pellet may be resuspended in about 75 µL of BSS-Plus per vial thawed and the cells transferred to a sterile 0.5 mL sterile microcentrifuge tube. A viable cell count may be performed and the appropriate volume of BSS-Plus is added to achieve the appropriate density of cells for dosing. The pharmaceutical preparations of human RPE cells may have a preparation viability of at least about 85%. These cells may maintain this viability for at least about 4 hours post preparation. A 200 µL sample of the formulated product may be placed in a sterile microcentrifuge tube. The vial may be placed on ice for transport to the surgical facility and is stable for at least about 4 hours after preparation (e.g., cells may be used in therapy within at least about 4 hours of preparation). See FIG. 7.

DMSO Levels in Pharmaceutical Preparation

Three exemplary lots of RPE cells: 090621, MA09p334+2, and MA01p50+4. Each lot was thawed and a final dose preparation was prepared as described herein to achieve a cell density of 1333 viable cells/µL (e.g., equivalent to about a $2 \times 10^5$ cell dose). A 200 µL sample of the cell suspension was transferred to cryovials, frozen at −20° C. and shipped to a testing lab for determination of DMSO residual levels using gas chromatography.

The results indicate that preparation of the pharmaceutical preparation of RPE lots 090621, MA09p334+2, and MA01p50+4 resulted in extremely low DMSO residual levels (ppm) (e.g., below levels considered acceptable for clinical administration). Therefore the preparation of the RPE cells described results in DMSO residual levels acceptable for clinical administration.

Endotoxin Levels in Pharmaceutical Preparation

Three exemplary lots of RPE cells: 090621, MA09p334+2, and MA01p50+4. Each lot was thawed and a final dose preparation was prepared as previously described to achieve a cell density of 1333 viable cells/µL (e.g., equivalent to about a $2 \times 10^5$ cell dose). A 100 µL sample of the cell suspension was transferred to cryovials, stored at 4° C. and shipped to a testing lab for endotoxin levels using a kinetic turbidimetric assay with a sensitivity of 0.001 EU/mL.

The results indicate that preparation of the clinical formulation using RPE lots 090621, MA09p34+2, and MA01p50+4 resulted in endotoxin levels of <0.100, 0.993 and <0.100 EU/mL, respectively. Therefore the preparation of the RPE cells according to the methods described herein results in endotoxin levels acceptable for clinical administration. Thus the human RPE cells prepared according to the methods described herein may be prepared, stored, thawed, and formulated in a pharmaceutical preparation suitable for therapeutic applications.

Example 16

Capillary and Cannula Cell Delivery Systems

Needle/syringe and cannula systems were tested for damage/loss of human RPE cells (e.g., cell viability/activity, cell adhesion to the syringe) at a cell dose of about $1 \times 10^5$ human RPE cells in a small volume (e.g., about 2-3 µL).

Capillary Cell Delivery System

Cryopreserved vials of RPE lot 090621 were thawed and formulated in a pharmaceutical preparation. The resulting RPE were formulated in BSS-Plus and resuspended at 50,000 viable cells per microliter (µL).

The capillary delivery system used was a 25 µL Hamilton syringe and a standard glass capillaries made by World Precision Instruments (WPI), Standard Glass Capillaries: 4 in. (100 mm); 1.5/0.84 OD/ID (mm) filament, fire polished using natural gas.

The Hamilton syringe and glass capillaries were autoclaved prior to use. The tubing was flushed with 70% sterile ethanol using a syringe and needle. This was followed by thorough flushing with sterile PBS prior to use. A 20 gauge syringe needle was affixed to the syringe. One end of the tubing was fitted to the needle and the other end of the tubing was inserted over the capillary tube.

BSS-Plus was drawn into the capillary, tubing, and syringe. BSS-Plus was then expelled until about 2-3 inches of the tubing was void to ensure that there was an air bubble between the cells and medium. About 10-12 µL of the cell suspension was drawn into the capillary. About 2 µLs of the cell suspension was dispensed over about a 10-20 second time interval into a sterile microcentrifuge tube. The dispensing was repeated 8 times until about 16 µl had been delivered over about a 1.5-2 minute period.

The RPE cells were then assessed for assessed for viable cell number and their ability to grow in culture. Samples of RPE cells that had been delivered through the capillary were tested for viable cell number by trypan blue exclusion and compared to the same formulated RRE cells that had not been delivered. Control and capillary subjected cells were also seeded in 4-well plates at 50,000 viable cells per well in 1 mL of RPE growth medium. After four days in culture, control and capillary delivered RPE cells were trypsinized and cell counts were performed.

Vials of cryopreserved RPE cells (lot 090621) were thawed, washed and resuspended in BSS-Plus at a concentration of 50,000 viable cells per microliter. The viability of the formulated RPE was 88%. The viable cell counts performed on RPE preparation that had been delivered through the capillary system versus control cells are shown in the Table 9.

TABLE 9

| Viable Cell Counts | | |
|---|---|---|
| | Control RPE Cells | Capillary Injected RPE Cells |
| Viable Cell/µL | 50,500 | 47,875 |
| Percent Viability | 92 | 93 |
| Viable Cells/Well (seeded at about 50,000 cells) | 283,125 | 279,375 |

To assess longer-term survival, aliquots of RPE capillary delivered and control RPE cells were seeded at 50,000 viable cells per well and cultured for four day before harvesting and counting. These results are also shown in Table 8.

Capillary-injected and non-injected RPE showed no difference regarding the viability, viable cell number or the ability to propagate in culture. The capillary-injection system used in the preclinical studies had no adverse effects RPE number, viability or their capacity to proliferate in culture.

Cannula Cell Delivery System

A study was done to confirm that the use of the cell delivery system, a 30-gauge Angled Rigid Injection Cannula, (Synergetics Inc.), does not have an impact on the viability or survivability of the RPE cells. This study was performed with nominal cell concentrations of 800 cells/µL and 1,000 cells/µL.

Cryopreserved RPE cells (Lot 090621) were thawed, washed with MDBK-MM media, and resuspended with BSS-Plus. Resuspended RPE cells were centrifuged and resuspended again with 400 µL of BSS-Plus in a fresh microcentrifuge tube. A viable cell count was done on the cell suspension, and the concentration was adjusted to ±5% of the target concentration. The rigid injection cannula was attached to a 1 mL TB syringe aseptically, and 200 µL of the cell suspension were drawn up into the syringe via the cannula. The remaining 200 µL in the tube was labeled "Non-Cannula". The cell suspension in the syringe was dispensed into a new microcentrifuge tube at a rate of 10-15 µL over 10 seconds.

A viable cell count was cell count was done to the "Cannula-Injected" sample. From both the "Non-Cannula" and "Cannula" samples 10,000 cells/well were seeded into 96 well-plates the cells were cultured in RPE-GM. Another cell count was done 3-4 days post seeding to assess the long term survival status. The cell counts for the cannula-injected sample and non-cannula injected sample are provided in Table 10.

TABLE 10

RPE Survival for Non-Cannula and Cannula Suspension

|  | Non Cannula | Cannula |
|---|---|---|
| 800 cell/µL Nominal |  |  |
| Day 0 (viable cells/µL) | 825 | 782 (94.8%)* |
| Day 3 (total cells/well) | 218875 | 201887 (92.3%)* |
| 1000 cells/µL Nominal |  |  |
| Day 0 (viable cells/µL) | 960 | 1000 (104.2%)* |
| Day 4 (total cells/well) | 297050 | 282750 (95.2%)* |

*% non-cannula value

The number of viable cell/µL after the cannula passage was comparable to the non-injected RPE cells as shown in the Table 9. Also, the number of viable cells 3-4 days post seeding did not differ significantly. The data presented herein demonstrates that the needle/syringe and cannula systems that may be used for administration of human RPE cells can deliver a cell dose up to $1 \times 10^5$ human RPE cells in a small volume (e.g., about 2-3 µL) without damage/loss of cells (e.g., cell viability/activity, cell adhesion to the syringe). In conclusion, cannula/syringe passage does not substantially affect the viability or survivability of RPE cells. This is consistent with the preclinical data which shows that following subretinal injection in rats and mice, RPE cells are seen both microscopically and using immunostaining using human specific antigens.

Example 17

RPE Cells are not Tumorigenic

The methods of producing RPE cells described herein remove ES cells from the RPE cell preparation, thereby reducing the risk of teratoma formation. This was confirmed by assays to detect the presence of hES in the RPE cells described herein. The human RPE cells described herein were tested for tumor formation and no such tumors were detected.

NIH-III nude mice considered suitable for study were weighed prior to cell implantation. A total of 27 animals were treated with hES cells, 30 animals were treated with RPE cells, and 10 animals were left untreated. After all implantation procedures were completed, 56 male mice (weighing 19.6 to 26.0 g at randomization) were assigned to the respective control and treatment groups identified in the following table using a simple randomization procedure for each group.

TABLE 11

SUMMARY OF ADMINISTRATION

| Group Number | Treatment | Number of Male Animals | Cell Number (per injection[a]) | Injection Volume (µL) | Termination (Week) |
|---|---|---|---|---|---|
| 1 | hES cells | 23 | $1 \times 10^5$ | 3 | 4, 12, 40[b] |
| 2 | RPE cells | 24 | $1 \times 10^5$ | 3 | 4, 12, 40[b] |
| 3 | None (Control) | 9 | NA | NA | 40 |

[a]Cells were implanted into the subretinal space of the right eye.
[b]Six animals per group were euthanized 4 weeks after cell implantation, 7 animals were euthanized 12 weeks after cell implantation, and the remaining animals were euthanized 40 weeks after cell implantation.
hES—Human Embryonic Stem
RPE—Retinal Pigment Epithelial
NA—Not available/applicable At necropsy, the animals were euthanized and necropsied sequentially but alternating groups. The animals were evaluated at 4, 12 and 40 weeks (which is the approximate lifespan of the animal models). As only one eye from each animal was treated, each animal acted as its own control.

The hES cell group observed significant tumor formation in 100% of the animals, some as early as 4 weeks. In contrast, the RPE treated animals did not form tumors out to the lifespan of the animals. Thus the human RPE cells preparations do not pose a risk of tumor formation following transplantation. Accordingly, the human RPE cell preparations are acceptable for use in transplantation (e.g., therapeutic applications).

Example 18

The RPE Cells are Stable and Integrated in Animal Models after Transplantation

A fundamental limitation on the success and usefulness of cell-based therapies (e.g., transplantation) is the inability of the transplanted cells to survive, maintain their phenotype, integrate, and function following transplantation. To assess the stability and integration of RPE cells, following injection into the eyes of 22 mice, the presence and phenotypic stability of the transplanted human RPE cells was confirmed by immunofluorescense (to detect human molecular markers) and PCR (to detect human DNA). At 1 week, 1 month, 3 month, and 9 month time points the hRPEs were be identified apart from other cells by means of their physical characteristics (e.g., by their mRNA and protein expression and presence of human DNA in a mouse model.)

Co-Immunofluorescence

In mouse eyes injected with human RPE cells, the human RPE cells were identified by positive co-immunofluorescence to human mitochondrial antigen and bestrophin antigen and located within the mouse retinal pigmented epithelial cell layer, subjacent to the retina, within the posterior chamber or within the remaining scar at 9 months post-injection. Under light microscopy, the morphology of the positive staining cells was characterized as typically linear arrangements of cuboidal cells with round nuclei that were displaced eccentrically by small golden-brown intracytoplasmic pigment, and were consistent with retinal pigmented epithelial cells.

Cells staining positive for both human mitochondria and bestrophin were identified as linear to small round aggregates within the RPE layer, in subretinal locations, within scar, or as small aggregates within the posterior chamber vitreous space. Specifically, immunofluorescent cells consistent with RPE were identified within the mouse RPE layer and subretinal space in 8 of 12 mice eyes examined in this study. In 2 of 4 mice eyes, RPE cells were also identified within the posterior chamber and in 1 of 4 mice, RPE cells were identified in scar. RPE cells were not observed in 3 of 12 eyes prepared for staining.

Under bright field light microscopy, in all cases the morphology of the positive-staining human cells was characterized as organized linear arrangements of 4 to 10 cuboidal cells with round nuclei that were displaced eccentrically by small golden-brown intracytoplasmic pigment, consistent with retinal pigmented epithelial cells. When associated with the mouse RPE, the human cells displayed typical polarity along a basement membrane with basally located nuclei and apically located pigmented granules. The human cells could be distinguished from mouse RPE as the human cells appeared slightly larger with fewer and smaller yellow-brown pigmented granules compared to the mouse RPE. There was no evidence of abnormal growth in the sections examined under the conditions of bright field microscopy.

None of the isotype or negative antibody controls showed any specific staining. The untreated eye was consistently negative for any fluorescence.

Detection of Human DNA

Although there is wide inter-animal variation within all the cohorts, human DNA was detected in all transplanted mice tested, including the 22 mice assayed at the final (nine month post-transplantation) time-point. DNA was generally higher in mice that received the 100,000 cell dose compared to mice that received 50,000 RPE cells. There is a relatively consistent level of DNA present throughout the observation period out to nine months with no consistent increase or decrease in DNA content. Additionally, histopathological assessments confirm that RPE cells survived in animal eyes out to nine months.

TABLE 12

Human DNA Detected in Mouse Eyes Transplanted with RPE Cells†

| Treatment | 1 week | | 1 month | | 3 months | | 9 months | |
|---|---|---|---|---|---|---|---|---|
| | Animal ID | DNA (pg) | Animal ID | DNA (pg) | Animal ID | DNA (pg) | Animal ID | DNA (pg) |
| 50,000 RPE cells | 614 | 5056 | 970 | 3040 | 916 | 151 | 712 | 3762 |
| | 672 | 815 | 958 | 621 | 930 | 959 | 716 | 772 |
| | 683 | 2743 | 960 | 2116 | 908 | 3064 | 727 | 70 |
| | 615 | 1647 | 952 | 4763 | 945 | 334 | 742 | 303 |
| | 668 | 738 | 957 | 3160 | — | — | 917 | 1984 |
| | mean | 2200 | mean | 2740 | mean | 1127 | mean | 1378 |
| | SD | 1790 | SD | 1359 | SD | 1337 | SD | 1523 |
| 100,000 RPE cells | 611 | 1754 | 984 | 2135 | 920 | 3100 | 711 | 16025 |
| | 609 | 3827 | 956 | 6161 | 918 | 880 | 717 | 4139 |
| | 680 | 11104 | 977 | 3005 | 925 | 1184 | 736 | 11278 |
| | 608 | 15377 | 978 | 1250 | 910 | 5195 | 747 | 3290 |
| | 622 | 12419 | 972 | 3809 | 929 | 6248 | 921 | 805 |
| | mean | 8896 | mean | 3272 | mean | 3321 | mean | 7107 |
| | SD | 5831 | SD | 1877 | SD | 2280 | SD | 6325 |

†The inter-animal variation within all the cohorts (e.g., apparent different levels of DNA observed among the three groups) is not considered significant and is attributed to variability in the surgical procedure which may impact cell survival.

The eyes receiving the transplanted human RPE cells displayed healthy swathes of bestrophin positive cells with typical RPE morphology. No tumors were detected in this group or any other cohort except mice injected with the 100% hES dose.

These data show that the NIH-III mouse model supports the survival of the injected human RPE cells for a significant time interval. A major obstacle to developing a stem cell-based therapy for degenerative retinal disorders is the poor integration and differentiation of retinal stem cells transplanted into recipient retinas. The RPE cells described herein, in contrast, are well tolerated, stable, and integrate into the patent after administration without tumor formation.

Example 19

Human RPE Cells Survive Long-Term Post-Injection in Ocular Tissues

A limitation on the success and usefulness of cell-based therapies (e.g., transplantation) is the inability of the transplanted cells to survive long-term following transplantation and the risk of teratoma formation. The purpose of this example was to identify, localize and characterize the morphology of RPE cells after 1, 3 and 9 months post-injection. The transplanted human RPE cells survived in representative animals up to over 200 days, with no evidence of tumor formation or non-retinal human cells in the eyes. Cell proliferation was evaluated at the 9 month time point for animals evaluated in the utilizing Ki67 staining. No proliferation was seen in either of these studies.

Selected ocular tissue sections were stained for the presence of human mitochondria, human bestrophin, and human Ki67. Anti-human mitochondrial staining was used as a clear marker for confirming human cell origin. Bestrophin is a basolateral plasma membrane protein expressed in retinal pigment epithelial cells, and was used to confirm RPE origin. Ki67 is a well recognized cell proliferation marker. See, e.g., Magdelénat (1992) J. Immunol. Methods 150(1-2):133-43.

Immunofluorescence staining was chosen over immunoperoxidase staining for demonstration of the antigens due to the presence of pigment in the cells of interest and to facilitate double staining of sections for bestrophin and Ki67. Ki67 staining in this study was only conducted at the 1 and 3 month timepoints.

Positive and negative control tissues showed specific, sensitive and reproducible staining with minimal nonspecific background staining. Cells stained for human mitochondria as bright red punctate cytoplasmic staining viewed with Cy3 580 nm filter. Cells stained for bestrophin as bright green basolateral membrane staining viewed with Zlexa 488/Dylight488-550 nm filter. Ki67 staining was specific for nuclei and was bright green under the same filter. Antibodies appeared to be human-specific as there was no cross-reactivity with mouse tissue. However, some background staining was encountered in some sections, usually associated with retinal photoreceptors, vessel walls, collagen or skeletal muscle, but it was easily distinguished based on level of brightness, staining pattern and location.

None of the isotype or negative antibody controls showed any specific staining. The untreated eye was consistently negative for any fluorescence.

At all time points, cells staining positive for both human mitochondria and bestrophin were identified as linear to small round aggregates within the RPE layer, in subretinal locations, occasionally within scars, or as small aggregates within the posterior chamber vitreous space. In all cases, the morphology of these human cells was characterized as organized cuboidal epithelial cells with round nuclei displaced by small golden-brown intracytoplasmic pigment, consistent with pigmented epithelial cells. When associated with the mouse RPE, the human cells displayed typical polarity along a basement membrane with basally located nuclei and apically located pigmented granules. The human cells could be distinguished from mouse RPE as the human cells appeared slightly larger with fewer and smaller yellow-brown pigmented granules compared to the mouse RPE.

At the 1 month time point, the RPE cells were readily identified as linearly organized cells within the RPE and/or subretinally in 5 of 6 mice dosed with 100,000 cells and nuclear Ki67-positive staining was observed in 4 out of 5 mice eyes in which RPE cells were identified. In mice dosed with 50,000 cells, RPE cells were observed in 3 of 6 mice eyes, and Ki67-positive cells were also observed in these same 3 mice eyes.

At the 3 month time point, most of the slides had moderate sectioning artifact but small aggregates of RPE cells were identified within the RPE and/or subretinal space in 2 out of 6 mice dosed with 100,000 cells and 3 out of 6 mice dosed with 50,000 cells. Ki67 staining was performed for 2 mice dosed with 100,000 cells and 4 mice dosed with 50,000 cells: Ki67 positive staining was observed in human RPE cells in 4 of 6 mice. No staining for Ki67 was observed in 2 mice in which staining for RPE was adequate (both in the 50,000 cell dose group). In 2 mice dosed with 100,000 cells, only few RPE cells were identified and considered inadequate to assess Ki67 status.

At the 9 month time point, immunopositive RPE cells were identified within the mouse RPE and/or subretinal space in 5 of 6 mice eyes dosed at 100,000 cells and 2 of 5 mice eyes dosed with 50,000 cells. In 1 of 11 mice (animal number 743 dosed with 100,000 cells) immunopositive RPE cells were identified in the posterior chamber and scar; and in 1 animal (animal number 744 dosed with 50,000 cell) RPE cells were only observed in the scar. RPE cells were not identified in 2 of 5 eyes prepared for staining in 50,000 cell group at the 9 month time-point. Ki67 staining was not performed for this group of slides.

Conclusion

In mouse eyes injected with human retinal pigmented epithelial cells, RPE cells were identified by positive co-immunofluorescence to human mitochondrial antigen and bestrophin antigen and located within the mouse retinal pigmented epithelial cell layer, subjacent to the retina, within the posterior chamber or within the remaining scar up to 9 months post-injection. Under bright field light microscopy, the morphology of the positive staining cells was characterized as typically linear arrangements of cuboidal cells with round nuclei that were displaced eccentrically by small golden-brown intracytoplasmic pigment, and were consistent with retinal pigmented epithelial cells. A subset of these cells showed nuclear positivity for the proliferation marker Ki67 at 1 and 3 months after injection.

Function was deteriorating down towards baseline levels by 180 days of age (i.e., 160 days post-transplantation). At the point where function was diminished, there were no signs of pathological manifestations.

The appearance of the remaining retina was also examined. There were no untoward manifestations. Photoreceptor survival was evident in most of the transplanted animals although donor cell survival as seen by human nuclear marker staining was less frequent. There was no indication of extraneous cell growth or of abnormal cell patterns within the inner retina.

Normal retinal appearance was observed in RCS rats (i.e., no vascular abnormalities, laminar disorder) in the area where the transplanted cells were introduced, in spite of the fact that donor cells were no longer evident in some of these eyes. Photoreceptors, although present, were fewer in number than would typically be seen at 100 days of age after P21 transplants. There was no evidence in any of the eyes examined of potentially tumorous growth of the donor cells.

Human pigmented epithelial cells were identified within segments of rat retinal pigmented epithelial cells, and thus confirm the presence of human cells in representative animals up to >220 days post surgery. The cells were consistent with RPE morphology and positive for bestrophin. Therefore, the human RPE cells described herein may be transplanted where they integrate forming stable, functional retinal pigmented epithelial layer.

TABLE 13

Long-Term Survival of hRPE cells in mouse eyes

| Survival Time | Number of Animals | Animals with human cells found in the eye (number) | Animals with human cells surviving in the eye (%) |
| --- | --- | --- | --- |
| 1 month (4 weeks) | 26 | 26 | 100% |
| 2 months (8 weeks) | 19 | 19 | 100% |
| 3 months (12 weeks) | 28 | 28 | 100% |
| 9 months (40 weeks) | 52 | 48 | 92% |

Unlike other transplant locations, the eye is a small organ and the number of cells that may be implanted into the subretinal space is quite small (e.g., 100,000 RPE cells) compared to millions of cells that may be injected into other sites for other conditions. Additionally, the survival rate of transplanted cells (e.g., xenogenic, allogeneic, syngeneic, or autologous) in various animal models is generally low. Although donor cells may be easily detected immediately after transplantation (e.g., several days out to 3 weeks), there is a progressive loss of survival over time, generally resulting in less than 1% long-term survival in animal model studies. For example, Wang, et at (2005) *Invest Opthalmol Vis Sci* 46(7): 2552-60 reported a loss of surviving human RPE cells in immunosuppressed RCS rat eyes from 5% at 6 weeks post transplantation to 0.2% at 28 weeks. Carr, et al. (2009) *PLoS One* 4(12): 8152 disclosed that human iPS-RPE cells were undetectable 13 weeks post-transplantation. Del Priore, et al. (2003) *Invest Opthalmol Vis Sci* 44(9): 4044-53 found <1% of porcine RPE cells in rabbit eye model after 12 weeks and Canola, et al. (2007) *Invest Opthalmol Vis Sci* 48(1): 446-54 showed only 0.44% of injected cells survived at 3 months. In the methods described herein, only a portion of the transplanted RPE cells (e.g., >1%) may survive long-term (e.g., over 9 months). The inventors surprisingly discovered, however, that only a small number of cells are required to affect visual improvement.

Example 20

Evaluation of Various Delivery Procedures

The purpose of the example was to examine the subretinal injection of RPE cells in non-human primates, in particular vitrectomy, a method to create a subretinal bleb, and cell doses. The risk of stem cell graft rejection and the presence of any deleterious effects on the retinal physiology as a consequence of cell injection was also examined. The study used 8 animals (16 eyes). All animals were injected according to the following schedule in Table 14.

TABLE 14

Animal Injection Schedule

| Animal # | Age (Yrs) | Right Eye Number of Blebs (50,000 cells) and position relative to macula/optic disc | Left Eye Number of blebs (50,000 cells) and position relative to macula/optic disc | Cyclosporine |
|---|---|---|---|---|
| A | 2 | 1 submacular | 2 superior | None |
| B | 2 | 1 submacular | 2 superior, inferior. 1 nasal | None |
| C | 17 | 1 superotemporal | 1 superotemporal | None |
| D | 16 | 1 superior, 1 temporal, 1 nasal to optic disc | 1 superior, 1 temporal | None |
| E | 13 | 2 superior | 2 superior | 5 mg/kg IM SID |
| F | 16 | 1 superotemporal. 2 nasal to optic disc | 1 inferior, 1 inferonasal to optic disc | 5 mg/kg IM SID |
| G | 16 | 2 superior, 1 inferior | 2 superior, 1 inferonasal | 5 mg/kg IM SID |
| H | 15 | 2 inferior, 1 nasal to optic disc | 2 inferior, 1 nasal to disc | 5 mg/kg IM SID |

The surgeries were done on two days: on the first surgery day the following steps were followed: After the animal was intubated, the area around the eyes were prepped with iodine solution. A 1060 drape was used to drape the animal for ophthalmic surgery. For each of the animal, the right eye was done first then the left. A Barraquer-type speculum was inserted. A peritomy was created in the superotemporal quadrant. The scleral bed was cauterized with wet-field cautery to achieve hemostasis. A sclerotomy was created 3 mm posterior to the limbus with a 20 gauge MVR blade. A plug was placed and a similar procedure was done in the superonasal quadrant to create a peritomy and a sclerotomy.

For some subjects, vitrectomy was performed using an end-irrigating light pipe, a vitrector, and a hand-held irrigating contact lens in an effort to elevate the posterior hyaloid. Then a 19 gauge end-irrigating light pipe, a Synergetics subretinal injector, and a Machemer irrigating contact lens were used to create subretinal blebs. Then a subretinal pick was used to inject the cells. Then the sclerotomies were closed using 6-0 Vicryl sutures and the conjunctival peritomy with a 6-0 plain gut sutures. Zinacef (Cefuroxime, 125 mg) and Decadron (Dexamethasone, 10 mg) were given as subconjunctival injections OU. Erythromycin ointment was placed over the eyes OU.

On the second day of surgery, the following steps were followed for each procedure: After the animal was intubated, the area around the eyes was prepped with iodine solution. A 1060 drape was used to drape the animal for ophthalmic surgery. For each of the animal, the right eye was done first then the left. A Barraquer-type speculum was inserted. A peritomy was created in the superotemporal quadrant. The scleral bed was cauterized with wet-field cautery to achieve hemostasis. A sclerotomy was created 3 mm posterior to the limbus with a 20 gauge MVR blade. A plug was placed and a similar procedure was done in the superonasal quadrant to create a peritomy and a sclerotomy. Then a 19 gauge end-irrigating light pipe, a Synergetics subretinal injector, and a Machemer irrigating contact lens were used to create subretinal blebs. Then a subretinal pick was used to inject 50 micoliters of stem cells (2000 cells/microliter) into each of the blebs. Then the sclerotomies were closed using 6-0 Vicryl sutures and the conjunctival peritomy with a 6-0 plain gut sutures. Zinacef (Cefuroxime, 125 mg) and Decadron (Dexamethasone, 10 mg) were given as subconjunctival injections OU. Erythromycin ointment was placed over the eyes OU. Following each surgery retinal photos and ERGs were done. At termination all animals underwent full necropsy and the eyes were examined histologically.

To summarize, the technique was refined to be a two port pars plana approach with an irrigating light pipe and subretinal cannula, and we have histologically confirmed successful implantation to the subretinal space. A vitrectomy may also be performed, if desired.

One suitable method for subretinal bleb formation was as follows: the retina may be approached with the Synergetics subretinal cannula connected to a Hamilton 1 ml syringe with a screw plunger containing Balanced Salt solution (BBS). The BSS may be injected slowly creating a retinotomy and then a small subretinal bleb is raised. This may minimize retinal trauma. The cannula may be then introduced through the retinotomy and the BSS injection restarted and continued to expand the bleb to the correct volume. A process of gentle retinal massage releases the tension in the bleb. The Synergetics cannula may be removed and a 30-gauge Hurricane Instruments needle connected to tubing and syringe preloaded with cells may be introduced. The cells may be infused over about one minute under direct viewing to ensure correct cannula positioning and minimize reflux. This instrumentation procedure is suitable for use in humans.

Retinal photography and electrophysiology were performed on each eye preoperatively and at the 2-week and one-month time points. Complete retinal reattachment was noted within 24 hours and multifocal ERG recordings show no electrophysiological evidence of pathology. In total, fifteen eyes of eight adult rhesus macaques underwent histological examination; one eye developed endophthalmitis and was excluded from the study. BrdU labeling was used to detect the human RPE cells. Cells were observed localized to the subretinal space and are associated with retinal reattachment, excellent preservation of retinal morphology, and lack of inflammation or rejection.

Example 21

RPE Cells in Photoreceptor Rescue in the RCS Rat Model

At postnatal day 21-23 (P21 —23), RCS rats (n=14) were anesthetized and received subretinal injections of 20,000 hRPE cells/eye via a trans-scleral approach into the upper temporal retina area. Control rats received an injection of medium alone (n=8). Non-dystrophic congenic rats were available for comparison. All animals received daily dexamethasone injections (1.6 mg/kg, i.p.) for 2 weeks and were maintained on cyclosporin-A administered in the drinking water (210 mg/L; resulting blood concentration: 250-300 μg/L) days prior to cell injection until animals were euthanized.

Figure 9:
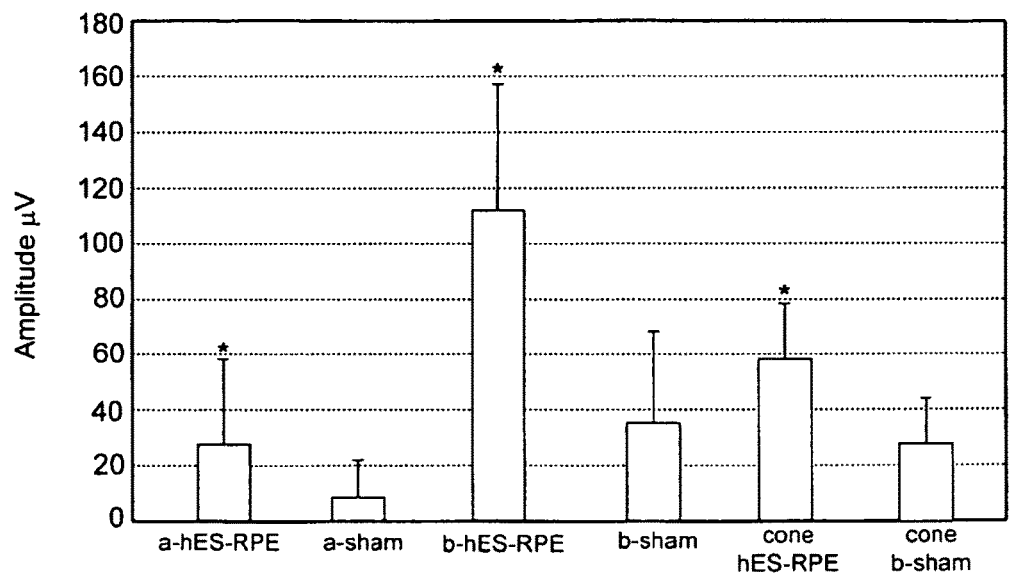
FIG. 9 depicts electrical activity of the outer (a-wave) and inner (b-wave) retina in response to light flashes test by ERG responses at both P60 and P90. ERG responses in RPE grafted animals achieved significantly better responses over sham controls (p<0.05, t-test).

To test visual function, the electrical activity of the outer (a-wave) and inner (b-wave) retina in response to light flashes was tested by ERG responses at both P60 and P90. At P60, the a-wave ERG response is normally lost in RCS rats, and by P90, the b-wave response is severely depleted, allowing graft-related effects to be recognized over background performance. By P60, hES-RPE grafted animals achieved significantly better responses over sham-injected animals ($p \leq 0.05$, t-test) for a-wave (31±27 vs. 6±17 V), b-wave (108±46 V vs. 36±33 V) and cone b-wave (57±19 vs. 28±13 V) (FIG. 9).

Figure 10:
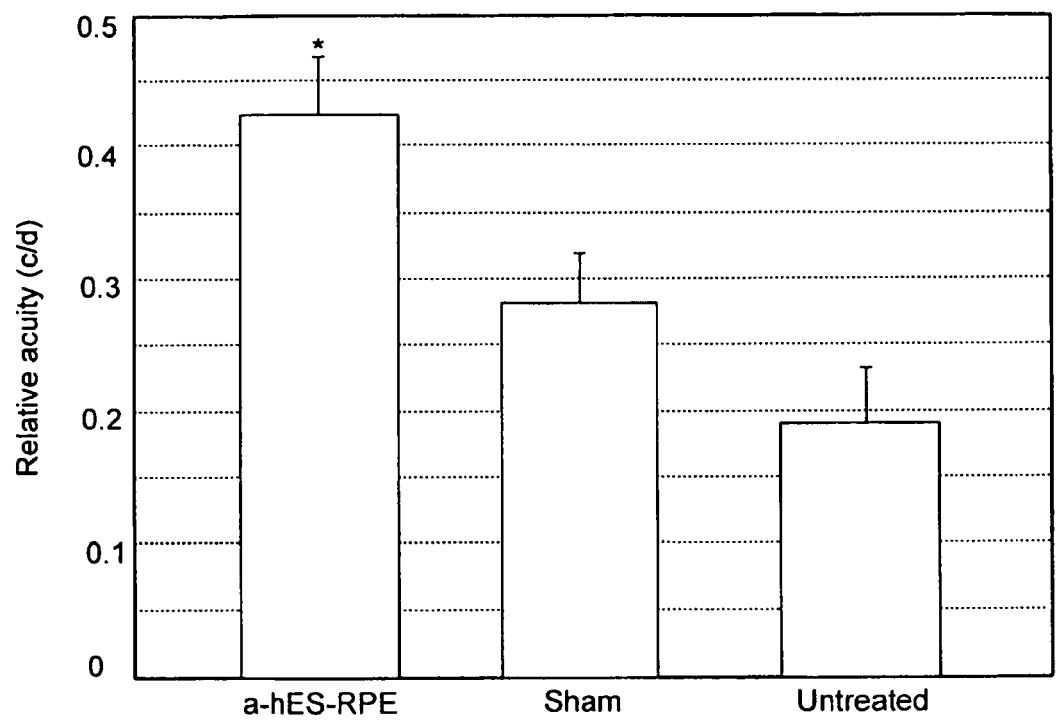
FIG. 10 depicts date from an optomoter data system shows that shows that the RPE treated eyes performed significantly better than the sham-treated and untreated eyes (p<0.05, t-test), giving approximately 50% and 100% improvement in visual acuity over the sham and untreated controls, respectively.

The optomotor test was used to provide a measure of spatial acuity. On P100 sham-injected rats, a threshold response of 0.29±0.03 c/d was recorded and untreated animals gave a figure of 0.21±0.03 c/d. By contrast, the cell-grafted rats sustained levels of 0.42±0.03 c/d, significantly better than sham injected rats ($p \leq 0.05$, t-test) (FIG. 10).

Figure 11:
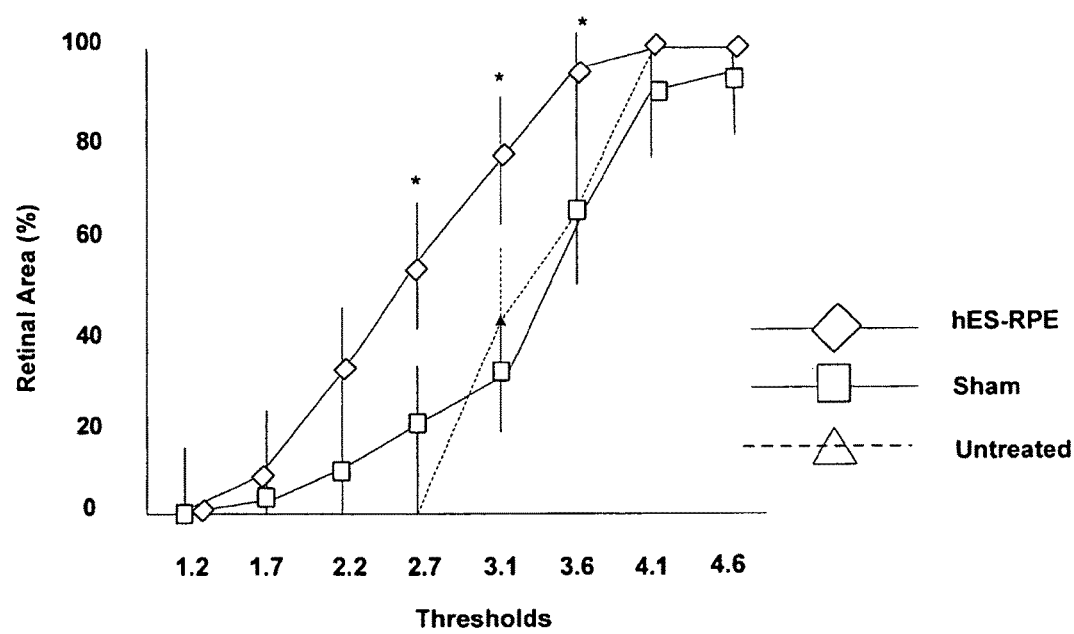
FIG. 11 Luminance threshold at P100—luminance threshold responses recorded across the superior colliculus, each curve (average SEM) shows the percent of retinal area (y-axis) where the visual threshold is less than the corresponding value on the x-axis (log units, relative to background illumination 0.02 cd/m$^2$). Asterisks show the points where the curves for grafted and sham-operated eyes are statistically different (t-test, p<0.05).

Average and best performers in the optomotor test were selected from each group for luminance threshold response testing. Results were obtained from animals receiving hRPE cells (n=7), sham injections (n=5), and no treatment (n=6). In non-dystrophic rats, a threshold response of less than 0.6 log units is recorded. On P100, untreated RCS rat neurons across the whole visual field failed to respond with thresholds of 2.7 log units or better, while responses could be elicited from 18% of the area in sham-injected rats. By comparison, the cell-injected rats showed 52% of the collicular area with thresholds of 2.7 log units or better, with a best point of 1.3 log units (FIG. 11).

Histological examination of the retinas demonstrated the presence of human specific nuclear marker that also stained for RPE-specific markers (RPE65 and bestrophin). Staining with human-specific proliferating cell nuclear antigen (PCNA) was negative, indicating that there was no proliferation of the hRPE cells. In addition, the histology revealed persistence of the cell population without inflammation or immune cell infiltration and without cellular proliferation or tumor formation.

The results of this study indicate that there was significant visual rescue above controls as determined by all three functional assessments. The cells survived long-term (>100 days) after transplantation into RCS rats, and localized to the subretinal space without migration into the retina. In addition to extensive photoreceptor rescue (5-7 cells deep in the outer nuclear layer), the relative acuity as measured by the optomotor system showed that animals treated with hES-derived hRPE performed significantly better than sham and untreated controls (50% and 100% improvement in visual performance, respectively; visual acuity was approximately 70% that of normal non-dystrophic rats). There was also no evidence of any tumor formation.

In these experiments, the transplantation of RPE cells resulted in the maintenance or improvement of visual function. Therefore RPE cells described herein may be used in a cell therapy for treating retinal degenerative disease such as the amelioration of age-related macular degeneration (AMD) and senile macular degeneration (SMD).

Example 22

Long-Term Safety and Function of RPE from Human Embryonic Stem Cells in Preclinical Models of Macular Degeneration Summary of Results The RPE cells described herein may be used for the treatment of age-related macular degeneration and Stargardt's disease. Here we show long-term functional rescue using hESC-derived RPE in both the RCS rat and Elovl4 mouse, animal models of retinal degeneration and Stargardt's, respectively. Good Manufacturing Practice-compliant hESC-RPE survived subretinal transplantation in RCS rats for prolonged periods (>220 days). The cells sustained visual function and photoreceptor integrity in a dose-dependent fashion without teratoma formation or untoward pathological reactions. Near-normal functional measurements were recorded at >60 days survival in RCS rats. To further address safety concerns, a Good Laboratory Practice-compliant study was carried out in the NIH IR immune-deficient mouse model. Long-term data (spanning the life of the animals) showed no gross or microscopic evidence of teratoma/tumor formation after subretinal hESC-RPE transplantation. See Lu, et al. (2009) Stem Cells 27: 2126-2135.

Animals and Experimental Designs

Pigmented dystrophic RCS rats (n=79) and ELOVL4 mice (n=28) were used in the main experiments. NIH III immunonude mice (n=45) were used for safety study. For RCS rats, animals were divided into live groups according to the doses they received. They were $5 \times 10^3$ (5,000)/eye (n=21), $2 \times 10^4$ (20,000)/eye (n=21), and $5 \times 10^4$ (50,000)/eye (n=21). Animals from all dosage groups received cells with low medium and high pigmentation. All above the dosage group animals were received cells with low, medium and high pigmentation (Table 14). For further comparison, two groups were added: one group of animals (n=8) received $7.5 \times 10^4$ (75,000)/eye cells and another group (n=8) received $1 \times 10^5$ (100,000)/eye cells with medium pigmentation. For ELOVL4 mice, the eyes received $5 \times 10^4$ (50,000)/eye cells with medium pigmentation. All animals in the main experiments were maintained on oral cyclosporine A administered in the drinking water (210 mg/l, resulting blood concentration of ~300 μg/l) from 1 day before transplantation until they were sacrificed. An intraperitoneal injection of dexamethasone was given for 2 weeks (1.6 mg/kg/day) after surgery in cell and control injected rats and for 2 weeks alone in untreated animals. All animals were maintained under a 12-hour light/dark cycle.

Cell Preparation

Culture of hES cells and Differentiation into Mature RPE Cells.

All cell manufacturing procedures were carried out in ISO Class 5 biosafety cabinets in an ISO Class 7 clean room facility under strict environmental control monitoring systems and a routine microbial testing regimen. Single-blastomere hESC lines MA01 and MA09 were maintained as previously described herein. hES cells were dissociated from the primary mouse embryonic fibroblast layer by treatment with 0.05% trypsin-EDTA and were seeded in 6-well low-attachment plates to allow EB formation in a chemically defined minimal essential medium (MEM)-based medium (MDBK-GM) containing B-27 supplement for about 7 days and plated on gelatin-coated (0.1%) dishes until RPE colonies were visible. RPE was purified by 3-hour exposure to 4 mg/ml type IV collagenase and manually isolated with a glass pipette. Purified RPE was seeded onto gelatin-coated tissue culture plates and expanded in EGM-2 medium until desired density was achieved, at which point cultures were reverted to MEM-based medium (MDBK-MM) and cultured until the appropriate phenotype was achieved. RPE was dissociated from culture using a 1:1 mixture of 0.25% trypsin-EDTA and Hanks-based cell dissociation buffer and was cryopreserved in 90% fetal bovine serum and 10% dimethylsulfoxide Quantitative, Real-Time, Reverse Transcription-Polymerase Chain Reaction.

RNA was extracted from the cells using TRIzol reagent according to the manufacturer's protocol. Eluted RNA was quantitated by spectrophotometry, and 10 μg was subjected to DNase digestion, followed by a reverse transcription reaction using a QUANTITECH® reverse transcription kit with a mixture of oligodT and random hexamers primers. Fifty NANOGrams per well of cDNA was used as templates in quantitative polymerase chain reactions (qPCRs) with oligonucleotides specific for hESC and retinal genes. All qPCR reactions were performed in triplicate, with the resultant values being combined into an average threshold cycle (CT). The efficiency of qPCR was calculated from the slope of a relative standard curve using GAPDH primers. Relative quantization was determined using a STRATAGENE® MX3005P QPCR system measuring real-time SYBR Green fluorescence and calculated by the $\Delta\Delta CT$ method. Fold differences are calculated using the $\Delta\Delta Ct$ in the formula $2-\Delta\Delta Ct$. Expression profiles for the mRNA transcripts are shown as fold differences in comparison to mRNA levels in hES cells.

Microarray Gene Expression Profiling.

Global gene expression analysis was performed using the human AFFYMETRIX® HGU133 Plus 2.0 microarray platform on both of the single blastomere-derived hESC lines MA01 and MA09 and the resulting RPE cells derived from each. Additionally, fetal RPE, ARPE-19, and retinoblastoma cell lines were used as controls Western Blot Analysis.

Immunoblot analysis was carried out using standard SDS-PAGE methods using the BIO-RAD® Mini-Protean and Mini-Transblot Cell. The protein bands were visualized using Western Lightning Chemiluminescence Reagent and a KODAK® 4000 MM digital imaging station. Commercially available antibodies specific for DPPA4, TDGFI β-actin, CHX-10, Otx2, REX1, RPE65, PAX6 Bestrophin, CRALBP, Pax2, MitF, NANOG, Oct4, PEDF, and Tyr as well as horseradish peroxidase-conjugated secondary antibodies were used.

TABLE 15

Number of eyes treated at each pigment level

| Number of cells | Low pigment | Medium pigment[a] | High pigment |
|---|---|---|---|
| 5,000 | 8 | 6 | 7 |
| 20,000 | 7 | 8 | 6 |
| 50,000 | 7 | 7 | 7 |
| Sham | 12 | 12 | 11 |
| Untreated | 9 | 10 | 10 |

[a]Sixteen additional eyes in the ""medium pigment" group were also treated with a higher dosage: 75,000 (n = 8) and 100,000 (n = 8) cells.

Transplantation Protocol

Before cell transplantation, cells were thawed and washed in balance salt solution (BSS) and suspended in BSS. Three cell lines designated low, medium, and high pigment were given in different dose groups. These are summarized in Table 15. Using techniques known in the art, a suspension of cells was delivered into the subretinal space of one eye through a small scleral incision, suspended in 2 μl of BSS medium using a fine glass pipette (internal diameter, 75-150 μm) attached by tubing to a 25-μl Hamilton syringe. The cornea was punctured to reduce intraocular pressure and to limit the efflux of cells. A sham-surgery group was treated the same way, except the carrying medium alone was injected. Pigmented dystrophic RCS rats received unilateral subretinal injections of the cell lines (n=79 eyes) at P21; control rats received sham alone (n=35 eyes) or were untreated (n=29 eyes). Elovl4 mice at P28 received cells (n=12 eyes), sham alone (n=8 eyes), or were untreated (n=8 eyes). Immediately after injection, the fundus was examined for retinal damage or signs of vascular distress. Any animal showing such problems was removed from the study and excluded from the final animal counts.

Spatial Visual Acuity.

Animals were tested for spatial visual acuity using an optometry testing apparatus comprising four computer monitors arranged in a square, which projected a virtual three-dimensional space of a rotating cylinder lined with a vertical sine wave grating. Unrestrained animals were placed on a platform in the center of the square, where they tracked the grating with reflexive head movements. The spatial frequency of the grating was clamped at the viewing position by recentering the "cylinder" on the animal's head. The acuity threshold was quantified by increasing the spatial frequency of the grating using a psychophysics staircase progression until the following response was lost, thus defining the acuity. Rats were tested from P60 to P240 at monthly intervals. Elovl4 mice were also tested in this apparatus at 3, 5, 7, and 11 weeks after surgery.

Luminance Threshold.

This was studied to provide a different measure of function from the spatial acuity and was achieved by recording single and multiunit activity close to the surface of the superior colliculus (SC) using glass-coated tungsten electrodes (resistance: 0.5 MΩ; bandpass 500 Hz to 5 KHz) with previously described procedures. Recordings were made only in rats, selected on the basis of good and representative optomotor results: mice were not examined with this test. The brightness of a 5° spot was varied using neutral density filters (minimum steps of 0.1 log unit) over a baseline level of 5.2 log units until a response double the background activity was obtained: this was defined as the threshold level for that point on the visual field. A total of 15-20 positions were recorded from each SC. All animals were recorded at about P100, and some were studied again at a second time point at about P190. Data are expressed as a graph of percentage of SC area with a luminance threshold below defined levels and as raw results.

Histology.

At the end of functional tests, all animals were euthanized with an overdose of sodium pentobarbital and perfused with phosphate-buffered saline. The eyes were removed, immersed in 2% paraformaldehyde for 1 hour, infiltrated with sucrose, embedded in optical cutting temperature, and cut into 10-μm horizontal sections on a cryostat. Four sections (50 μm apart) were collected per slide, providing five series of every fourth section collected. One was stained with cresyl violet for assessing the injection site and integrity of retinal lamination. The remaining slides were used for antibody staining, following previous protocols, and were examined by regular and confocal microscopy.

Safety Study.

Cells were prepared and transplanted using the same methodology described above for the RCS rat study. A minimum of six NIH III mice per group were injected with either hES cells or hESC-derived RPE from the MA09 single blastomere cell line in three time-based cohort groups (n=36). The animals were killed by $CO_2$ inhalation followed by exsanguination at 1, 3, and 9+ months based on cohort. Three negative control animals were also put in the study for each cohort (n=9). Life study assessments included routine clinical assessments and body weight analysis, plus pre-sacrifice clinical chemistry. Post mortem, eyes were removed and immersed in cold 4% paraformaldehyde, for up to 1 week. The tissue was embedded in paraffin and sectioned. Select slides were stained with hematoxylin and eosin. Slides were examined microscopically to assess retinal lamination and tumor formation.

Differentiation and Characterization of hESC-Derived RPE

Human RPE cells were generated using a cGMP-compliant cellular manufacturing process. Three different batches of RPE were created from each blastomere-derived hESC line based on morphological assessment of pigmentation (FIG. 15), an important indicator of RPE maturation.

Each production run generated about $50\times10^6$ RPE cells from a single frozen ampule of $1\times10^6$ hES cells. This amount is sufficient to dose about 500 rats or 50-100 human subjects. Additionally, the methods described herein are completely suitable to available scale-up technologies such as bioreactor culture or large-scale fluid handling systems.

To characterize the developmental stages during RPE differentiation, several assays were used to identify the expression levels of genes key to each stage of development. qPCR was developed to provide a quantitative and relative measurement of the abundance of cell type-specific mRNA transcripts associated with the RPE differentiation process. A panel of genes associated with hESC pluripotency (Oct-4, NANOG, Rex-1, TDGF1, Sox2, DPPA2, and DPPA4), neuroectoderm intermediates (PAX6 and Chx10), and RPE (RPE-65, Bestrophin, CRALBP, PEDF, MitF, Otx-2, Tyr, and Pax2) was established and assayed for each by qPCR. With regard to quality control of cellular manufacturing, the marked decrease in all stem-related genes and concomitant increase in all retinal-associated genes, at a level of 10- to 100-fold, was deemed acceptable release criteria.

Figure 12:
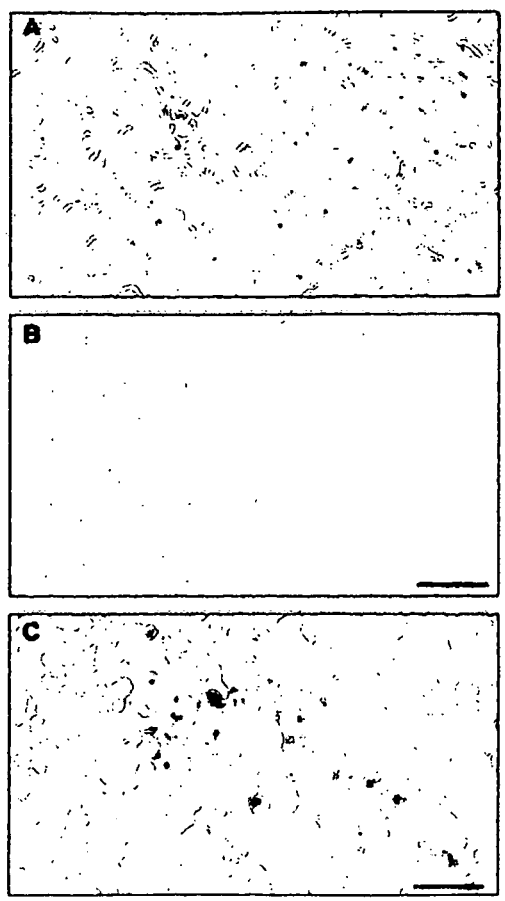
FIG. 12 depicts in vitro maturation and degree of pigmentation in different batches of human ES cell-derived RPE cells. hES cells were matured to yield (A) light (L1), (B) medium (L2), and (C) heavy (L3) pigmentation levels. (A): Phase contrast image; scale bar 200 gm. (B and C): Hoffman modulation contrast image; scale bar=100 μm.
Figure 13:
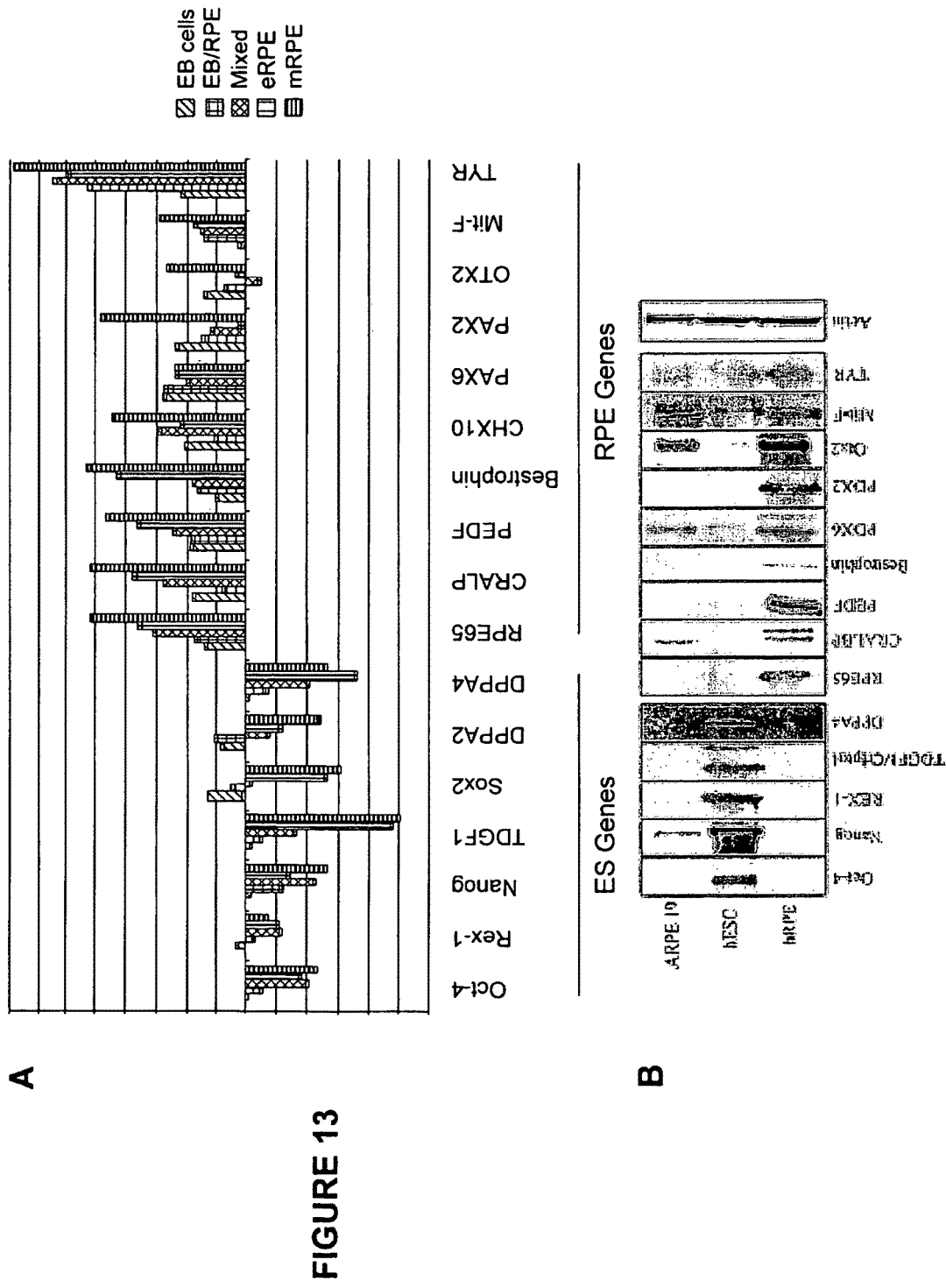
FIG. 13 depicts comparative assessment of hES cell-RPE cells using real-time polymerase chain reaction (PCR) and Western blot analyses. (A): Reverse transcription-PCR analysis of genes specific to hES cells, neuroectoderm, and terminally differentiated RPE cells examined throughout the in vitro differentiation process. Time points correspond to hES cells, EBs, plated EBs representing early intermediates (EB/RPE), a mixed population of cells containing newly differentiated RPE cells, remaining progenitors (Mixed), purified RPE (corresponding to FIG. 12A), and fully-mature RPE (corresponding to FIG. 12C). (B): Western blot analysis of hESC-specific and RPE-specific markers. APRE-19 cells (top lane) show an inconclusive pattern of proteomic marker expression. Actin is used as protein loading control. RPE (bottom lane) derived from hES cells (middle lane) do not express the hES cell-specific proteins Oct-4, NANOG, Rex-1, TDGF1, and DPPA4. However, RPE cells express RPE65, CRALBP, PEDF, Bestrophin, PAX6, Pax2, Otx2, MitF, and Tyr—all markers of differentiated RPE.

FIG. 13 shows the gene expression profile of the transcripts during differentiation to mature RPE, including samples from hES cells (d0), embryoid bodies (EBs, d7), plated EBs (d14), mixed population of newly formed RPE and less differentiated cells (mixed, d28), purified early RPE (eRPE, d35), and fully matured pigmented RPE (mRPE, d56). A progressive decrease in the expression level of hESC-specific genes (FIG. 13A) was accompanied by an increase in the level of neu-roectoderm and RPE-specific genes. Lightly pigmented RPE (FIG. 12) expressed 1,000-fold lower quantities of Oct-4, NANOG, Sox2, and DPPA4; <10,000-fold less TDGF1; and 50-fold less Rex-1 and DPPA2 than hESC. The cells also expressed 10- to 100-fold greater quantities of RPE65, CRALBP, PEDF, Bestrophin, PAX6, and MitF and expressed >100,000,000-fold Tyr, a downstream target of MitF/Otx2 in RPE. This cell population expresses genes such as PAX6 and CHX10 because this stage represents an "immature" population of RPE derived from embryonic cells, and may continue to express markers associated with developing cells of the neuretina and/or neurectoderm.

The phenotypic changes that RPE undergoes during the in vitro maturation process were characterized by qPCR (FIG. 12A-C). FIG. 12A shows that RPE with a higher degree of pigmentation and polygonal cell borders (corresponding to FIG. 12C) maintains higher expression of RPE-specific genes. Notably, both pigmentation and the high level of RPE-specific gene expression are correlated with the emergence of Pax2 expression and a sharp increase in MitF, Otx2, and Tyr expression. MitF expression, and in turn Tyr, is achieved in RPE through synergy of Pax2 and PAX6 during embryonic development.

Proteomic Validation of Selected Transcripts in hESC-Derived RPE

To verify that genes of interest were expressed at the protein level, all targets of the initial transcriptional profile panel were assayed by Western analysis. As an internal control, hESC-derived RPE was compared with the ARPE-19 cell line by both qPCR and Western analysis. FIG. 10A shows that, although hESC-RPE expresses similar levels of RPE-specific transcripts to ARPE-19, the hESC-RPE expresses more abundant levels of these proteins (RPE65, PEDF, Pax2, and Bestrophin). Additionally, proteins expressed by hES cells are all downregulated in the final differentiated cell product. This disappearance of stem-related proteins (by immunoblot) and concomitant emergence of retinal-associated proteins is indicative of RPE cells as described herein.

Bioinformatic Analysis of Global Gene Expression in hESC-RPE

Figure 14:
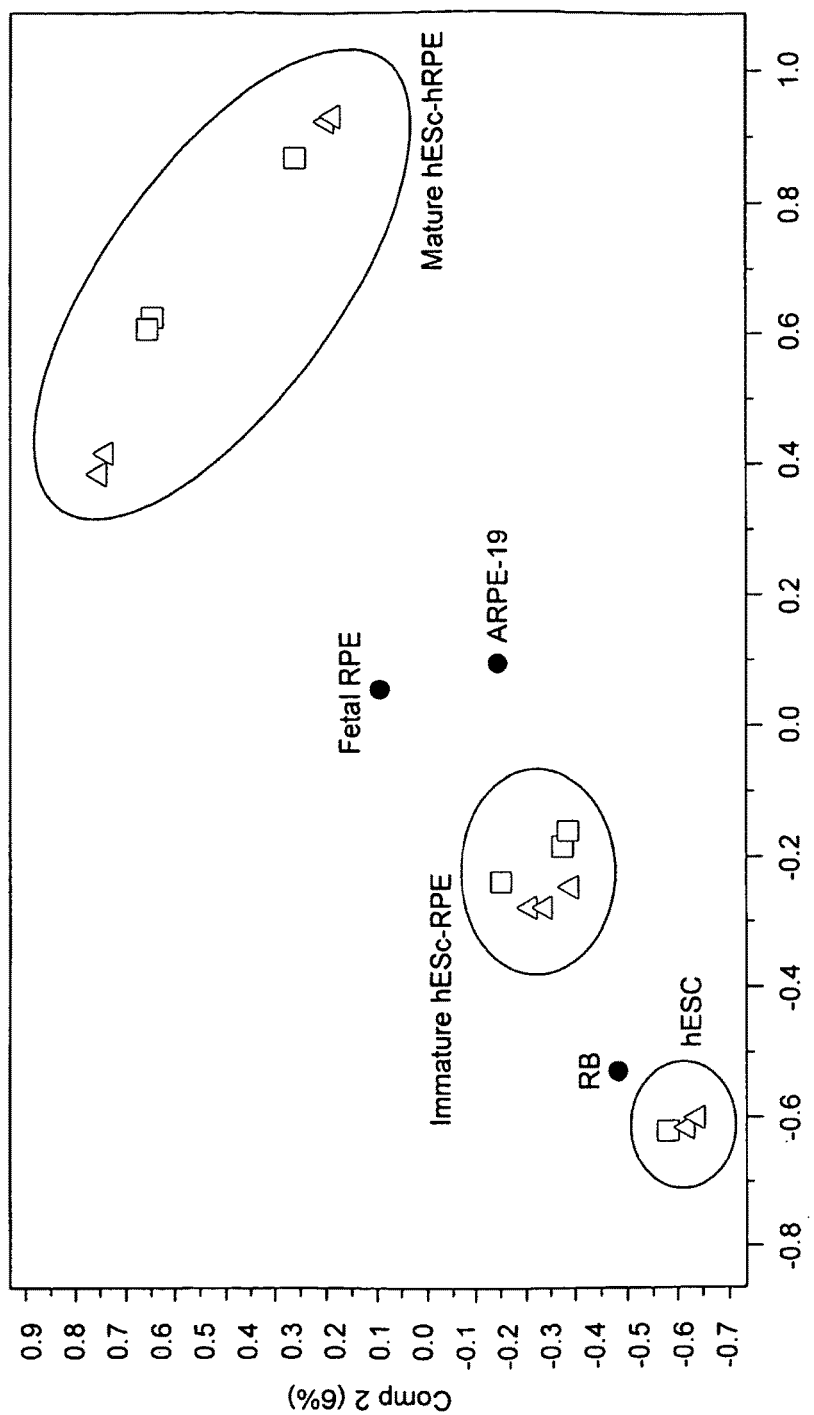
FIG. 14 depicts principal components analysis plot. Component 1 represents 69% of the variability represents the cell type, whereas component 2 represents the cell line (i.e., genetic variability). A near-linear scatter of gene expression profiles characterizes the developmental ontogeny of RPE derived from hES cells.

The biological relevance of the morphological changes observed in vitro were assessed by gene expression profiling and subsequent informatic analysis of both hESC lines, each with three different morphologies: a control and several "reference" cell lines on the human Affymetrix® HG-U133 Plus 2.0 microarray platform. FIG. 14 shows a principal component analysis (PCA) scatter plot, indicating the contribution to variance that the two major variables, cell type and cell line (x- and y-axis, respectively), yield on global gene expression. A linear progression was observed from the undifferentiated (hES cells) state through the three levels of RPE pigmentation. Interestingly, the depigmented RPE cells (See FIG. 12A) cluster closer to both ARPE-19 and fetal RPE; the latter display similar Morphological characteristics to this batch of cells in vitro. The more heavily pigmented batches of RPE cells appear to cluster farther from hES cells and retinoblastoma cells (RB) than any other cell type tested. Whereas the pigmented batches of RPE from MA01 and MA09 do not overlap by PCA, they are within a similar order of magnitude to each other to that of fetal RPE and ARPE-19. Taken together, these data suggest that the more heavily pigmented hESC-RPE cells may be considered the most differentiated, and from a safety standpoint, the most genetically divergent from cells possessing "sternness" or expressing cancer-related genes.

Pathogen Testing and Stability of RPE

An important criterion to consider in the use of RPE cell preparations for therapeutic applications is product safety (e.g., contamination or infection with viral or bacterial agents). To ensure that the RPE cells were free of contamination during the extensive culture and differentiation process, the following testing according to U.S. Food and Drug Administration and International Conference on Harmonization guidelines for applicable microbial and viral agents were conducted: United States Pharmacopeia membrane filtration sterility, fluorochrome-based mycoplasma, transmission electron microscopy for viral particles, in vitro tissue culture safety testing for adventitious agents, in vivo inapparent virus detection, PCR-based reverse transcriptase detection, HIV-1, HIV-2, HBV, HCV, CMV, HTLV-1 and -2, parvovirus B19, Epstein-Barr virus, and herpesvirus 6. Additionally, the cells were cytogenetically analyzed by G-banding karyo-type analysis. Results confirmed that these cell lines are karyotypically stable and substantially free of infectious pathogens.

Dosing Studies in RCS Rats.

The effect of different doses on efficacy was titrated using the optomotor response as an indicator. The results at P90 (70 days after transplantation) are summarized in FIG. 15A. Improved rescue of spatial acuity occurred from 5,000 to 50,000, after which even doubling the dose of cells to 100,000 had no significant effect on efficacy. Performers among the cell-injected group gave a figure of 0.536 cycles/degree (c/d) compared with 0.6 c/d in normal rats, which is about 90% of normal value. There was no significant difference between sham and untreated groups, which performed significantly worse than the cell-injected group ($p<0.01$).

Luminance thresholds were also measured in a subset of rats selected by their performance on the optomotor response. An area with high sensitivity corresponded to the area of retina in which the cells were introduced, as indicated in FIG. 15C-15F. For statistical comparison the data for this part of the example is presented as a percentage of the area of the visual field representation from which thresholds better than designated levels were recorded without regard to position. This gives a simple indicator of overall efficacy, as well as a response figure, dissociated from spatial considerations. It is clear that the overall sensitivity recorded at 50,000 is superior to 20,000, but as with spatial acuity, it does not change significantly between 50,000 and 75,000. For example, about 45% of the SC gave thresholds of 2.2 log units with 50,000 cells/eye and about 40% with 75,000 cells/eye. Generally, the mean response levels at 100,000 were better and gave more long-lasting rescue than did lower doses. See FIGS. 15 and 16.

Pigmentation Results

Figure 17:
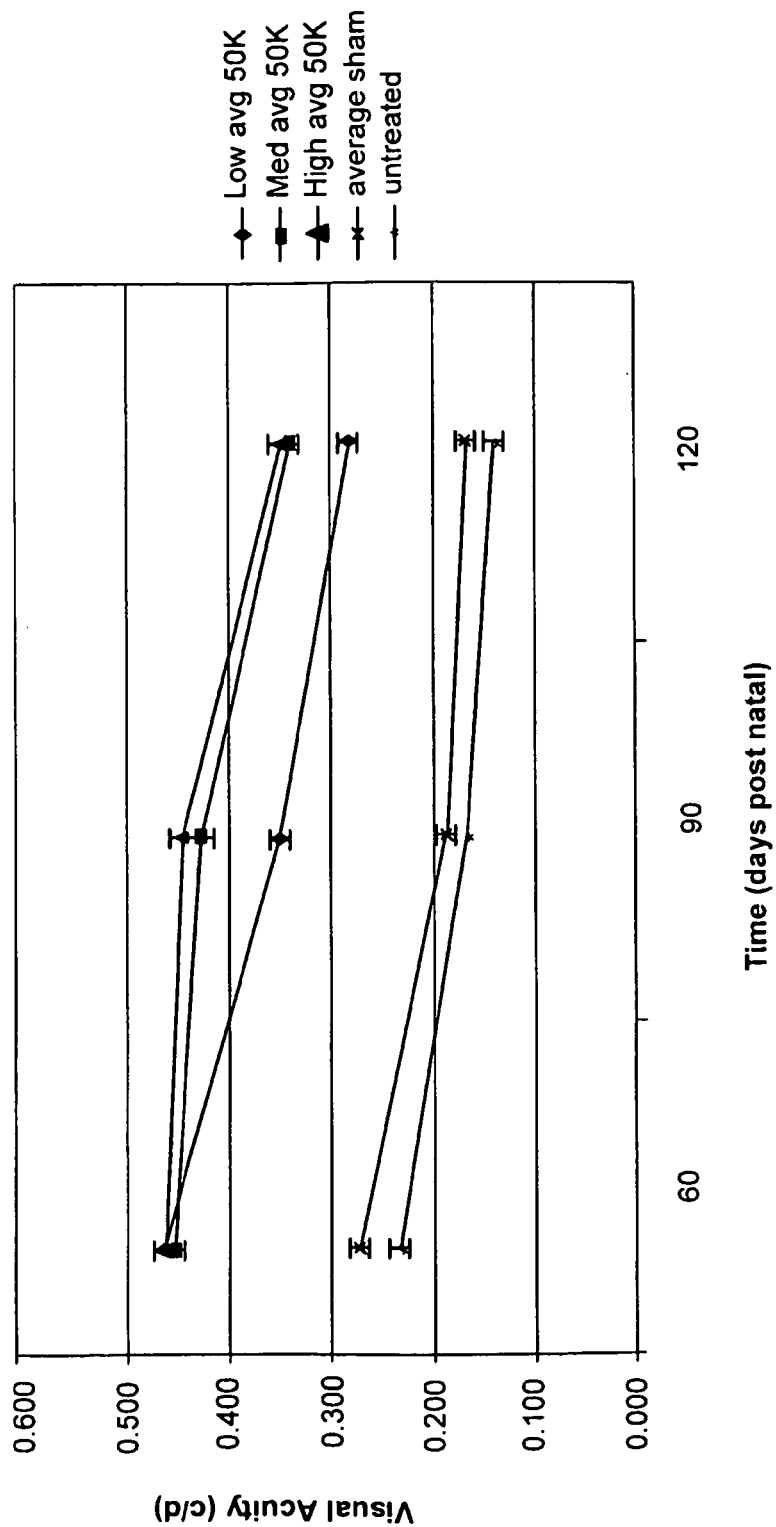
FIG. 17 depicts a comparison of the effects of pigmentation on the efficacy of RPE cells in a RCS rat model. The rats were transplanted with 50,000 RPE cells with low, medium, or high pigmentation levels. These rats were compared to sham surgery and untreated controls.

There was no significant difference between pigment groups on visual acuity (FIG. 17), however, compared to the sham or untreated controls, all pigment groups did show significantly better visual acuity at all time points between P40 and P240.

Batch and Longevity of Effect in RCS Rats

Although slight differences in optomotor acuity were seen between the different pigment levels (Table 14), they were not significant. In contrast, there was a significant difference at all time points studied between the cell-injected groups and medium-injected and untreated controls. See FIG. 16. Over time, there was a reduction in acuity response for all the cell groups and dose levels.

To examine how luminance responses deteriorated with time, thresholds were recorded at two time points in individual rats. An example is shown in FIG. 18. As shown, the luminance thresholds show serious deterioration on the untreated side, with more than one half the area being nonresponsive at P187 compared with P98, whereas responsiveness is still sensitive on the cell-injected side, although some reduction in thresholds has occurred (0.7 log units at P98 vs. 1.0 log units at P187). Raw data from an animal that received cell injection: luminance threshold responses were recorded at P98 (shown in FIG. 18A) and P187 (shown in FIG. 18B) in the same rat from multiple points within the superior colliculus (SC). This method quantifies functional sensitivity to light across the visual field of the eye. The topographical map depicts the luminance threshold responses (measured in log units relative to background illumination of 0.02 cd/m$^2$) at 15 and 16 points in the left and right sides, respectively, within the SC. In FIG. 18A, all points of luminance threshold responses in the treated side are less than 2.0 log units, whereas in the untreated side, all points are greater than 2.3 log units. Table 15B depicts the same animal was recorded at P187 (>5 months after surgery); there is deterioration in sensitivity to light compared to P98; however, it is still significantly better than the untreated fellow eye (which has no response over half the area). Abbreviation: c/d, cycles/degree. See FIG. 18.

Efficacy in Elovl4 Mice

Figure 15B:
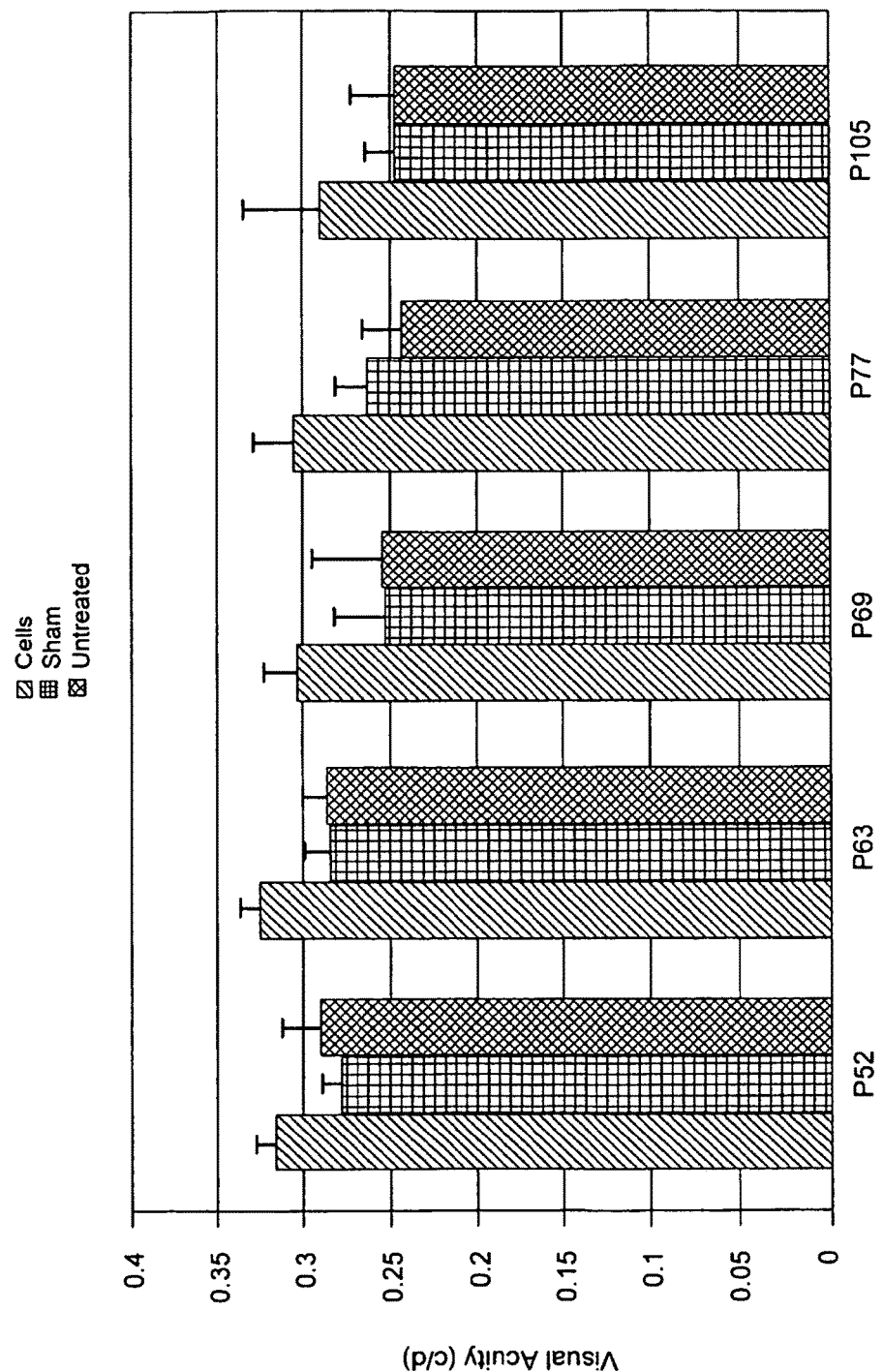
FIG. 15 depicts (A): visual acuity as measured by the optomotor response shows that animals treated with 5,000, 20,000, 50,000, 75,000, and 100,000 cells performed significantly better than those with sham injection and untreated controls (p<0.01) at P90 days (e.g., a figure of 0.563 c/d compared with 0.6 c/d in normal rat). (B): Visual acuity tested in Elovl4 mice at several time points after subretinal injection of human RPE cells showed that cell-injected animals performed significantly better than medium-injected and untreated controls (p<0.05). Some showed a figure of 0.32 c/d at P63 compared with 0.35 c/d in normal mice, whereas control animals had a figure of 0.28 c/d. (C-F): Luminance threshold responses recorded across the superior colliculus (SC); each curve (average±SEM) shows the percent of retinal area (y-axis) where the visual threshold is less than the corresponding value at x-axis (log units, relative to background illumination 0.02 cd/m$^2$). Cell-injected groups are significantly better than controls: the curves showed that 28% of the area in the SC in animals with the (C) 20,000 RPE cell dose; (D) about 45% with the 50,000 RPE cell dose; (E) about 40% with the 75,000 RPE cell dose; (F) about 60% with the 100,000 RPE cell dose; and only 3% in medium control had thresholds of 2.2 log units. Dashed lines—cell-treated and Solid lines—medium control. Abbreviation: c/d, cycles/degree.
Figure 15C:
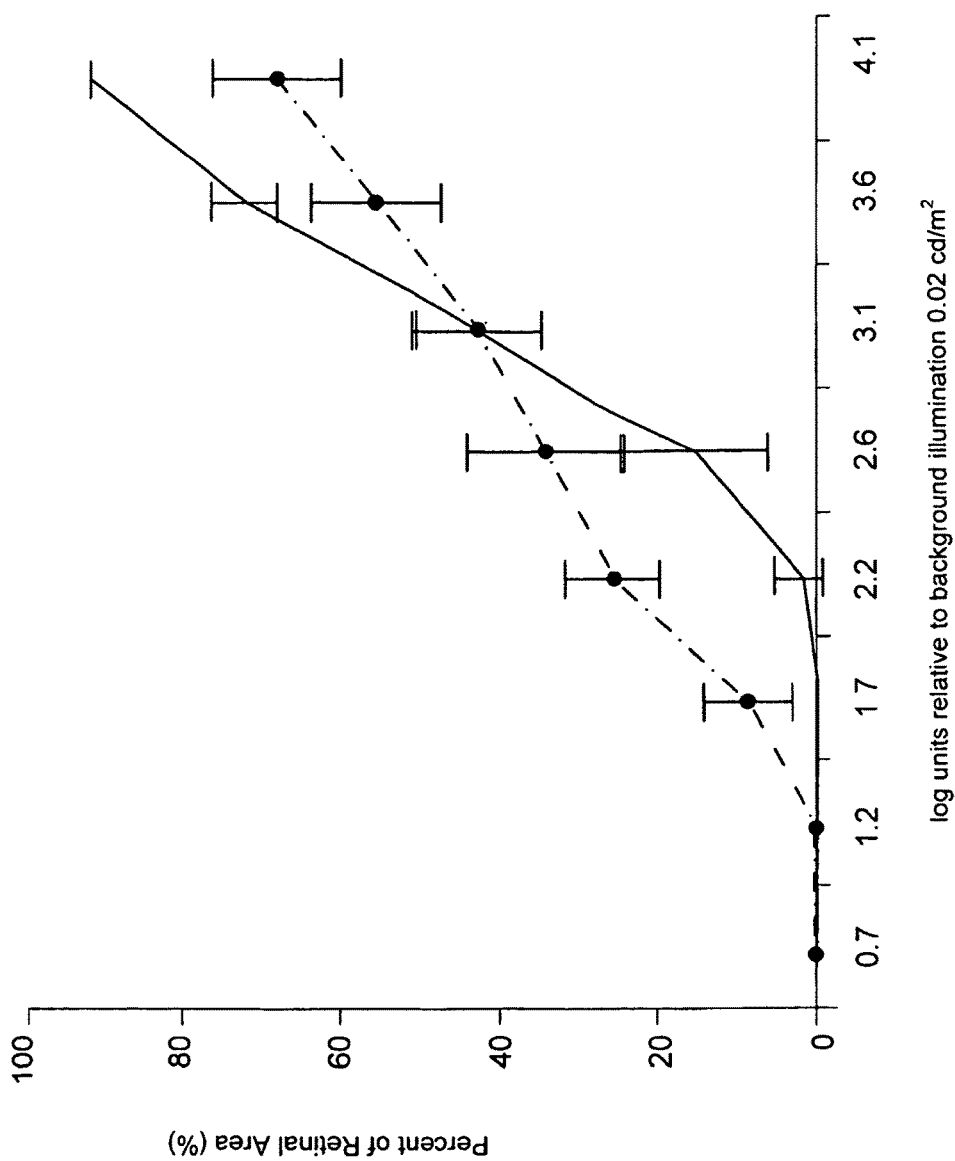
Figure 15D:
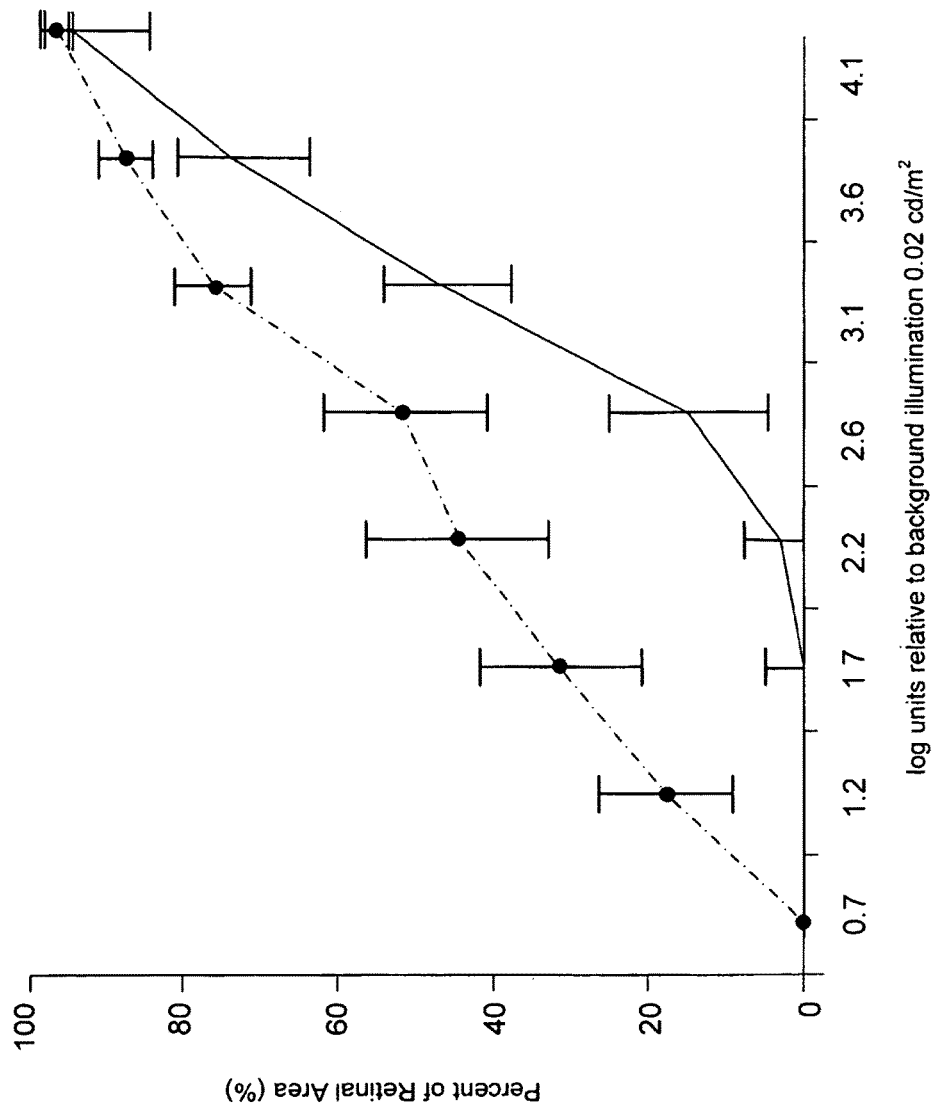
Figure 15E:
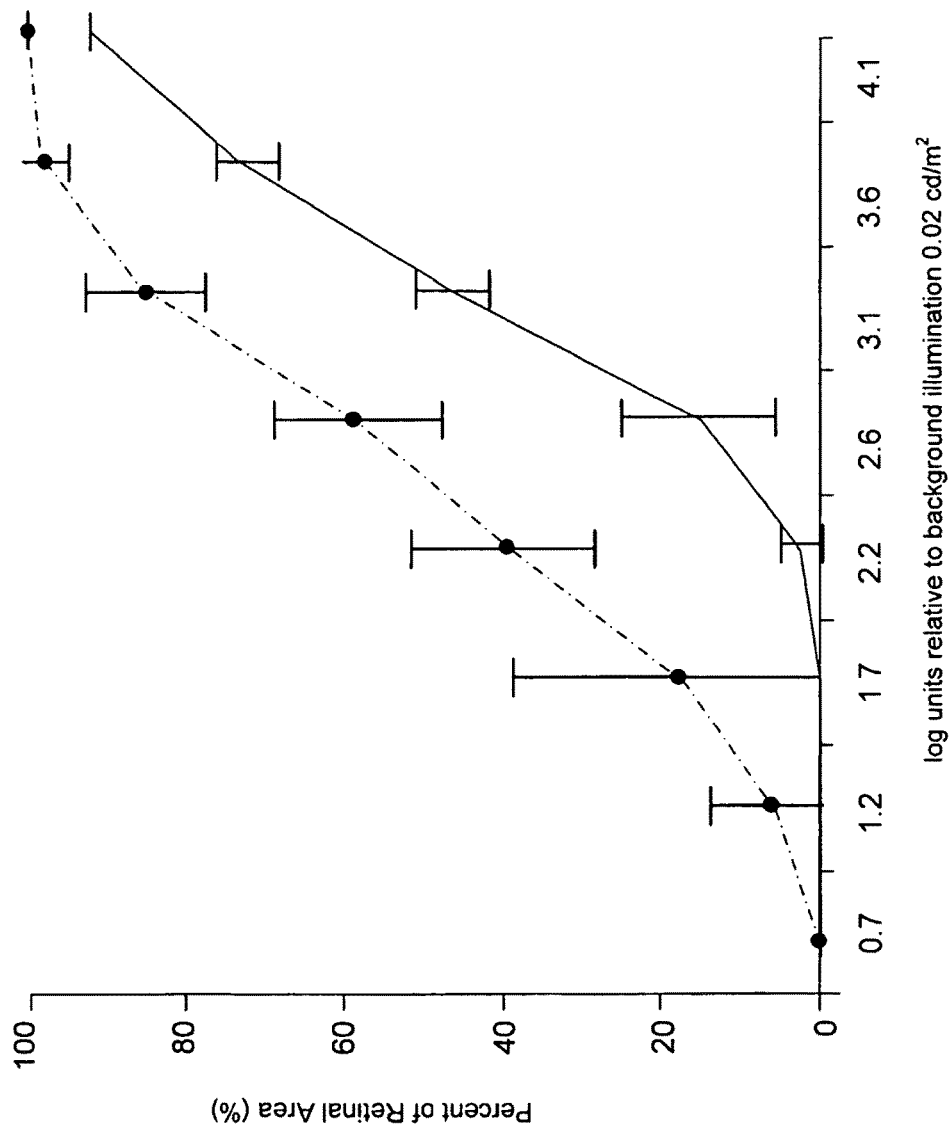
Figure 15F:
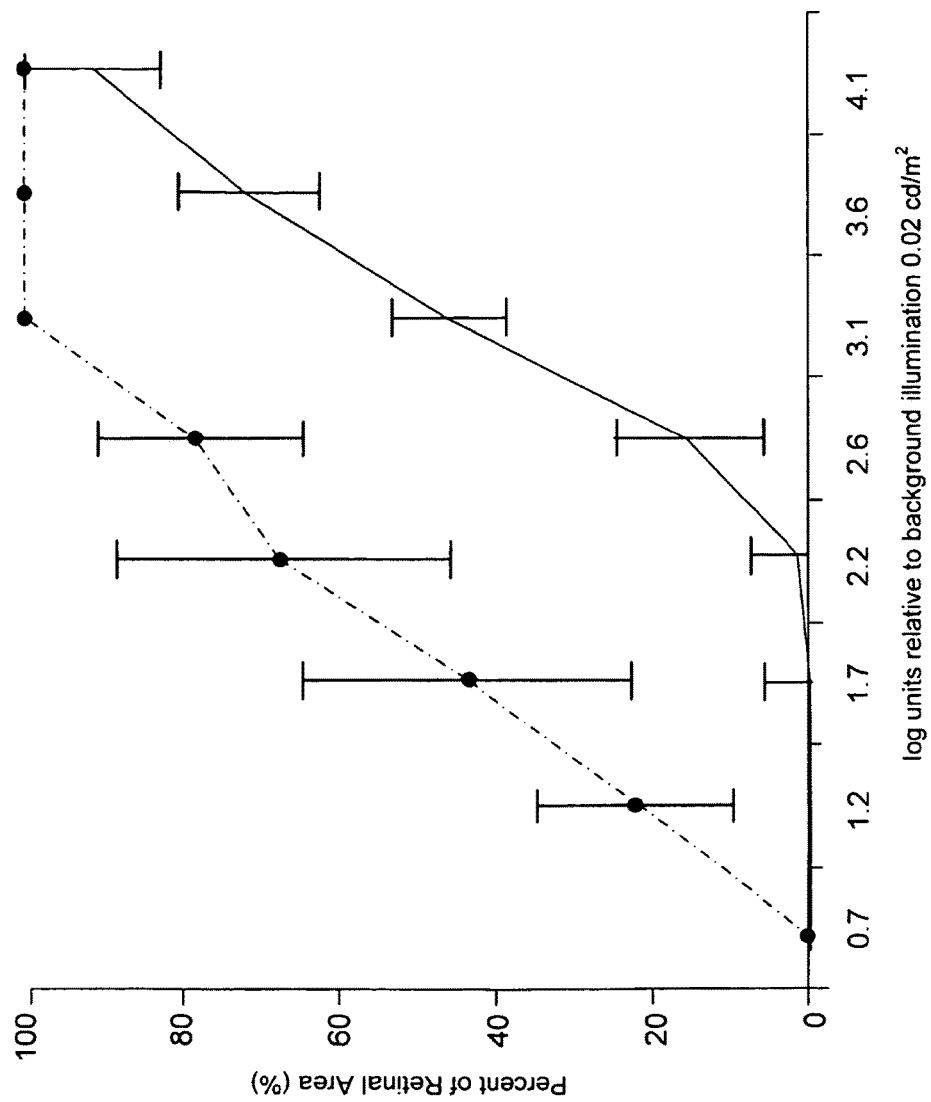
Figure 16:
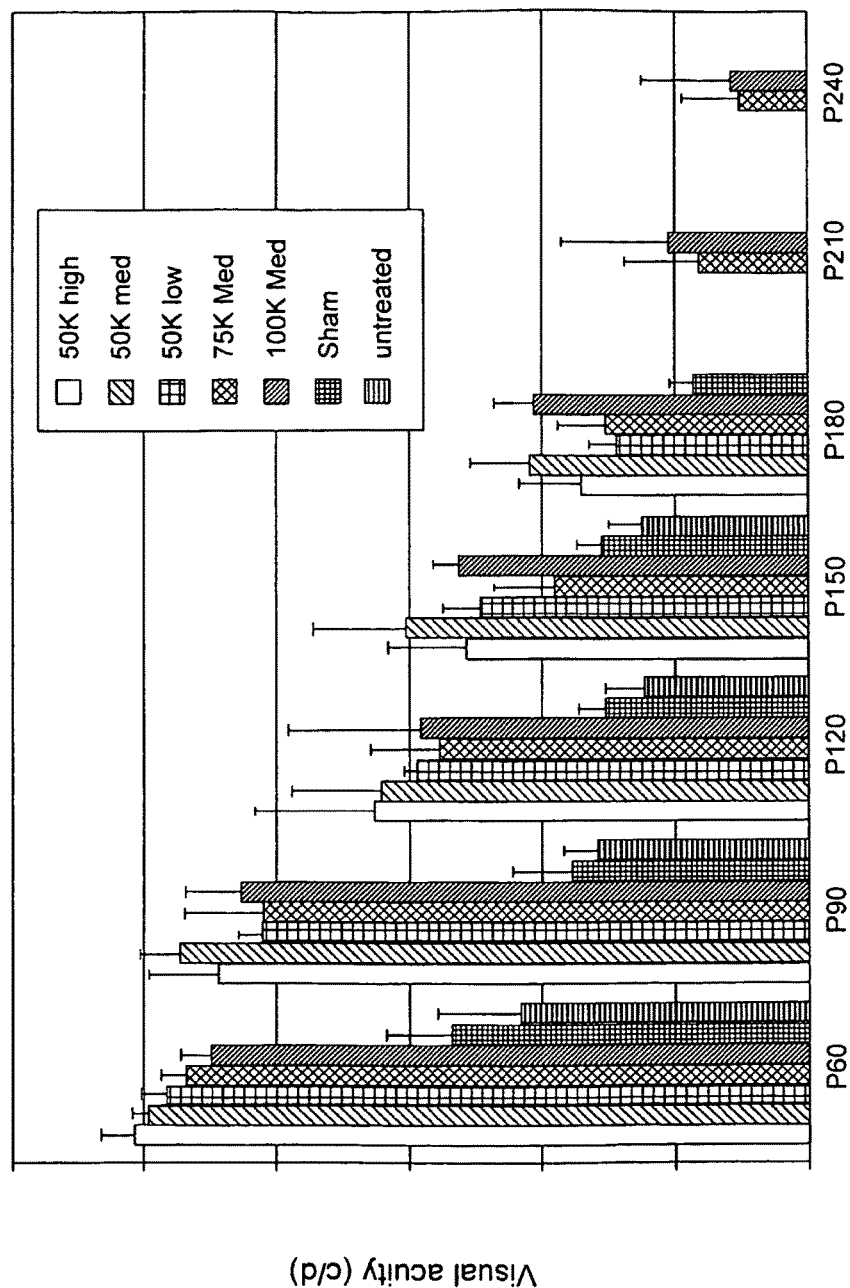
FIG. 16 depicts changes in acuity and luminance threshold with time. Batch and longevity of effect as measured by visual acuity: cell-injected groups at all the time points (P60-P240) had significantly higher visual acuities than controls (p<0.01); however, there is no substantial difference with different pigment levels (p>0.05). Abbreviation: c/d, cycles/degree.

Visual acuity in normal mice tested by the same optomotor device was lower than that in rats (0.35 vs. 0.6 c/d). In untreated Elovl4 mice, the visual acuity deteriorated as photo-receptor degeneration progressed from 0.34 c/d at P28 to 0.24 c/d at P105. FIG. 15B. Subretinal injection of hESC-RPE improved the visual acuity over controls at all time points tested. Cell-injected eyes had a figure of 0.32±0.04 c/d at P63 (5 weeks after surgery) compared with 0.26±0.03 c/d in sham-injected and untreated controls. FIG. 15B. Statistical analysis indicated that the difference between cell-injected and controls was significant (t test, $p<0.05$).

Histological Examination of RCS Rats

General Retina Structure.

Figure 19:
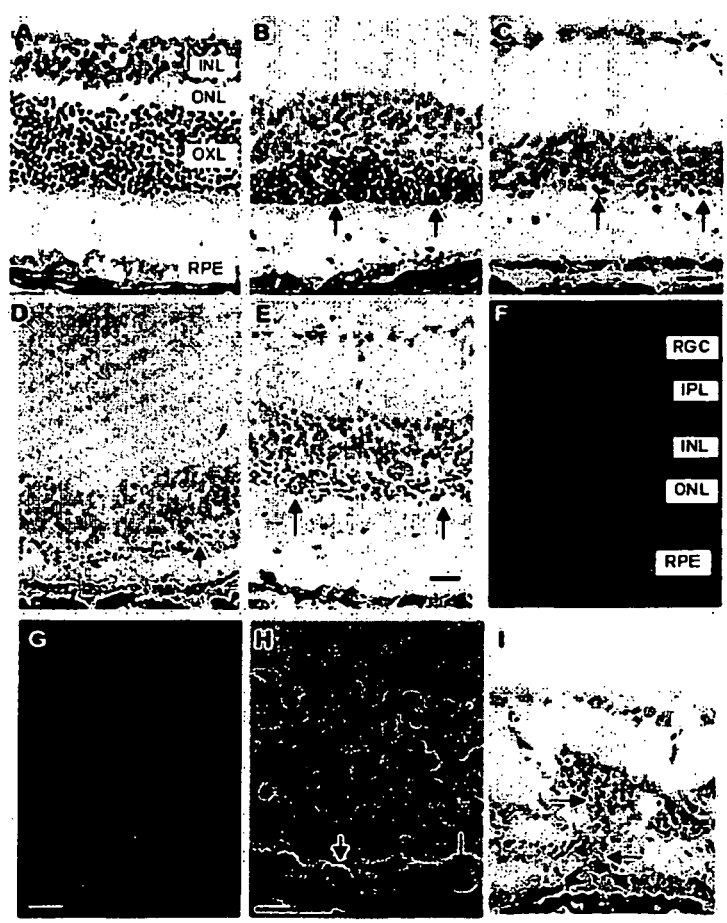
FIG. 19 depicts histological examination of cell-injected and untreated RCS retinas, showing photoreceptors in (A) normal, (B) cell injected, and (C) untreated eyes at P90 (arrows in B point to rescued photoreceptors; arrows in C indicate remaining photoreceptors). (D-F): Photoreceptors rescued at (D) 5,000 and (E and F) 50,000 dose (arrows in E indicate rescued photoreceptors; cone arrestin showed rescued cone photoreceptors in F). (G): Immunofluorescence- and (H) immunohistochemical-stained human specific antibody showing donor cells (arrows) formed a layer closely contact with the host RPE layer at P240. (I): Typical untreated retina at P240 with disorganized retinal lamination (left arrow indicates RPE cells migrating into inner retina; right arrow indicates disrupted inner nuclear layer). Scale bars 25 μm. Abbreviations: INL: inner nuclear layer; IPL: inner plexiform layer; ONL: outer nuclear layer; RPE, retinal pigment epithelium; RGC: retinal ganglion cells.

Retinal sections from cell-injected, sham, untreated, and normal control rats were stained with cresyl violet and examined under light microscopy. At P90, compared with normal control (FIG. 19A), the cell-injected retina had five to six layers of photoreceptors (FIG. 19B), whereas the untreated retina had only a single layer remaining (FIG. 19C). In accordance with the functional results, the 5,000/eye doses had slightly better photoreceptor rescue (FIG. 19D) than sham-operated (primarily with localized photoreceptor rescue around injection site), whereas the 20,000/eye produced better photoreceptor rescue. The 50,000/eye and greater doses gave consistent photoreceptor rescue, covering a larger area of the retina (FIG. 19E, 19F) with preserved cones. At P150, cell-injected retinas still had an outer nuclear layer two to three cells deep, and the inner retina lamination was not disrupted. In contrast, both untreated and sham-operated retinas showed a typical secondary pathology, including abnormal vascular formation, RPE cells, and inner retinal neurons migrating along abnormal vessels, leading to distortion of retina lamination. At P240, cell-injected retinas still had an outer nuclear layer of one to two cells deep, and the inner retina still showed an orderly lamination. In contrast, advanced degeneration was evident in control retinas: the inner nuclear layer became irregular in thickness, ranging from one layer to multiple layers; RPE cells had migrated into the inner retina; and abnormal blood vessels were seen (FIG. 19I).

Antibody Staining.

The human specific nuclear marker, MAB1281 was used to identify the donor cells. They formed a layer, one to two cells deep, and integrated into the host RPE layer (FIG. 19G, 19H), as was seen in our previous study. Photoreceptor rescue continued beyond the limits of distribution of donor cells, suggesting that rescue was at least in part caused by a diffusible effect. Cone arrestin antibody showed that cone photoreceptors were preserved with disorganized segments (FIG. 19F) at P90. Donor cells were still evident up to at least P249 (FIGS. 19G and 19H). There was no indication of continued donor cell division (e.g., shown by the proliferating cell nuclear antigen marker).

Safety Assessment

Studies in NIH III Mice.

The long-term risk of teratoma formation was tested in the NIH III mouse model. The NIH III mouse was chosen for its immune-deficient status; the nude mouse has three mutations rendering it devoid of T cells, NK cells, and mature T-independent B lymphocytes. However, the NIH III mouse retains eye pigmentation, which provides better visualization for subretinal transplantation surgery. The surgical technique was the same as performed in the RCS study. The study compared the hESC-RPE to undifferentiated hES cells (positive control) to determine the teratoma formation potential of the 100,000 RPE cell dose over three time points: 1, 3, and 9 months (the approximate lifespan of the animal; n=6 per cohort). In contrast to the animals that received undifferentiated hES cells, no teratoma or tumor formation was found in any of the animals injected with the hESC-derived RPE. In addition, basic animal safety assessments were normal compared with controls.

Absence of Tumorigenic Growth in RCS Rats.

In the RCS rat transplant study, none of the 79 cell-injected retinas examined, including the longest time points, showed any evidence of uncontrolled cell proliferation. There was no evidence of teratoma and/or tumor formation.

Discussion

These results show the long-term safety and efficacy of hESC-derived RPE cells produced under manufacturing conditions applicable for use in human clinical trials are described herein. In addition to the development of assays with qualified range limits (which constituted the "identity" of the final RPE product), extensive pathogen testing was carried out to ensure that the manufacturing procedure did not introduce any infectious diseases or adventitious agents into the RPE cells.

To confirm the functionality of these GMP-compliant cells, both dose-response and long-term efficacy were evaluated in homologous models of human retinal disease. Because of the proliferative nature of hES cells, evidence of safety under Good Laboratory Practice ("GLP") conditions is imperative for translating hESC-derived cellular products into the clinic. The extensive characterization detailed above provides assurance of cellular identity, whereas the long-term tumorigenicity study presented here provides strong evidence that the hESC-RPE cells are safe and do not form teratomas and/or tumors during the lifetime of NIH III immune-deficient mice. After introduction to the subretinal space of RCS rats, the hESC-derived cells also survived for more than 8 months without evidence of pathological consequences.

The hESC-RPE cells produced according to the methods described herein also rescued visual functions in a dose-dependent fashion: with increased cell concentrations from 5,000 to 50,000, there was an improvement in functional rescue measured with both visual acuity and luminance threshold response. From 50,000 to 100,000, there is tolerance in numbers of cells introduced and that twice the optimal dose is still effective. Previous rodent work has shown that RPE cells quickly disperse as a single or double layer and that 20,000 cells of an immortalized RPE cell line may occupy about 20% of the retinal area (12.56 mm$^2$). For the age-related macular degeneration retina, the inner macular is 3 mm in diameter: this would mean that a dose of about 40,000 cells may be used to cover the inner macular area but that a larger cell number may likely cover a larger area.

The significantly improved visual performance in Elovl4 mice adds to the value of the hESC-RPE as the cell choice for cell-based therapy to treat macular disease (in this case, a subset of patients with Stargardt's disease caused by mutation in the Elovl4 gene). Stargardt's disease is one of the most frequent forms of juvenile macular degeneration. Although some rescue may be achieved by growth factor delivery such as direct injection or factor-releasing cells (encapsulated cells) such as ARPE19 cells transduced to produce ciliary neurotrophic factor or Schwann cells, these approaches cannot replace the other functions of RPE cells. The hESC-RPE cells have a molecular profile more closely resembling native RPE than do ARPE-19, and thus they may be able to take on a broader range of RPE functions than ARPE-19 beyond simple factor delivery. For example, without being bound to a particular mechanism, the hESC-RPE cells may replace crucial functions of the host RPE because the hESC-RPE cells are able to phago-cytose latex beads in vitro. However, because the location of photoreceptor rescue extends beyond the area of donor cell distribution, part of the rescue effect may be mediated by a diffusible trophic factor effect.

These results show the long-term safety of hESC-derived RPE cells in immune-deficient animals, as well as their long-term function in two different animal models of disease using GMP conditions suitable for clinical trials. The presence of differentiated human retinal pigmented epithelial cells was identified incorporated or attached to the retinal pigmented epithelial cell layer of rats over 200 days post surgery. In all cases, the morphology of these human cells was characterized as organized cuboidal epithelial cells with round nuclei displaced by small golden-brown intracytoplasmic pigment, consistent with pigmented epithelial cells. When associated with the mouse RPE, the human cells displayed typical polarity along a basement membrane with basally located nuclei and apically located pigmented granules (FIGS. 13, 14). The human cells could be distinguished from mouse RPE as the human cells appeared slightly larger with fewer and smaller yellow-brown pigmented granules compared to the mouse RPE. Thus at P240 (i.e., 220 days after transplantation), donor cells survive, photoreceptors are rescued, and a level of visual function is preserved. Thus, the methods described herein may serve as a safe and inexhaustible source of RPE cells for the efficacious treatment of a range of retinal degenerative diseases.

Example 23

Rescue of Visual Function Using RPE Cells From Embryonic Stem Cells

Summary

Human embryonic stem cell-derived retinal pigmented epithelium (RPE) cells were assessed for their ability to retard the progression of retinal degeneration in the Royal College of Surgeons (RCS) rats, a well characterized and studied rodent model for retinal degeneration. These animals carry a mutation in the gene for the MER tyrosine kinase (MERTK), which compromises the ability of RPE to perform phagocytosis of shed photoreceptor outer segments. This dysfunction of RPE cells leads to a progressive loss of both rods and cones overtime. Interestingly, mutation within the human orthologue of MERTK results in retinal degeneration, whereby patients exhibit progressive poor visual acuity and visual field losses with age.

RPE cells were subretinally injected in RCS rat eyes at an early stage of retinal degeneration (P21) in order to prevent disease progression. Animals were divided into three groups: cell-injected group, balanced salt solution (BSS)-injected control and untreated eyes. Cells (50,000, 75,000 and 100,000 cells) were injected using BSS as the vehicle for cell delivery. For immune suppression cyclosporine was added to drinking water (210 mg/L) during the study. The efficacy of RPE cell injection was evaluated by two visual functional tests: optomotor responses and luminance threshold recordings from the superior colliculus (SC), followed by morphological examination including cresyl violet staining (for general retinal lamination and photoreceptor thickness). Additionally, immunostaining was performed with antibodies to human nuclei or human mitochondria antibodies to identify surviving human cells and the human RPE-specific marker bestrophin to their RPE phenotype. Both BSS injection alone and untreated eyes were used as control groups these were examined along with cell injected groups at all the time points.

Results—Optomotor Responses

Animals were tested for spatial visual acuity using an optometry testing apparatus (CerebralMechanics, Lethbridge, Canada) comprised of four computer monitors arranged in a square, which projected a virtual three-dimensional space of a rotating cylinder lined with a vertical sine wave grating. Unrestrained animals were placed on a platform in the center of the square, where they tracked the grating with reflexive head movements. The spatial frequency of the grating was clamped at the viewing position by recentering the cylinder on the animal's head. The acuity threshold was quantified by increasing the spatial frequency of the grating using a psychophysics staircase progression until the following response was lost, thus defining the acuity.

All cell-injected and control rats were tested from P60 to P240, the P60 time point was chosen as the earliest time point when difference between cell injection and control can be detected.

Cell-injected animals performed significantly better than BSS injected and untreated controls at all time points tested ($p<0.01$). The majority of the cell-injected animals had visual acuity above 0.5 cycle/degree at P90, which is similar to the visual acuity that non dystrophic rats (0.52-0.60 c/d)(8), while in BSS-injected and untreated control animals, an average of 0.25-0.30 c/d was recorded Luminance Threshold Recording from the Superior Colliculus This test is similar to the Humphrey test used in clinic for visual field analysis in humans. In the case of animals, electrodes are implanted and are measured using sensitive instrumentation. To assess luminance thresholds, single and multi-unit activity in the superficial layers of the super colliculus (SC) was recorded.

Recordings were made from the superficial layers of the SC to a depth of 100-300 μm using glass-coated tungsten electrodes (resistance: 0.5 MΩ bandpass 500 Hz-5 KHz). Small craniotomies of about 100 μm in diameter were made to access the brain. Anatomically, retinal ganglion cells project to contra-lateral superior colliculus (SC), therefore, right eye sends signals to left side of the SC. In the non dystrophic rat retina, there are 10-12 layers of photoreceptors which are very sensitive to light stimuli. In other words, normal retina will respond to very low light stimulation, so normal animals have low luminance threshold (0.2-0.4 log units). In the dystrophic rat retina at P90, due to loss of photoreceptors, animals will only respond to high intensity light stimulation, therefore these animals have a high luminance threshold (2.5-3.0 log units). Since the unit is expressed as logarithmic scale, 0.2 log units in a normal retina is more than 100 times more sensitive to light than 2.5 log units in a dystrophic retina.

Lower luminance thresholds were recorded in cell-injected eyes compared with BSS alone and untreated control eyes. Several of the cell-injected eyes had luminance thresholds of 0.7-0.8 log units, compared with 3.0 log units in untreated fellow eye (over 100 times more sensitive to light stimulation).

The luminance threshold recorded from the SC correlated well with the amount of photoreceptors in the retina. Animals with more photoreceptors were more sensitive to light stimulation, i.e. had a lower luminance threshold. For example, one rat had extensive photoreceptor preservation, which correlated with donor cell distribution. Optomotor response revealed visual acuity of 0.50 c/d compared with 0.25 c/d in untreated eye, and luminance threshold recording gave a figure of 0.8 log units at P90, compared with 3.0 log units in untreated control, which is more than 100 times more sensitive to light stimulation.

Histology

General Retinal Lamination

At the termination of the experiment, all animals were sacrificed by sodium pentobarbital overdose and perfused with phosphate-buffered saline. The eyes were removed and immersed in paraformaldehyde for one hour, infiltrated with sucrose, embedded in OCT medium and cut into horizontal cryosections. All the retinal sections from cell-injected, BSS-injected and untreated controls were stained with cresyl violet for general retinal lamination, identifying the injection site. There was no evidence of abnormal growth, teratoma formation or any other unwanted pathology.

HES-RPE Cell Survival

To confirm survival of human donor cells in rat eyes, the sections were double stained with anti-human mitochondria and anti-human bestrophin antibodies. Frozen eye sections were not originally intended for harsh antigen retrieval procedures required for anti-human mitochondria staining; thus a large number of sections was lost (came off the slides fully or partially, resulting in poor morphology). The assay was further optimized allowing double staining for anti-human nuclei and bestrophin with good preservation of eye morphology. RPE cells were confirmed as present in 13 of 34 animals (38%). The majority of human cells (all but one animal where RPE cells were found in the intravitreous cavity) were found at long term survival endpoints (P180-249), integrated into rat RPE layer, and all had typical RPE morphology and were positive for the RPE marker bestrophin which confirms the survival and preservation of RPE identity at long-term post-transplantation in vivo.

Photoreceptor Preservation and Donor Cell Distribution

In cell-injected retina, there were 3-6 layers of photoreceptors compared with localized 1-2 layers of photoreceptors around injection site in BSS control injection or a single layer of photoreceptors in untreated retina at P90 thus pointing to photoreceptor preservation being associated with transplanted RPE cells. In BSS-injected eyes, 1-2 cells thick localized rescue of photoreceptors was observed adjacent to injection site around P90-100; however the effect was no longer evident at later time points examined in this study. Luminance threshold recording also revealed this effect (usually one point had a lower luminance threshold) two months after injection. With time, the effect of BSS injection disappeared while in cell-injected retina photoreceptor preservation was seen out to P249 (over 225 days post-injection). in addition, the secondary pathology related to progressive degeneration was largely prevented, while in BSS injected and untreated retinas, typical secondary changes including vascular pathology and inner retinal neurons migrating into inner retina were clearly evident. Human specific antibody staining revealed hRPE cells surviving for over 225 days post-injection. The distribution of hES-RPE cells correlated with preserved photoreceptor.

Conclusion

In all the retinas examined in this example, long-term preservation of both morphology and function after cell injection was demonstrated. The RPE cells survived for at least 225 days, integrated into rat RPE layer and expressed the RPE cell specific marker bestrophin. No evidence of unwanted overgrowth or teratoma formation was found. Therefore, the RPE cells described herein may be transplanted where they survive, maintain their phenotype, and rescue visual acuity in retinal degeneration.

Example 24

Treatment of Patient with Diabetic Retinopathy

A human patient diagnosed with diabetic retinopathy may be treated by administering a pharmaceutical preparation comprising at least about 100,000 human RPE cells (e.g., 100,000 RPE cells in 50 µL). The RPE cell preparation is injected into sub-retinal space. The patient is placed on a treatment course of 5 mg/kg cyclosporin for 6 weeks. The patient is monitored for the development of side effects. The visual acuity of the patient is monitored and tested at least for 6 months following treatment.

Example 25

Treatment of Patient with Age-Related Macular Degeneration

A human patient diagnosed with age-related macular degeneration may be treated by administering a pharmaceutical preparation comprising at least about 100,000 human RPE cells (e.g., 100,000 RPE cells in 50 µL). Prior to transplantation, the RPE cells may be cultured under conditions that increase alpha-integrin subunit expression. The RPE cell preparation is injected into sub-retinal space. The patient is placed on a treatment course of 5 mg/kg cyclosporin for 6 weeks. The patient is monitored for the development of side effects. The visual acuity of the patient is monitored and tested at least for 6 months following treatment.

Example 26

Treatment of Patient with Retinal Pigmentosa

A human patient diagnosed with retinal pigmentosa may be treated by administering a pharmaceutical preparation comprising at least about 100,000 human RPE cells (e.g., 100,000 RPE cells in 50 µL). The RPE cell preparation is injected into sub-retinal space. The patient is placed on a treatment course of 5 mg/kg cyclosporin for 6 weeks. The patient is monitored for the development of side effects. The visual acuity of the patient is monitored and tested at least for 6 months following treatment.

Example 27

Treatment of Patient with Stargardt's Disease

A human patient diagnosed with Stargardt's Disease (fundus flavimaculatus) may be treated by administering a pharmaceutical preparation comprising at least about 100,000 human RPE cells (e.g., 100,000 RPE cells in 50 µL). The RPE cell preparation is injected into sub-retinal space. The patient is placed on a treatment course of 5 mg/kg cyclosporin for 6 weeks. The patient is monitored for the development of side effects. The visual acuity of the patient is monitored and tested at least for 6 months following treatment.

All publications, patents and patent applications are herein incorporated by reference in their entirety to the same extent as if each individual publication, patent or patent application was specifically and individually indicated to be incorporated by reference in its entirety. U.S. Provisional Patent Application Nos. 60/998,766, filed Oct. 12, 2007, 60/998,668, filed Oct. 12, 2007, 61/009,908, filed Jan. 2, 2008, and 61/009,911, filed Jan. 2, 2008, the disclosures of each of the foregoing applications are hereby incorporated by reference in their entirety. In addition, the disclosure of WO 2009/05 1671 is hereby incorporated by reference in its entirety.

Those skilled in the art will recognize, or be able to ascertain using no more than routine experimentation, many equivalents to the specific embodiments of the invention described herein. Such equivalents are intended to be encompassed by the following claims.

We claim:

1. A method of producing a pharmaceutical preparation or a cryopreserved composition of human RPE cells comprising
   (a) culturing human pluripotent stem cells under non-adherent conditions for 7-14 days to form cell masses;
   (b) culturing the cell masses to form an adherent culture comprising human RPE cells;
   (c) dissociating human RPE cells from the adherent culture;
   (d) culturing said dissociated RPE cells to about 95-100% confluency and a medium pigmentation;
   (e) dissociating the human RPE cells of (d);
   (f) repeating steps (d) to (e) at least once;
   (g) harvesting a population of said dissociated human RPE cells;
   (h) detecting expression of (i) ZO-1 and (ii) Pax6 and/or MITF in an aliquot of the harvested population to partially characterize the harvested population; and
   (i) formulating at least a portion of the harvested population as a pharmaceutical preparation or a cryopreserved composition of RPE cells if the harvested population is characterized as
      (1) ≥95% of the cells in the harvested population are positive for PAX6 and/or MITF by immunostaining; and/or ≥95% of the cells in the harvested population are positive for PAX6 and/or bestrophin by immunostaining; and
      (2) ≥95% of the cells in the harvested population are positive for ZO-1 by immunostaining; and
      (3) the harvested population is negative for Oct-4, Nanog, Rex-1 and Sox2 by qPCR; and
      (4) the harvested population is negative for Oct-4 and alkaline phosphatase by immunostaining;
   wherein RPE cells of the harvested population survive in vivo at least about 6 months, and
   wherein the culture conditions are not permissive to pluripotent stem cells.

2. The method of claim 1, wherein said human pluripotent stem cells are selected from human induced pluripotent stem (iPS) cells, human embryonic stem (ES) cells, human adult stem cells, hematopoietic stem cells, fetal stem cells, mesenchymal stem cells, postpartum stem cells, multipotent stem cells or embryonic germ cells.

3. The method of claim 1, wherein in step (e) the human RPE cells are dissociated using an enzyme selected from trypsin, collagenase, dispase, papain, a mixture of collagenase and dispase, and a mixture of collagenase and trypsin.

4. A pharmaceutical preparation or cryopreserved composition comprising human RPE cells prepared by the method of claim 1.

5. The method of claim 1, wherein the human RPE cells in the harvested population are
   (1) positive for bestrophin, RPE-65, CRALBP, PEDF, PAX6 and MITF by qPCR, and/or
   (2) positive for bestrophin, CRALBP, PAX6, MITF and ZO-1 by immunostaining.

6. The method of claim 1, wherein greater than or equal to 85% of the human RPE cells in the harvested population are viable.

7. The method of claim 1, wherein at least a portion of the harvested population is formulated as a cryopreserved composition and wherein greater than or equal to 70% of the human RPE cells therein are viable after cryopreservation.

8. The pharmaceutical preparation or cryopreserved composition of claim 4, wherein greater than or equal to 85% of the human RPE cells are viable prior to cryopreservation and/or greater than or equal to 70% of the human RPE cells are viable after cryopreservation.

9. The pharmaceutical preparation or cryopreserved composition of claim 4, wherein the human RPE cells are provided as a suspension of cells.

10. The pharmaceutical preparation or cryopreserved composition of claim 4, wherein the human RPE cells are provided in a pharmaceutical preparation and are disposed on a matrix.

11. The method of claim 1, wherein the method steps are conducted in accordance with Good Manufacturing Practices (GMP) or Good Tissue Practices (GTP).

12. The method of claim 1, wherein the dissociated RPE cells in (d) are cultured in RPE-GM.

13. The method of claim 1, wherein the dissociated RPE cells in (d) are cultured in RPE-MM.

* * * * *